US010702409B2

United States Patent
Burns et al.

(10) Patent No.: US 10,702,409 B2
(45) Date of Patent: Jul. 7, 2020

(54) CLOSURE DEVICES FOR MEDICAL DEVICES AND METHODS

(71) Applicant: Boa Technology Inc., Denver, CO (US)

(72) Inventors: Robert Burns, Denver, CO (US); James Capra, Steamboat Springs, CO (US); Tamara White, Denver, CO (US); Mark Soderberg, Conifer, CO (US)

(73) Assignee: Boa Technology Inc., Denver, CO (US)

( * ) Notice: Subject to any disclaimer, the term of this patent is extended or adjusted under 35 U.S.C. 154(b) by 769 days.

(21) Appl. No.: 14/173,685

(22) Filed: Feb. 5, 2014

(65) Prior Publication Data

US 2014/0221889 A1 Aug. 7, 2014

Related U.S. Application Data

(60) Provisional application No. 61/761,059, filed on Feb. 5, 2013.

(51) Int. Cl.
*A61F 5/01* (2006.01)

(52) U.S. Cl.
CPC .................. *A61F 5/0102* (2013.01)

(58) Field of Classification Search
CPC ........... A61F 5/01–3792; A43C 11/165; A43C 11/00–24; Y10T 24/16; Y10T 24/1648; Y10T 24/168; Y10T 24/2183; Y10T 24/45–45225; Y10T 24/47; Y10T 24/1604; Y10T 24/21; Y10T 24/45021; Y10T 24/45037; Y10T 24/45063; Y10T 24/45079; Y10T 24/45084; Y10T 24/34–3403; A41F 1/00; A41F 1/04; A41F 1/08; A43B 5/00–185

See application file for complete search history.

(56) References Cited

U.S. PATENT DOCUMENTS

| | | |
|---|---|---|
| 59,332 A | 10/1866 | White et al. |
| 80,834 A | 8/1868 | Prussia |
| 117,530 A | 8/1871 | Foote |
| 228,946 A | 6/1880 | Schulz |

(Continued)

FOREIGN PATENT DOCUMENTS

| | | |
|---|---|---|
| AT | 127075 | 2/1932 |
| AT | 244804 | 1/1966 |

(Continued)

OTHER PUBLICATIONS

U.S. Appl. No. 09/956,601, filed Sep. 18, 2001, Hammerslag.

(Continued)

*Primary Examiner* — Keri J Nelson
*Assistant Examiner* — Michelle J Lee
(74) *Attorney, Agent, or Firm* — Kilpatrick Townsend & Stockton, LLP

(57) ABSTRACT

Closure devices that may be used for various articles, such as braces, medical devices, shoes, clothing, apparel, and the like. The closure devices may include a tightening mechanism that may function as a handle that allows an individual to wrap an article around body part, couple the article about the body part, and then tension or tighten the article using a single hand.

11 Claims, 33 Drawing Sheets

(56) References Cited

U.S. PATENT DOCUMENTS

| | | |
|---|---|---|
| 230,759 A | 8/1880 | Drummond |
| 379,113 A | 3/1888 | Hibberd |
| 746,563 A | 12/1903 | McMahon |
| 819,993 A | 5/1906 | Haws et al. |
| 908,704 A | 1/1909 | Sprinkle |
| 1,060,422 A | 4/1913 | Bowdish |
| 1,062,511 A | 5/1913 | Short |
| 1,083,775 A | 1/1914 | Thomas |
| 1,090,438 A | 3/1914 | Worth et al. |
| 1,170,472 A | 2/1916 | Barber |
| 1,288,859 A | 12/1918 | Feller et al. |
| 1,390,991 A | 9/1921 | Fotchuk |
| 1,393,188 A | 10/1921 | Whiteman |
| 1,469,661 A | 2/1922 | Migita |
| 1,412,486 A | 4/1922 | Paine |
| 1,416,203 A | 5/1922 | Hobson |
| 1,429,657 A | 9/1922 | Trawinski |
| 1,481,903 A | 4/1923 | Hart |
| 1,466,673 A | 9/1923 | Solomon et al. |
| 1,530,713 A | 2/1924 | Clark |
| 1,502,919 A | 7/1924 | Seib |
| 1,862,047 A | 6/1932 | Boulet et al. |
| 1,995,243 A | 6/1934 | Clarke |
| 2,088,851 A | 8/1937 | Gantenbein |
| 2,109,751 A | 3/1938 | Matthias et al. |
| 2,124,310 A | 9/1938 | Murr, Jr. |
| 2,316,102 A | 4/1943 | Preston |
| 2,539,026 A | 1/1951 | Mangold |
| 2,611,940 A | 9/1952 | Cairns |
| 2,673,381 A | 3/1954 | Dueker |
| 2,907,086 A | 10/1959 | Ord |
| 2,991,523 A | 7/1961 | Del Conte |
| 3,028,602 A | 4/1962 | Miller |
| 3,035,319 A | 5/1962 | Wolff |
| 3,106,003 A | 10/1963 | Herdman |
| 3,112,545 A | 12/1963 | Williams |
| 3,122,810 A | 3/1964 | Lawrence et al. |
| 3,163,900 A | 1/1965 | Martin |
| D200,394 S | 2/1965 | Hakim |
| 3,169,325 A | 2/1965 | Fesl |
| 3,193,950 A | 7/1965 | Liou |
| 3,197,155 A | 7/1965 | Chow |
| 3,221,384 A | 12/1965 | Aufenacker |
| 3,276,090 A | 10/1966 | Nigon |
| D206,146 S | 11/1966 | Hendershot |
| 3,345,707 A | 10/1967 | Rita |
| D210,649 S | 4/1968 | Getgay |
| 3,401,437 A | 9/1968 | Christpohersen |
| 3,430,303 A | 3/1969 | Perrin et al. |
| 3,445,901 A * | 5/1969 | Kamper .............. A41F 1/00 24/618 |
| 3,491,465 A | 1/1970 | Martin |
| 3,545,106 A | 12/1970 | Martin |
| 3,618,232 A | 11/1971 | Shnuriwsky |
| 3,668,791 A | 6/1972 | Salzman et al. |
| 3,678,539 A | 7/1972 | Graup |
| 3,703,775 A | 11/1972 | Gatti |
| 3,729,779 A | 5/1973 | Porth |
| 3,738,027 A | 6/1973 | Schoch |
| 3,793,749 A | 2/1974 | Gertsch et al. |
| 3,808,644 A | 5/1974 | Schoch |
| 3,934,346 A | 1/1976 | Sasaki et al. |
| 3,975,838 A | 8/1976 | Martin |
| 4,084,267 A | 4/1978 | Zadina |
| 4,130,949 A | 12/1978 | Seidel |
| 4,142,307 A | 3/1979 | Martin |
| 4,227,322 A | 10/1980 | Annovi |
| 4,261,081 A | 4/1981 | Lott |
| 4,267,622 A | 5/1981 | Burnett-Johnston |
| 4,408,403 A | 10/1983 | Martin |
| 4,417,703 A | 11/1983 | Weinhold |
| 4,433,456 A | 2/1984 | Baggio |
| 4,463,761 A | 8/1984 | Pols et al. |
| 4,480,395 A | 11/1984 | Schoch |
| 4,507,878 A | 4/1985 | Semouha |
| 4,551,932 A | 11/1985 | Schoch |
| 4,555,830 A | 12/1985 | Petrini et al. |
| 4,574,500 A | 3/1986 | Aldinio et al. |
| 4,616,432 A | 10/1986 | Bunch et al. |
| 4,616,524 A | 10/1986 | Biodia |
| 4,619,057 A | 10/1986 | Sartor et al. |
| 4,620,378 A | 11/1986 | Sartor |
| 4,631,839 A | 12/1986 | Bonetti et al. |
| 4,631,840 A | 12/1986 | Gamm |
| 4,633,599 A | 1/1987 | Morell et al. |
| 4,644,938 A | 2/1987 | Yates et al. |
| 4,654,985 A | 4/1987 | Chalmers |
| 4,660,300 A | 4/1987 | Morell et al. |
| 4,660,302 A | 4/1987 | Arieh et al. |
| 4,680,878 A | 7/1987 | Pozzobon et al. |
| 4,719,670 A | 1/1988 | Kurt |
| 4,719,709 A | 1/1988 | Vaccari |
| 4,719,710 A | 1/1988 | Pozzobon |
| 4,722,477 A | 2/1988 | Floyd |
| 4,741,115 A | 5/1988 | Pozzobon |
| 4,748,726 A | 6/1988 | Schoch |
| 4,760,653 A | 8/1988 | Baggio |
| 4,780,969 A | 11/1988 | White, Jr. |
| 4,787,124 A | 11/1988 | Pozzobon et al. |
| 4,790,081 A | 12/1988 | Benoit et al. |
| 4,796,829 A | 1/1989 | Pozzobon et al. |
| 4,799,297 A | 1/1989 | Baggio et al. |
| 4,802,291 A | 2/1989 | Sartor |
| 4,811,503 A | 3/1989 | Iwama |
| 4,826,098 A | 5/1989 | Pozzobon et al. |
| 4,841,649 A | 6/1989 | Baggio et al. |
| 4,856,207 A | 8/1989 | Datson |
| 4,862,878 A | 9/1989 | Davison |
| 4,870,723 A | 10/1989 | Pozzobon et al. |
| 4,870,761 A | 10/1989 | Tracy |
| 4,884,760 A | 12/1989 | Baggio et al. |
| 4,901,938 A | 2/1990 | Cantley et al. |
| 4,924,605 A | 5/1990 | Spademan |
| D308,282 S | 6/1990 | Bergman et al. |
| 4,937,953 A | 7/1990 | Walkhoff |
| 4,961,544 A | 10/1990 | Biodia |
| 4,989,805 A | 2/1991 | Burke |
| 5,001,817 A | 3/1991 | De Bortoli et al. |
| 5,016,327 A | 5/1991 | Klausner |
| 5,042,177 A | 8/1991 | Schoch |
| 5,062,225 A | 11/1991 | Gorza |
| 5,065,480 A | 11/1991 | DeBortoli |
| 5,065,481 A | 11/1991 | Walkhoff |
| 5,108,216 A | 4/1992 | Geyer et al. |
| 5,117,567 A | 6/1992 | Berger |
| 5,152,038 A | 10/1992 | Schoch |
| 5,157,813 A | 10/1992 | Carroll |
| 5,158,428 A | 10/1992 | Gessner et al. |
| 5,177,882 A | 1/1993 | Berger |
| 5,181,331 A | 1/1993 | Berger |
| 5,184,378 A | 2/1993 | Batra |
| D333,552 S | 3/1993 | Berger et al. |
| 5,205,055 A | 4/1993 | Harrell |
| 5,233,767 A | 8/1993 | Kramer |
| 5,249,377 A | 10/1993 | Walkhoff |
| 5,259,094 A | 11/1993 | Zepeda |
| 5,315,741 A | 5/1994 | Debberke |
| 5,319,868 A | 6/1994 | Hallenbeck |
| 5,319,869 A | 6/1994 | McDonald et al. |
| 5,325,613 A | 7/1994 | Sussmann |
| 5,327,662 A | 7/1994 | Hallenbeck |
| 5,335,401 A | 8/1994 | Hanson |
| 5,341,583 A | 8/1994 | Hallenbeck |
| 5,344,390 A * | 9/1994 | Motloch .............. A43B 5/0433 36/87 |
| 5,345,697 A | 9/1994 | Quellais |
| 5,355,596 A | 10/1994 | Sussmann |
| 5,357,654 A | 10/1994 | Hsing-Chi |
| 5,371,957 A | 12/1994 | Gaudio |
| 5,381,609 A | 1/1995 | Hieblinger |
| 5,392,535 A | 2/1995 | Van Noy et al. |
| D357,576 S | 4/1995 | Steinweis |
| 5,425,161 A | 6/1995 | Schoch |
| 5,425,185 A | 6/1995 | Gansler |

(56) References Cited

U.S. PATENT DOCUMENTS

| | | |
|---|---|---|
| 5,430,960 A | 7/1995 | Richardson |
| 5,433,648 A | 7/1995 | Frydman |
| 5,463,822 A | 11/1995 | Miller |
| 5,477,593 A | 12/1995 | Leick |
| D367,755 S | 3/1996 | Jones |
| D367,954 S | 3/1996 | Dion |
| 5,502,902 A | 4/1996 | Sussmann |
| 5,511,325 A | 4/1996 | Hieblinger |
| 5,526,585 A | 6/1996 | Brown et al. |
| 5,535,531 A | 7/1996 | Karabed et al. |
| 5,537,763 A | 7/1996 | Donnadieu et al. |
| 5,557,864 A | 9/1996 | Marks |
| 5,566,474 A | 10/1996 | Leick et al. |
| D375,831 S | 11/1996 | Perry |
| 5,596,820 A | 1/1997 | Edauw et al. |
| 5,599,000 A | 2/1997 | Bennett |
| 5,599,288 A | 2/1997 | Shirley et al. |
| 5,600,874 A | 2/1997 | Jungkind |
| 5,606,778 A | 3/1997 | Jungkind |
| D379,113 S | 5/1997 | McDonald et al. |
| 5,638,588 A | 6/1997 | Jungkind |
| 5,640,785 A | 6/1997 | Egelja |
| 5,647,104 A | 7/1997 | James |
| 5,651,198 A | 7/1997 | Sussmann |
| 5,669,116 A | 9/1997 | Jungkind |
| 5,692,319 A | 12/1997 | Parker et al. |
| 5,718,021 A | 2/1998 | Tatum |
| 5,718,065 A | 2/1998 | Locker |
| 5,720,084 A | 2/1998 | Chen |
| 5,732,483 A | 3/1998 | Cagliari |
| 5,732,648 A | 3/1998 | Aragon |
| 5,736,696 A | 4/1998 | Del Rosso |
| 5,737,854 A | 4/1998 | Sussmann |
| 5,755,044 A | 5/1998 | Veylupek |
| 5,756,298 A | 5/1998 | Burczak |
| 5,761,777 A | 6/1998 | Leick |
| 5,772,146 A | 6/1998 | Kawamoto et al. |
| 5,784,809 A | 7/1998 | McDonald |
| 5,791,068 A | 8/1998 | Bernier et al. |
| 5,819,378 A | 10/1998 | Doyle |
| 5,833,640 A | 11/1998 | Vazquez, Jr. et al. |
| 5,839,210 A | 11/1998 | Bernier et al. |
| 5,845,371 A | 12/1998 | Chen |
| 5,909,946 A | 6/1999 | Okajima |
| D413,197 S | 8/1999 | Faye |
| 5,934,599 A | 8/1999 | Hammerslag |
| 5,937,542 A | 8/1999 | Bourdeau |
| 5,956,823 A | 9/1999 | Borel |
| 5,971,946 A | 10/1999 | Quinn et al. |
| 6,015,110 A | 1/2000 | Lai |
| 6,038,791 A | 3/2000 | Cornelius et al. |
| 6,052,921 A | 4/2000 | Oreck |
| 6,070,886 A | 6/2000 | Cornelius et al. |
| 6,070,887 A | 6/2000 | Cornelius et al. |
| 6,083,857 A | 7/2000 | Bottger |
| 6,088,936 A | 7/2000 | Bahl |
| 6,102,412 A | 8/2000 | Staffaroni |
| D430,724 S | 9/2000 | Matis et al. |
| 6,119,318 A | 9/2000 | Maurer |
| 6,119,372 A | 9/2000 | Okajima |
| 6,128,835 A | 10/2000 | Ritter et al. |
| 6,128,836 A | 10/2000 | Barret |
| 6,148,489 A | 11/2000 | Dickie et al. |
| 6,202,953 B1 | 3/2001 | Hammerslag |
| 6,219,891 B1 | 4/2001 | Maurer et al. |
| 6,240,657 B1 | 6/2001 | Weber et al. |
| 6,256,798 B1 | 7/2001 | Egolf et al. |
| 6,267,390 B1 | 7/2001 | Maravetz et al. |
| 6,286,233 B1 | 9/2001 | Gaither |
| 6,289,558 B1 | 9/2001 | Hammerslag |
| 6,311,633 B1 | 11/2001 | Keire |
| D456,130 S | 4/2002 | Towns |
| 6,370,743 B2 | 4/2002 | Choe |
| 6,401,364 B1 | 6/2002 | Burt |
| 6,416,074 B1 | 7/2002 | Maravetz et al. |
| 6,467,195 B2 | 10/2002 | Pierre et al. |
| 6,477,793 B1 | 11/2002 | Pruitt et al. |
| 6,502,286 B1 | 1/2003 | Dubberke |
| 6,543,159 B1 | 4/2003 | Carpenter et al. |
| 6,568,103 B2 | 5/2003 | Durocher |
| 6,606,304 B1 | 8/2003 | Kaneko et al. |
| 6,606,804 B2 | 8/2003 | Kaneko et al. |
| 6,694,643 B1 | 2/2004 | Hsu |
| 6,708,376 B1 | 3/2004 | Landry |
| 6,711,787 B2 | 3/2004 | Jungkind et al. |
| 6,735,829 B2 | 5/2004 | Hsu |
| 6,757,991 B2 | 7/2004 | Sussmann |
| 6,775,928 B2 | 8/2004 | Grande et al. |
| 6,792,702 B2 | 9/2004 | Borsoi et al. |
| 6,802,439 B2 | 10/2004 | Azam et al. |
| 6,823,610 B1 | 11/2004 | Ashley |
| 6,871,812 B1 | 3/2005 | Chang |
| 6,877,256 B2 | 4/2005 | Martin et al. |
| 6,922,917 B2 | 8/2005 | Kerns et al. |
| 6,938,913 B2 | 9/2005 | Elkington |
| 6,945,543 B2 | 9/2005 | De Bertoli et al. |
| D510,183 S | 10/2005 | Tresser |
| 6,976,972 B2 | 12/2005 | Bradshaw |
| 6,993,859 B2 | 2/2006 | Martin et al. |
| D521,226 S | 5/2006 | Douglas et al. |
| 7,073,279 B2 | 7/2006 | Min |
| 7,076,843 B2 | 7/2006 | Sakabayashi |
| 7,082,701 B2 | 8/2006 | Dalgaard et al. |
| 7,096,559 B2 | 8/2006 | Johnson et al. |
| 7,134,224 B2 | 11/2006 | Elkington et al. |
| 7,266,911 B2 | 9/2007 | Holzer et al. |
| 7,281,341 B2 | 10/2007 | Reagan et al. |
| 7,293,373 B2 | 11/2007 | Reagan et al. |
| 7,331,126 B2 | 2/2008 | Johnson |
| 7,343,701 B2 | 3/2008 | Pare et al. |
| 7,367,522 B2 | 5/2008 | Chen |
| 7,386,947 B2 | 6/2008 | Martin et al. |
| 7,392,602 B2 | 7/2008 | Reagan et al. |
| 7,401,423 B2 | 7/2008 | Reagan et al. |
| 7,490,458 B2 | 2/2009 | Ford |
| 7,568,298 B2 | 8/2009 | Kerns |
| 7,584,528 B2 | 9/2009 | Hu |
| 7,591,050 B2 * | 9/2009 | Hammerslag ............ A43B 5/16 24/68 SK |
| 7,597,675 B2 | 10/2009 | Ingimundarson et al. |
| 7,600,660 B2 | 10/2009 | Kasper et al. |
| 7,617,573 B2 | 11/2009 | Chen |
| 7,624,517 B2 | 12/2009 | Smith |
| 7,648,404 B1 | 1/2010 | Martin |
| 7,650,705 B2 | 1/2010 | Donnadieu et al. |
| 7,694,354 B2 | 4/2010 | Philpott et al. |
| 7,752,774 B2 | 7/2010 | Ussher |
| 7,757,412 B2 | 7/2010 | Farys |
| 7,774,956 B2 | 8/2010 | Dua et al. |
| D626,322 S | 11/2010 | Servettaz |
| 7,841,106 B2 | 11/2010 | Farys |
| 7,871,334 B2 | 1/2011 | Young et al. |
| 7,877,845 B2 | 2/2011 | Signori |
| 7,900,378 B1 | 3/2011 | Busse |
| 7,908,769 B2 | 3/2011 | Pellegrini |
| 7,950,112 B2 | 5/2011 | Hammerslag et al. |
| 7,954,204 B2 | 6/2011 | Hammerslag et al. |
| 7,963,049 B2 | 6/2011 | Messmer |
| 7,992,261 B2 | 8/2011 | Hammerslag et al. |
| D646,790 S | 10/2011 | Castillo et al. |
| 8,056,150 B2 | 11/2011 | Stokes et al. |
| 8,074,379 B2 | 12/2011 | Robinson, Jr. et al. |
| 8,091,182 B2 | 1/2012 | Hammerslag et al. |
| 8,109,015 B2 | 2/2012 | Signori |
| D663,850 S | 7/2012 | Joseph |
| D663,851 S | 7/2012 | Joseph |
| 8,215,033 B2 | 7/2012 | Carboy et al. |
| 8,231,074 B2 | 7/2012 | Hu et al. |
| D665,088 S | 8/2012 | Joseph |
| 8,235,321 B2 | 8/2012 | Chen |
| 8,245,371 B2 | 8/2012 | Chen |
| 8,257,293 B2 | 9/2012 | Ingimundarson et al. |
| 8,266,827 B2 | 9/2012 | Dojan et al. |
| 8,277,401 B2 | 10/2012 | Hammerslag et al. |

(56) References Cited

U.S. PATENT DOCUMENTS

| | | | |
|---|---|---|---|
| 8,302,329 B2 | 11/2012 | Hurd et al. |
| 8,303,527 B2 | 11/2012 | Joseph |
| 8,308,098 B2 | 11/2012 | Chen |
| 8,353,087 B2 | 1/2013 | Chen |
| 8,353,088 B2 | 1/2013 | Ha |
| D677,045 S | 3/2013 | Voskuil |
| 8,434,200 B2 | 5/2013 | Chen |
| 8,490,299 B2 | 7/2013 | Dua et al. |
| 8,516,662 B2 | 8/2013 | Goodman et al. |
| 8,578,632 B2 | 11/2013 | Bell et al. |
| 8,713,820 B2 | 5/2014 | Kerns et al. |
| 8,984,719 B2 | 3/2015 | Soderberg et al. |
| D735,987 S | 8/2015 | Hsu |
| 9,101,181 B2 | 8/2015 | Soderberg et al. |
| 9,125,455 B2 | 9/2015 | Kerns et al. |
| 9,138,030 B2 | 9/2015 | Soderberg et al. |
| 2002/0050076 A1 | 5/2002 | Borsoi et al. |
| 2002/0062579 A1 | 5/2002 | Caeran |
| 2002/0095750 A1 | 7/2002 | Hammerslag |
| 2002/0129518 A1 | 9/2002 | Borsoi et al. |
| 2002/0148142 A1 | 10/2002 | Oorei et al. |
| 2002/0166260 A1 | 11/2002 | Borsoi |
| 2002/0178548 A1 | 12/2002 | Freed |
| 2003/0079376 A1 | 5/2003 | Oorei et al. |
| 2003/0144620 A1 | 7/2003 | Sieller |
| 2003/0150135 A1 | 8/2003 | Liu |
| 2003/0177662 A1 | 9/2003 | Elkington et al. |
| 2003/0204938 A1 | 11/2003 | Hammerslag |
| 2004/0041452 A1 | 3/2004 | Williams |
| 2004/0211039 A1 | 10/2004 | Livingston |
| 2005/0054962 A1 | 3/2005 | Bradshaw |
| 2005/0060912 A1 | 3/2005 | Holzer et al. |
| 2005/0081339 A1 | 4/2005 | Sakabayashi |
| 2005/0081403 A1 | 4/2005 | Mathieu |
| 2005/0087115 A1 | 4/2005 | Martin |
| 2005/0098673 A1 | 5/2005 | Huang |
| 2005/0102861 A1 | 5/2005 | Martin |
| 2005/0126043 A1 | 6/2005 | Reagan et al. |
| 2005/0172463 A1 | 8/2005 | Rolla |
| 2005/0184186 A1 | 8/2005 | Tsoi et al. |
| 2005/0198866 A1 | 9/2005 | Wiper et al. |
| 2006/0135901 A1 | 6/2006 | Ingimundarson et al. |
| 2006/0156517 A1 | 7/2006 | Hammerslag et al. |
| 2006/0179685 A1 | 8/2006 | Borel et al. |
| 2006/0185193 A1 | 8/2006 | Pellegrini |
| 2006/0287627 A1 | 12/2006 | Johnson |
| 2007/0006489 A1 | 1/2007 | Case, Jr. et al. |
| 2007/0063459 A1 | 3/2007 | Kavarsky |
| 2007/0068040 A1 | 3/2007 | Farys |
| 2007/0084956 A1 | 4/2007 | Chen |
| 2007/0113524 A1 | 5/2007 | Lander |
| 2007/0128959 A1 | 6/2007 | Cooke |
| 2007/0169378 A1 | 7/2007 | Sodeberg et al. |
| 2007/0271824 A1* | 11/2007 | Holzer .................. A43B 5/0433 36/87 |
| 2008/0016717 A1 | 1/2008 | Ruban |
| 2008/0060167 A1 | 3/2008 | Hammerslag et al. |
| 2008/0060168 A1 | 3/2008 | Hammerslag et al. |
| 2008/0066272 A1* | 3/2008 | Hammerslag .......... A43C 11/14 24/712 |
| 2008/0066345 A1 | 3/2008 | Hammerslag et al. |
| 2008/0066346 A1 | 3/2008 | Hammerslag et al. |
| 2008/0068204 A1 | 3/2008 | Carmen et al. |
| 2008/0083135 A1 | 4/2008 | Hammerslag et al. |
| 2008/0092279 A1 | 4/2008 | Chiang |
| 2008/0172848 A1 | 7/2008 | Chen |
| 2008/0196224 A1 | 8/2008 | Hu |
| 2009/0019734 A1 | 1/2009 | Reagan et al. |
| 2009/0071041 A1 | 3/2009 | Hooper |
| 2009/0090029 A1 | 4/2009 | Kishino |
| 2009/0172928 A1 | 7/2009 | Messmer et al. |
| 2009/0184189 A1 | 7/2009 | Soderberg et al. |
| 2009/0272007 A1 | 11/2009 | Beers et al. |
| 2009/0277043 A1 | 11/2009 | Graser et al. |
| 2010/0064547 A1 | 3/2010 | Kaplan |
| 2010/0101061 A1 | 4/2010 | Ha |
| 2010/0139057 A1 | 6/2010 | Soderberg et al. |
| 2010/0154254 A1 | 6/2010 | Fletcher |
| 2010/0175163 A1 | 7/2010 | Litke |
| 2010/0251524 A1 | 10/2010 | Chen |
| 2010/0299959 A1 | 12/2010 | Hammerslag |
| 2010/0319216 A1 | 12/2010 | Grenzke et al. |
| 2011/0000173 A1 | 1/2011 | Lander |
| 2011/0071647 A1 | 3/2011 | Mahon |
| 2011/0162236 A1 | 7/2011 | Voskuil et al. |
| 2011/0167543 A1 | 7/2011 | Kovacevich et al. |
| 2011/0191992 A1 | 8/2011 | Chen |
| 2011/0197362 A1 | 8/2011 | Chella et al. |
| 2011/0225843 A1 | 9/2011 | Kerns et al. |
| 2011/0258876 A1 | 10/2011 | Baker et al. |
| 2011/0266384 A1 | 11/2011 | Goodman et al. |
| 2012/0000091 A1 | 1/2012 | Cotterman et al. |
| 2012/0004587 A1 | 1/2012 | Nickel et al. |
| 2012/0005995 A1 | 1/2012 | Emery |
| 2012/0023717 A1 | 2/2012 | Chen |
| 2012/0101417 A1 | 4/2012 | Joseph |
| 2012/0102783 A1 | 5/2012 | Swigart et al. |
| 2012/0138882 A1 | 6/2012 | Moore et al. |
| 2012/0157902 A1* | 6/2012 | Castillo ................ A61F 5/0123 602/26 |
| 2012/0167290 A1 | 7/2012 | Kovacevich et al. |
| 2012/0174437 A1 | 7/2012 | Heard |
| 2012/0228419 A1 | 9/2012 | Chen |
| 2012/0246974 A1 | 10/2012 | Hammerslag et al. |
| 2013/0014359 A1 | 1/2013 | Chen |
| 2013/0025100 A1 | 1/2013 | Ha |
| 2013/0091667 A1 | 4/2013 | Chen |
| 2013/0091674 A1 | 4/2013 | Chen |
| 2013/0092780 A1 | 4/2013 | Soderberg et al. |
| 2013/0012856 A1 | 10/2013 | Hammerslag et al. |
| 2013/0019501 A1 | 10/2013 | Gerber |
| 2013/0269219 A1 | 10/2013 | Burns et al. |
| 2013/0277485 A1 | 10/2013 | Soderberg et al. |
| 2013/0340283 A1 | 12/2013 | Bell et al. |
| 2013/0345612 A1 | 12/2013 | Bannister et al. |
| 2014/0082963 A1 | 3/2014 | Beers |
| 2014/0094728 A1 | 4/2014 | Soderberg et al. |
| 2014/0117140 A1 | 5/2014 | Goodman et al. |
| 2014/0123440 A1 | 5/2014 | Capra et al. |
| 2014/0123449 A1 | 5/2014 | Soderberg et al. |
| 2014/0208550 A1 | 7/2014 | Neiley |
| 2014/0221889 A1 | 8/2014 | Burns et al. |
| 2014/0257156 A1 | 9/2014 | Capra et al. |
| 2014/0290016 A1 | 10/2014 | Lovett et al. |
| 2014/0359981 A1 | 12/2014 | Cotterman et al. |
| 2015/0007422 A1 | 1/2015 | Cavanagh et al. |
| 2015/0014463 A1 | 1/2015 | Converse et al. |
| 2015/0026936 A1 | 1/2015 | Kerns et al. |
| 2015/0033519 A1 | 2/2015 | Hammerslag et al. |
| 2015/0059206 A1 | 3/2015 | Lovett et al. |
| 2015/0076272 A1 | 3/2015 | Trudel et al. |
| 2015/0089779 A1 | 4/2015 | Lawrence et al. |
| 2015/0089835 A1 | 4/2015 | Hammerslag et al. |
| 2015/0101160 A1 | 4/2015 | Soderberg et al. |
| 2015/0150705 A1 | 6/2015 | Capra et al. |
| 2015/0151070 A1 | 6/2015 | Capra et al. |
| 2015/0190262 A1 | 7/2015 | Capra et al. |
| 2015/0223608 A1 | 8/2015 | Capra et al. |
| 2015/0237962 A1 | 8/2015 | Soderberg et al. |

FOREIGN PATENT DOCUMENTS

| | | |
|---|---|---|
| AT | 361808 | 4/1981 |
| CA | 2114387 | 1/1994 |
| CA | 2112789 | 8/1994 |
| CA | 2114387 | 8/1994 |
| CH | 41765 | 9/1907 |
| CH | 111341 | 11/1925 |
| CH | 199766 | 9/1938 |
| CH | 199766 | 11/1938 |
| CH | 204 834 A | 5/1939 |
| CH | 204 834 A | 8/1939 |
| CH | 523 669 | 7/1972 |
| CH | 562 015 | 5/1975 |

(56) References Cited

FOREIGN PATENT DOCUMENTS

| | | |
|---|---|---|
| CH | 577 282 | 7/1976 |
| CH | 612 076 | 7/1979 |
| CH | 537 164 | 7/1981 |
| CH | 624 001 | 7/1981 |
| CH | 471 553 | 12/1984 |
| CN | 2613167 | 4/2004 |
| CN | 201015448 | 2/2008 |
| DE | 555211 | 7/1932 |
| DE | 641976 | 2/1937 |
| DE | 1 661 668 | 8/1953 |
| DE | 7043154 | 11/1970 |
| DE | 1 785 220 | 5/1971 |
| DE | 2 062 795 | 6/1972 |
| DE | 23 41 658 | 3/1974 |
| DE | 24 14 439 | 10/1975 |
| DE | 29 00 077 A1 | 7/1980 |
| DE | 2914280 A1 | 10/1980 |
| DE | 31 01 952 A1 | 9/1982 |
| DE | 36 26 837 | 2/1988 |
| DE | 38 13 470 | 11/1989 |
| DE | 3822113 C2 | 1/1990 |
| DE | 9413147 | 6/1994 |
| DE | 43 02 401 A1 | 8/1994 |
| DE | 43 05 671 A1 | 9/1994 |
| DE | 9308037 | 10/1994 |
| DE | 43 26 049 A1 | 2/1995 |
| DE | 9315776 | 2/1995 |
| DE | 29503552.8 | 4/1995 |
| DE | 196 24 553 | 1/1998 |
| DE | 19945045 A1 | 3/2001 |
| DE | 201 16 755 U1 | 1/2002 |
| DE | 20 2010 000 354 U1 | 6/2010 |
| DE | 11 2013 005 273 T5 | 9/2015 |
| EP | 0 056 953 81 | 6/1969 |
| EP | 0 081 042 81 | 7/1972 |
| EP | 0 056 953 | 8/1982 |
| EP | 0 099 504 | 2/1984 |
| EP | 0 123 050 | 2/1984 |
| EP | 0 123 050 | 10/1984 |
| EP | 0 155 596 | 9/1985 |
| EP | 0 201 051 | 11/1986 |
| EP | 0 099 504 | 1/1987 |
| EP | 0 255 869 | 7/1987 |
| EP | 0 155 596 | 1/1988 |
| EP | 0 255 869 | 2/1988 |
| EP | 0 393 380 | 3/1990 |
| EP | 0 393 380 | 10/1990 |
| EP | 0 474 708 | 9/1993 |
| EP | 0 589 232 A1 | 3/1994 |
| EP | 0 589 233 A1 | 3/1994 |
| EP | 0 614 624 | 9/1994 |
| EP | 0 614 625 A1 | 9/1994 |
| EP | 0 651 954 A1 | 5/1995 |
| EP | 0 679 346 | 11/1995 |
| EP | 0 693 260 B1 | 1/1996 |
| EP | 0 717 942 | 6/1996 |
| EP | 0 858 619 | 8/1996 |
| EP | 0 734 662 A1 | 10/1996 |
| EP | 0 848 917 | 6/1998 |
| EP | 0 858 621 | 8/1998 |
| EP | 0 693 260 B1 | 9/1998 |
| EP | 0 923 965 | 6/1999 |
| EP | 0 937 467 | 8/1999 |
| EP | 0 848 917 81 | 4/2000 |
| EP | 1163860 | 12/2001 |
| EP | 1 219 195 | 7/2002 |
| EP | 1 236 412 | 9/2002 |
| EP | 1 236 412 A | 9/2002 |
| EP | 2298107 B1 | 3/2011 |
| EP | 2359708 | 8/2011 |
| FR | 1 349 832 | 3/1963 |
| FR | 1 404 799 | 7/1964 |
| FR | 1 374 110 | 10/1964 |
| FR | 1 404 799 | 7/1965 |
| FR | 2 019 991 A | 7/1970 |
| FR | 2 019 991 A1 | 7/1970 |
| FR | 2 108 428 | 9/1971 |
| FR | 2 175 684 | 3/1972 |
| FR | 2108429 | 5/1972 |
| FR | 2 173 451 | 10/1973 |
| FR | 2173451 | 10/1973 |
| FR | 2175684 | 10/1973 |
| FR | 2 399 811 | 3/1979 |
| FR | 2 565 795 | 6/1984 |
| FR | 2 598 292 A1 | 11/1987 |
| FR | 2 726 440 A1 | 5/1996 |
| FR | 2 770 379 A1 | 5/1999 |
| FR | 2 814 919 A1 | 4/2002 |
| GB | 189911673 | 7/1899 |
| GB | 216400 | 5/1924 |
| GB | 2 449 722 A | 12/2008 |
| IT | 1220811 | 6/1990 |
| IT | PD 2003 A 000197 | 4/2003 |
| IT | PD 2003 A 000198 | 3/2005 |
| JP | 49-28618 | 3/1974 |
| JP | 51-2776 | 1/1976 |
| JP | 51-121375 | 10/1976 |
| JP | 51-131978 | 10/1976 |
| JP | 53-124987 | 3/1977 |
| JP | 54-108125 | 2/1978 |
| JP | 62-57346 | 4/1987 |
| JP | 63-80736 | 5/1988 |
| JP | H02-236025 | 9/1990 |
| JP | 6-284906 | 10/1994 |
| JP | 7-000208 | 6/1995 |
| JP | 6-284906 | 2/1996 |
| JP | 3031760 | 9/1996 |
| JP | 3030988 | 11/1996 |
| JP | 8308608 | 11/1996 |
| JP | 3031760 | 12/1996 |
| JP | 10-199366 | 7/1998 |
| JP | 2001-197905 | 7/2001 |
| JP | 2004-016732 | 1/2004 |
| JP | 2004-041666 | 2/2004 |
| JP | 2009-504210 | 2/2009 |
| KR | 20-0367882 | 11/2004 |
| KR | 20-0400568 | 8/2005 |
| KR | 20-0400568 | 11/2005 |
| KR | 10-0598627 | 7/2006 |
| KR | 10-0953398 | 4/2010 |
| KR | 10-1025134 B1 | 3/2011 |
| KR | 10-1028468 | 4/2011 |
| KR | 10-1053551 | 7/2011 |
| WO | WO 94/27456 | 12/1994 |
| WO | WO 1995/03720 | 2/1995 |
| WO | WO 95/11602 | 5/1995 |
| WO | WO 98/33408 | 8/1998 |
| WO | WO 98/37782 | 9/1998 |
| WO | WO 99/09850 | 3/1999 |
| WO | WO 99/15043 | 4/1999 |
| WO | WO 099/15043 | 4/1999 |
| WO | WO 99/43231 | 9/1999 |
| WO | WO 00/53045 | 9/2000 |
| WO | WO00/53045 | 9/2000 |
| WO | WO 2000/53045 | 9/2000 |
| WO | WO 2000/76337 A1 | 12/2000 |
| WO | WO 01/08525 | 2/2001 |
| WO | WO 01/15559 | 3/2001 |
| WO | WO 02/051511 | 7/2002 |
| WO | WO 2004/093569 | 11/2004 |
| WO | WO 2005/013748 A1 | 2/2005 |
| WO | WO/2007/016983 | 2/2007 |
| WO | WO 2008/015214 | 2/2008 |
| WO | WO/2008/033963 | 3/2008 |
| WO | WO/2009/134858 | 11/2009 |
| WO | WO 2010/059989 A2 | 5/2010 |
| WO | WO 2012/165803 A2 | 12/2012 |
| WO | WO/2015/035885 | 3/2015 |

(56) References Cited

FOREIGN PATENT DOCUMENTS

| | | |
|---|---|---|
| WO | WO 2015/179332 A1 | 11/2015 |
| WO | WO 2015/181928 A1 | 12/2015 |

OTHER PUBLICATIONS

ASOLO® Boot Brochure Catalog upon information and belief date is as early as Aug. 22, 1997, 12 pages.
La Sportiva, A Technical Lightweight Double Boot for Cold Environments, 1 page. Accessed on May 27, 2015. Retrieved from http://www.sportiva.com/products/footwear/mountain/spantik.
"Strength of materials used to make my Safety Harnesses," Elaine, Inc. Jul. 9, 2012. Retrieved from <https://web.archive.org/web/20120709002720/http://www.childharness.ca/strength_data.html> on Mar. 17, 2014, 2 pages.
International Search Report and Written Opinion for PCT/US2013/032326 dated Jun. 14, 2013, 27 pages.
International Preliminary Report on Patentability for PCT/US2013/032326 dated Sep. 16, 2014, 6 pages.
International Search Report and Written Opinion for PCT/US2013/057637 dated Apr. 7, 2014, 34 pages.
International Preliminary Report on Patentability for PCT/US2013/057637 dated Mar. 3, 2015, 9 pages.
International Search Report and Written Opinion for PCT/US2013/068342 dated Apr. 7, 2014, 29 pages.
International Preliminary Report on Patentability for PCT/US2013/068342 dated May 5, 2015, 9 pages.
International Search Report and Written Opinion for PCT/US2014/014952 dated Apr. 25, 2014, 17 pages.
International Preliminary Report on Patentability for PCT/US2014/014952 dated Aug. 11, 2015, 9 pages.
International Search Report and Written Opinion for PCT/US2014/066212 dated Apr. 22, 2015, 16 pages.
International Search Report and Written Opinion for PCT/US2014/032574 dated Oct. 31, 2014, 19 pages.
International Search Report and Written Opinion for PCT/US2014/045291 dated Nov. 6, 2014, 12 pages.
International Search Report and Written Opinion for PCT/US2014/013458 dated May 19, 2014, 12 pages.
International Preliminary Report on Patentability for PCT/US2014/013458 dated Jul. 28, 2015, 7 pages.
International Search Report and Written Opinion for PCT/US2013/068814 dated Jun. 9, 2014, 18 pages.
International Preliminary Report on Patentability for PCT/US2013/068814 dated May 12, 2015, 12 pages.
Notice of Reasons for Rejection from the Japanese Patent Office dated Feb. 26, 2015 for design application No. 2014-015570, 4 pages.
Receipt of Certificate of Design Registration No. 1529678 from the Japanese Patent Office for design application No. 2014-015570 dated Jun. 26, 2015, 1 page.
International Search Report and Written Opinion for PCT/US2014/055710 dated Jul. 6, 2015, 19 pages.
International Search Report and Written Opinion for PCT/US2014/054420 dated Jul. 6, 2015, 21 pages.
The Preliminary Rejections from the Korean Intellectual Property Office for Application No. 30-2014-34959 received Aug. 7, 2015, is not translated into English. The document requests a renaming of the application to be in accordance with Korean patent law, 5 pages total.
The Preliminary Rejections from the Korean Intellectual Property Office for Application No. 30-2014-34959 received Apr. 7, 2015, is not translated into English. The document requests a revision of the drawings to be in accordance with Korean patent law, 6 pages total.
Certificate of Design Registration No. 30-809409 on Aug. 3, 2015 from the Korean Intellectual Property Office for Appln No. 30-2015-11475, 2 pages.
Certificate of Design Registration No. 30-809410 on Aug. 3, 2015 from the Korean Intellectual Property Office for Appin No. 30-2015-11476, 2 pp.
European Search Report for EP 14168875 dated Oct. 29, 2014, 9 pages.
International Search Report and Written Opinion for PCT/US2014/020894 dated Jun. 20, 2014, 12 pages.
International Preliminary Report on Patentability for PCT/US2014/020894 dated Sep. 8, 2015, 7 pages.
International Search Report and Written Opinion for PCT/US2014/041144 dated Dec. 10, 2014, 13 pages.
International Preliminary Report on Patentability for PCT/US2014/032574 dated Oct. 6, 2015, 12 pages.
International Search Report and Written Opinion for PCT/US2014/046238 dated Nov. 21, 2014, 17 pages.
Office Action received Oct. 8, 2015 from the German Patent and Trademark Office for Appln No. 402015100191.2, regarding the title of the invention, 2 pages.
Anonymous, "Shore durometer," Wikipedia, the free encyclopedia, Mar. 10, 2012, XP002747470, Retrieved from the Internet: URL: https://en.wikipedia.org/w/index.php?title=Shore_durometer&oldid=481128180 [retrieved on Oct. 20, 2015] * shore A, shore D, durometer, polymer, rubber, gel; the whole document *, 6 pages.
Notice of Reasons for Rejection from the Japanese Patent Office dated Oct. 5, 2015 for design application No. 2015-004923, 4 pages.
"Save Tourniquet," 3 pages. Copyright 2015. Accessed on Dec. 11, 2015. Retrieved from http://www.savetourniquet.com/.
ASOLO® Boot Brochure Catalog upon information and belief date is as early as Aug. 22, 1997.
La Sportiva, A Technical Lightweight Double Boot for Cold Environments http://www.sportiva.com/products/footwear/mountain/spantik.
International Search Report and Written Opinion dated Apr. 25, 2014 for International Patent Application No. PCT/US2014/014952 filed Feb. 5, 2014, 17 pages.

* cited by examiner

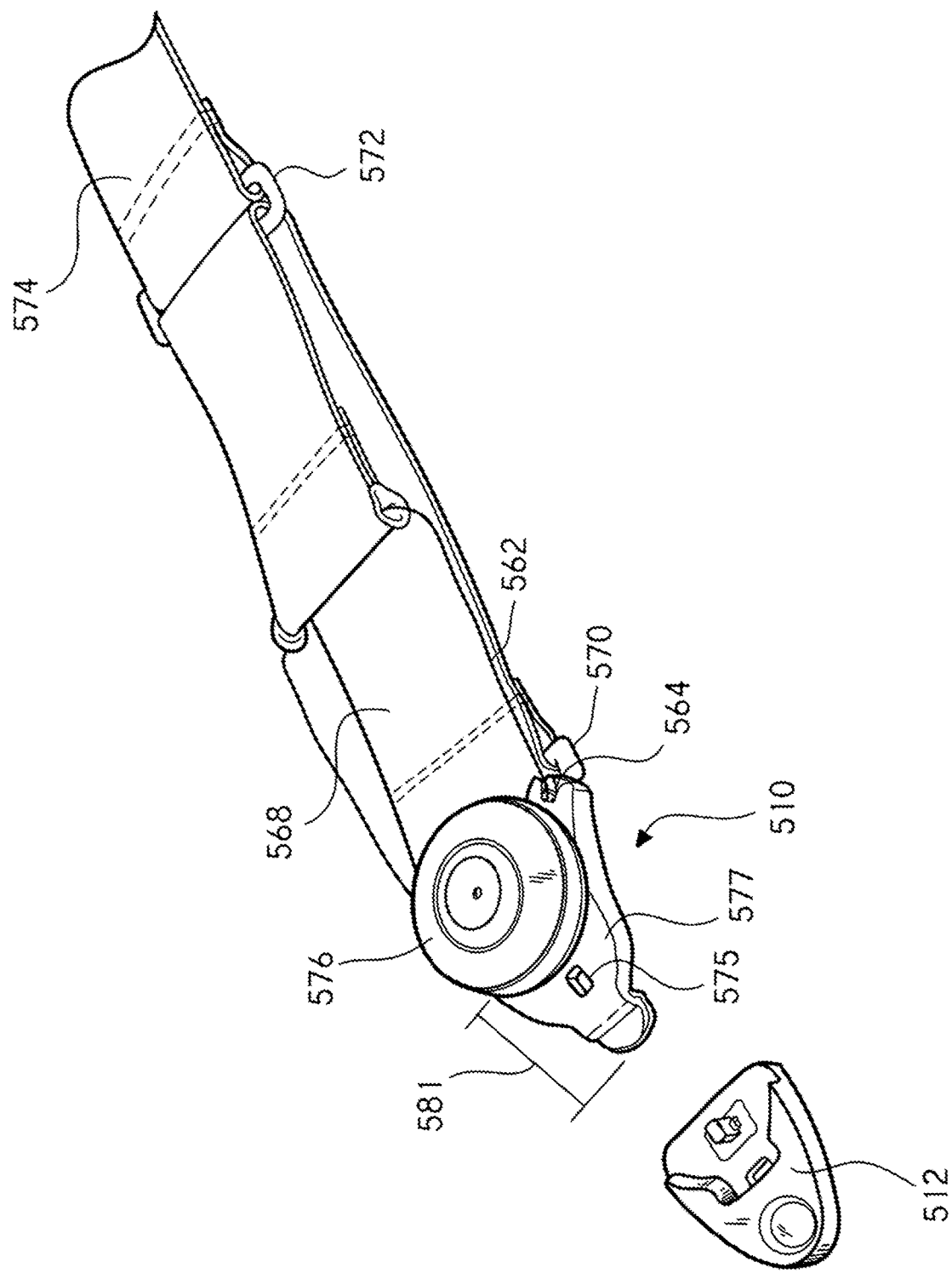

B-B

☐ = 4.4mm × 4.4mm

CLOSURE DEVICES FOR MEDICAL DEVICES AND METHODS

CROSS-REFERENCE TO RELATED APPLICATION

The present application claims priority to pending U.S. Provisional Patent Application Ser. No. 61/761,059, filed on 5 Feb. 2013, entitled CLOSURE DEVICES FOR MEDICAL DEVICES AND METHODS, the entirety of which is hereby incorporated by reference for all intents and purposes.

BACKGROUND

Articles, such as braces and the like, often need to be both closed and tightened. The closure of such articles commonly involves a gross or macro adjustment of the article, while tightening of the article commonly involves a fine tune or micro adjustment of the article. For example, closure of medical braces commonly involves both a coupling of opposing sides of the medical brace about a user's limb (i.e., a macro adjustment) and a subsequent tightening or tensioning of the medical brace about the limb (i.e., a micro adjustment). Different devices and/or components are often employed to provide the macro and micro adjustment of the article. For example, medical braces commonly include a buckle or other fastening component (e.g., Velcro straps, snap buckles, zippers, and the like) that provide the gross or macro closure of the brace. Such braces may also include a micro adjustment device or component (e.g., lace, adjustable straps, and the like) that provides a more fine tune or micro adjustment of the brace. The use of macro and micro adjustment devices or components often require the user to employ both hands in closing and/or tightening the brace. In addition, the macro and micro adjustment devices/components are often positioned remotely from one another about the brace. The positioning and/or use of both hands may be time consuming and/or cumbersome for a user. Additionally, in some instances, the macro adjustment device/component (e.g., buckle or fastening component) may be releasable while the brace is under tension, which may pose a risk to the user and/or otherwise prove inconvenient.

SUMMARY

The present disclosure generally provides closure devices that may be used for various articles, including but not limited to, braces, shoes, boots, accessory bags, such as those from a belt to a user's hip for example, impact protection gear, such as body armor for example, sternum straps on bags and the like, clothing, sporting equipment, outdoor equipment, and etc. Although the closure devices are generally described as being used for various braces, it should be realized that the embodiments described herein may be used for any of the various articles, including those specifically described above.

According to one aspect, a brace that may be tightened or loosened about a limb or bodily segment is provided. The brace includes a brace body having a first side and a second side with a gap extending therebetween, the gap allowing the brace body to be opened for positioning around a limb or bodily segment of a user. The brace further includes a closure component coupled with the first side of the brace body. The closure component includes a coupling member positioned toward a distal end of the closure component, the coupling member being attachable to the second side of the brace body for narrowing the gap and securing the brace body about the user's limb or bodily segment, and an adjustment mechanism that is operable to adjust a tension of the brace body after the brace body is secured to the user's limb or bodily segment and thereby tighten or loosen the brace about the limb or bodily segment.

In some embodiments, the closure component is non-releasable from the attached engagement with the second side while the brace body remains under tension via the adjustment mechanism. Other embodiments are possible. In some embodiments, the coupling member includes a flanged tab that extends from the distal end of the coupling component, and the brace may further include a coupling aperture positioned on the second side of the brace body, the flanged tab being insertable within the coupling aperture for narrowing the gap and securing the brace body about the user's limb or bodily segment. Other embodiments are possible.

In some embodiments, the brace may further include a tension member coupled with the first side of the brace body and operably coupled with the adjustment mechanism, the tension member being tensionable via the adjustment mechanism to tension the brace body about the user's limb or bodily segment. Other embodiments are possible. In some embodiments, the tension member is further slidably coupled with a guide member that is attached to a strap extending from the first side of the brace body, the tension member and the guide member being disposed within a sleeve that spans at least a portion of a gap between the first side of the brace body and a proximal end of the closure component, and wherein tensioning of the tension member causes the guide member to slide within the sleeve. Other embodiments are possible.

In some embodiments, the adjustment mechanism may include a reel mechanism including a housing, a spool positioned within the housing, the spool having a channel around which the tension member is wound, and a knob that is rotatable in a first direction to wind the tension member around the channel of the spool and thereby tension the tension member, and that is further configured to release tension on the tension member. Other embodiments are possible. In some embodiments, the brace may further include at least one guide member positioned on the first side of the brace body or coupled with an extension member extending therefrom, the guide member being configured to direct the tension member about the brace body. Other embodiments are possible. In some embodiments, the brace may include of one of a garment brace, an elbow brace, a knee brace, a sport brace, a medical brace, a back brace, an ankle brace, and a neck brace. Other embodiments are possible, such as any of the various articles described herein and the like.

According to another aspect, a closure component for an article is provided. The closure component includes a body portion having a proximal end that is coupleable with a first side of the article, and a distal end having a coupling component that is coupleable with a second side of the article so as to close a gap between the first side and the second side of the article and thereby secure the article about a limb or bodily segment of a user. The closure component also includes an adjustment mechanism attached to the body portion, the adjustment mechanism being operable to adjust a tension of the article after the article is secured about the user's limb or bodily segment so as to tighten or loosen the article about the user's limb or bodily segment.

In some embodiments, the coupling component includes a flanged tab that is insertable within a coupling aperture positioned on the second side of the article, wherein the coupling component and coupling aperture are non-releasable from a coupled engagement while the article is under tension. Other embodiments are possible. In some embodiments, the proximal end of the closure component's body portion is operably coupled with a tension member that is slidably coupled with at least one guide member positioned on the article's first side or attached to an extension member extending therefrom, the tension member being tensionable via the adjustment mechanism to tension the article about the user's limb or bodily segment. Other embodiments are possible.

In some embodiments, the tension member is disposed within a sleeve that spans a gap between the first side of the article and the proximal end of the closure component's body portion, and wherein tensioning of the tension member causes the tension member to slide within the sleeve. Other embodiments are possible. In some embodiments, the adjustment mechanism includes a reel-based assembly with a housing, a spool positioned within the housing, the spool having a channel around which the tension member is wound, and a knob that is rotatable in a first direction to wind the tension member around the channel of the spool and thereby tension the tension member. Other embodiments are possible. In some embodiments, the closure component has a particular volume selected from a volume within the range of about 6000 cubic millimeters to about 12000 cubic millimeters.

According to another aspect, a method for adjusting a tightness of an article about a limb or bodily segment of a user is provided. The method includes positioning the article over the limb or bodily segment, where the article includes an article body having a first side, a second side, and a gap therebetween, and a closure component coupled with and offset from the first side of the article body. The closure component includes a coupling member positioned toward a distal end of the closure component, an adjustment mechanism that is operable to tension the article body after the article body is secured to the user's limb or bodily segment. The method also includes attaching the coupling member with the second side of the article body to close the gap and secure the article about the user's limb or bodily segment, and operating the adjustment mechanism to adjust a tension of the article body and thereby tighten the article about the limb or bodily segment.

In some embodiments, the steps of attaching the coupling member and operating the adjustment mechanism are performed with a single hand. Other embodiments are possible. In some embodiments, attaching the coupling member includes inserting a flanged tab within a coupling aperture positioned on the second side of the article body, and the flanged tab and coupling aperture are non-releasable from a coupled engagement while the article remains under tension. Other embodiments are possible. In some embodiments, a tension member is operably coupled with the adjustment mechanism and with the first side of the article body, the tension member being tensionable via operation of the adjustment mechanism to tension the article body. In some embodiments, operating the adjustment mechanism includes rotating a knob of a reel mechanism in a first direction to wind the tension member around a channel of a spool that is positioned within a housing of the reel mechanism, where winding of the tension member around the spool's channel tensions the tension member. Other embodiments are possible.

In some embodiments, the tension member is slidably coupled with a guide member, the tension member and guide member being disposed within a sleeve that spans a gap between the first side of the article body and a proximal end of the closure component, and tensioning of the tension member causes the guide member to slide within the sleeve. Other embodiments are possible. In some embodiments, the method further includes locking or securing the adjustment mechanism after the article body is tensioned to impede further operation of the adjustment mechanism. Other embodiments are possible. In some embodiments, the method further includes releasing a tension of the tension member via the adjustment mechanism, and detaching the coupling member from the second side of the article body to allow the article to be removed from the user's limb or bodily segment. Other embodiments are possible.

According to another aspect, a closure component for a brace is provided. The closure component includes a body portion having a lateral width and a longitudinal length that is greater than the lateral width, the body portion includes a proximal end that is coupleable with a first side of the brace via at least two tension member segments spaced longitudinally apart that extend laterally from the proximal end of the body portion toward the first side of the brace, and a distal end having a coupling member that is coupleable with a second side of the brace so as to close a gap extending laterally between the first side and the second side of the brace and thereby secure the brace about a limb or bodily segment of a user. The closure component further includes an adjustment mechanism attached to the body portion, the adjustment mechanism being operable to tension the at least two tension member segments after the brace is secured about the user's limb or bodily segment so as to tighten or loosen the brace about the user's limb or bodily segment.

In some embodiments, the body portion includes at least two coupling members spaced longitudinally apart that are coupleable with the second side of the brace to close the gap and secure the brace about the user's limb or bodily segment. Other embodiments are possible. In some embodiments, each coupling member includes a flanged tab that is insertable within a coupling aperture positioned on the second side of the brace. Other embodiments are possible. In some embodiments, the at least two tension members include lace, and wherein the closure component's body portion further includes a channel or lumen within which the lace is slidably disposed between laterally separated tension members segments, wherein the channel or lumen allows the lace to dynamically shift or adjust between the laterally separated tension members segments such that the brace is dynamically adjustable about the limb or bodily segment as the limb or bodily segment flexes or otherwise changes shape. Other embodiments are possible.

In some embodiments, the longitudinal length of the body portion is adjustable so as to accommodate varying sized braces and/or limb or bodily segments of a user. Other embodiments are possible. In some embodiments, the body portion further includes two panel segments that are adjustable longitudinally relative to one another so as to vary the longitudinal length of the body portion, and wherein each tension member is coupled with both panel segments such that a tensioning width of each tension member is adjustable via longitudinal adjustment of the two panel segments. Other embodiments are possible. In some embodiments, the body portion further includes a coupling port that releasably attaches the adjustment mechanism with the body portion such that the adjustment mechanism is removable from the body portion. Other embodiments are possible. In some embodiments, the at least two tension member segments are formed from a single lace or are formed from one or more laces. Other embodiments are possible.

According to another aspect, a method of adjusting a tightness of a brace about a limb or bodily segment of a user is provided. The method includes positioning the brace over the limb or bodily segment, where the brace includes a brace body having a first side, a second side, and a gap therebetween, and a closure component coupled with and offset from the first side of the brace body, the closure component includes a proximal end including at least two tension members spaced longitudinally apart and extending laterally from the proximal end of the body portion toward the first side of the brace, a distal end including a coupling member that is coupleable with a second side of the brace so as to close a gap extending laterally between the first side and the second side of the brace, and an adjustment mechanism attached to the body portion and operable to tension the at least two tension members after the brace is secured about the user's limb or bodily segment. The method further includes attaching the coupling member with the second side of the brace body to close the gap and secure the brace about the user's limb or bodily segment, and operating the adjustment mechanism to adjust a tension of the at least two tension members and thereby tighten or loosen the brace about the limb or bodily segment.

In some embodiments, the body portion includes at least two coupling members spaced longitudinally apart that are coupleable with the second side of the brace to close the gap and secure the brace about the user's limb or bodily segment. Other embodiments are possible. In some embodiments, each coupling member includes a flanged tab, and wherein the method further includes inserting each flanged tab within a coupling aperture positioned on the second side of the brace. Other embodiments are possible. In some embodiments, the method further includes adjusting the longitudinal length of the body portion so as to accommodate a different sized brace and/or the user's limb or bodily segment.

In some embodiments, adjusting the longitudinal length of the body portion includes repositioning two panel segments relative to one another, and each tension member is coupled with both panel segments such that a tensioning width of each tension member is adjusted via repositioning of the two panel segments. Other embodiments are possible. In some embodiments, the method further includes attaching the adjustment mechanism with a coupling port of the body portion to releasably couple the adjustment mechanism with the body portion. In some embodiments, the method further includes releasing a tension of the at least two tension members via the adjustment mechanism, and detaching the coupling member from the second side of the brace body to allow the brace to be removed from the user's limb or bodily segment. Other embodiments are possible.

Although not so limited, an appreciation of the various aspects of the present disclosure along with associated benefits and/or advantages may be gained from the following discussion in connection with the drawings.

BRIEF DESCRIPTION OF THE DRAWINGS

FIGS. 5E-F illustrate a second closure system or device.

Figure 1:
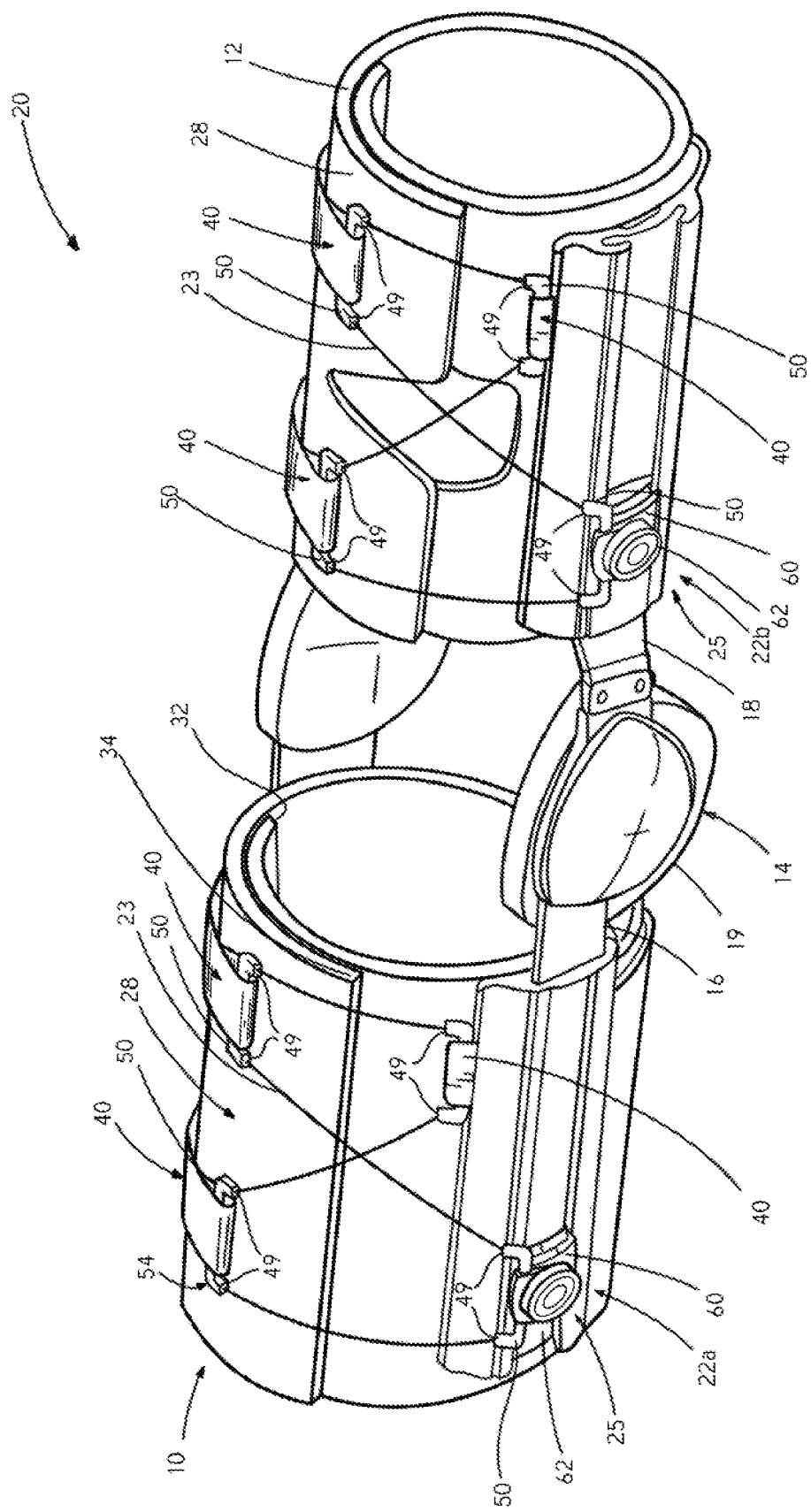
FIG. 1 illustrates an example knee brace.

In the appended figures, similar components and/or features may have the same numerical reference label. Further, various components of the same type may be distinguished by following the reference label by a letter that distinguishes among the similar components and/or features. If only the first numerical reference label is used in the specification, the description is applicable to any one of the similar components and/or features having the same first numerical reference label irrespective of the letter suffix.

DETAILED DESCRIPTION

Embodiments described herein provide various closure devices that may be used with braces, footwear, hats, gloves, or various other apparel or devices to open and close the same to allow an individual to don/doff the apparel or device. Some closure devices may include several components or pieces. For example, some closure devices may include Velcro® straps or panels that are fit around a body part to provide gross- or macro-closure. These devices may also include additional smaller straps that the individual can adjust to provide an additional, fine-tuned, closure force. Further, tightening devices and lace systems (e.g., reel and lace systems) may be incorporated into braces and other medical devices using various closure methods. For example, some braces having straps or panels that are modified to include a reel and lace system. The braces may be closed using straps/panels and then the reel device may be operated to fine tune closure of the brace.

In many cases, an individual may be required to use two hands in donning and doffing these braces and/or in tightening these braces; and/or the individual may be required to perform multiple tasks at varying locations on the brace to fully close and tighten the brace. Embodiments described herein provide closure devices that simplify brace closure processes (e.g., donning and doffing of the brace) in addition to simplifying the brace closure and tightening process. In some embodiments, this is achieved by integrating the releasing and tightening mechanisms into a single component. This integrated component provides a simple user interface. In such an embodiment, the tightening mechanism may comprise a reel that may function as a handle that allows an individual to wrap the brace around body part, couple the brace about the body part, and then easily tension or tighten the brace with a single hand.

Accordingly, it will be appreciated that the closure device embodiments described herein provide at least the following benefits: simplifying donning and doffing of a brace, medical device, apparel, and the like; creating a single point of interface for the user in donning, doffing, and adjusting the brace; providing the control of a single strap, such as to create varying zonal pressures, or controlling multiple straps; integrating multiple components into a single component, thereby reducing brace complexity; and the like. Having described some features of the embodiments generally, additional features will be apparent with reference to the figures described herein below.

For convenience, the disclosure will focus mainly on braces, although it should be realized that the embodiments described herein, for example the closure device and/or other devices, may be used with virtually any type of apparel, garment, or other structure. For example, the closure and/or other devices described herein may be used on shoes, boots, gloves, hats, medical devices, and the like. In addition, the disclosure generally describes the devices, or components thereof, being closed via a reel or dial mechanism. The reel or dial mechanism typically closes the device, or components thereof, by tensioning a lace. As described herein, the dial is typically twisted or rotated to wind a lace into a spool. The disclosure generally describes using reels and dials for convenience in describing the various embodiments. As such, although the disclosure generally describes the closure devices, or components thereof, using a reel or dial mechanism, it should be realized that any tightening mechanism may be used and the disclosure is not limited to embodiments that only use a reel or dial.

Braces and other articles are typically designed to wrap around a body part and thus must be opened and closed over the body part. The closure embodiments or mechanisms described herein are placed on a brace to allow an individual, such as a patient, to quickly and easily wrap and close the brace around a particular body part. For example, referring now to FIG. 1, illustrated is an embodiment of an orthopedic knee brace 20. The brace 20 generally comprises a knee brace that may be tightened around a leg such that the knee brace substantially surrounds and protects a wearer's knee. The brace 20 may be tightened using a lacing configuration comprising two lacing systems 22a, 22b (collectively, lacing system 22). Although the illustrated embodiment shows the lacing systems applied to knee braces, it will be understood that aspects of the present disclosure are applicable to any of a variety of braces, including ankle braces, wrist braces, foot braces, elbow braces and many other types of braces, orthopedic or otherwise.

In some embodiments, the lacing configuration of the closure system comprises two distinct lacing systems 22a, 22b. Each lacing system 22 may comprise a lace or cable 23 that is threaded through portions of the brace 20 and attached at opposite ends to a tightening mechanism or reel 25, which includes a control such as a lever, crank or knob, that may be manipulated to retract the lace 23. In addition, the tightening mechanism 25 may comprise a mechanism of release, such as a button or lever, for disengaging the tightening mechanism 25, to permit the lace 23 to be loosened and/or freely withdrawn. In some embodiments, the tightening mechanism 25 may be pulled in a generally upward director to permit an internal spool to spin and the lace 23 to be pulled freely. Additionally, the tightening mechanism 25 may be unwound (e.g., counter-clockwise) to release the spool and allow the lace 23 to be pulled, or to unwind the lace 23. As shown in FIG. 1, the lace 23 may be threaded in a cross-pattern along a generally forward-facing portion of the brace 20, between two generally parallel rows of side retaining members or straps 40. In another embodiment, the lace 23 may be threaded or run horizontally across the brace 20. The straps 40 may consist of a strip of material attached to the brace 20 so as to define a space in which guides 50 are positioned. In this example, the lace 23 slides through the guides 50 during tightening/loosening of the lace 23. A more thorough or complete description of the brace 20 and lacing systems 22a, 22b is provided in U.S. Pat. No. 8,277,401, the entire disclosure of which is hereby incorporated by reference.

The brace 20 shown in FIG. 1 is constructed to fit a limb such as a leg. For example, an upper cuff 10 may be formed to fit and curve around a thigh, generally conforming to the wearer's musculature. A lower cuff 12 is similar in construction to the upper cuff 10, and may be formed to fit and curve around a calf. In some embodiments, upper and lower cuffs 10, 12 are formed from a relatively lightweight, breathable material. In some embodiments, cuffs 10, 12 are manufactured from a cloth, fabric, or foam-like material, or a thermoformable or non-thermoformable plastic material. Other embodiments are possible.

As shown, each of the cuffs 10, 12 are generally formed from a single piece of material that is wrapped around itself, forming two ends 32, 34 that are drawn towards each other and overlap. Although the ends 32, 34 are shown in an overlapping position, it will be appreciated that the ends 32, 34 may also be sized to be separated by some distance when the brace 20 is tightened. Generally, the lace 23 may be tensioned to draw the ends 32, 34 past each other and thereby tighten the brace 20 about the wearer's limb. As may be understood, the two ends 32, 34 of the brace 20 may be opened and fit about a patient's leg, and then the two ends 32, 34 may be positioned to a limb and the brace 20 may be tightened as described above.

Figure 2:
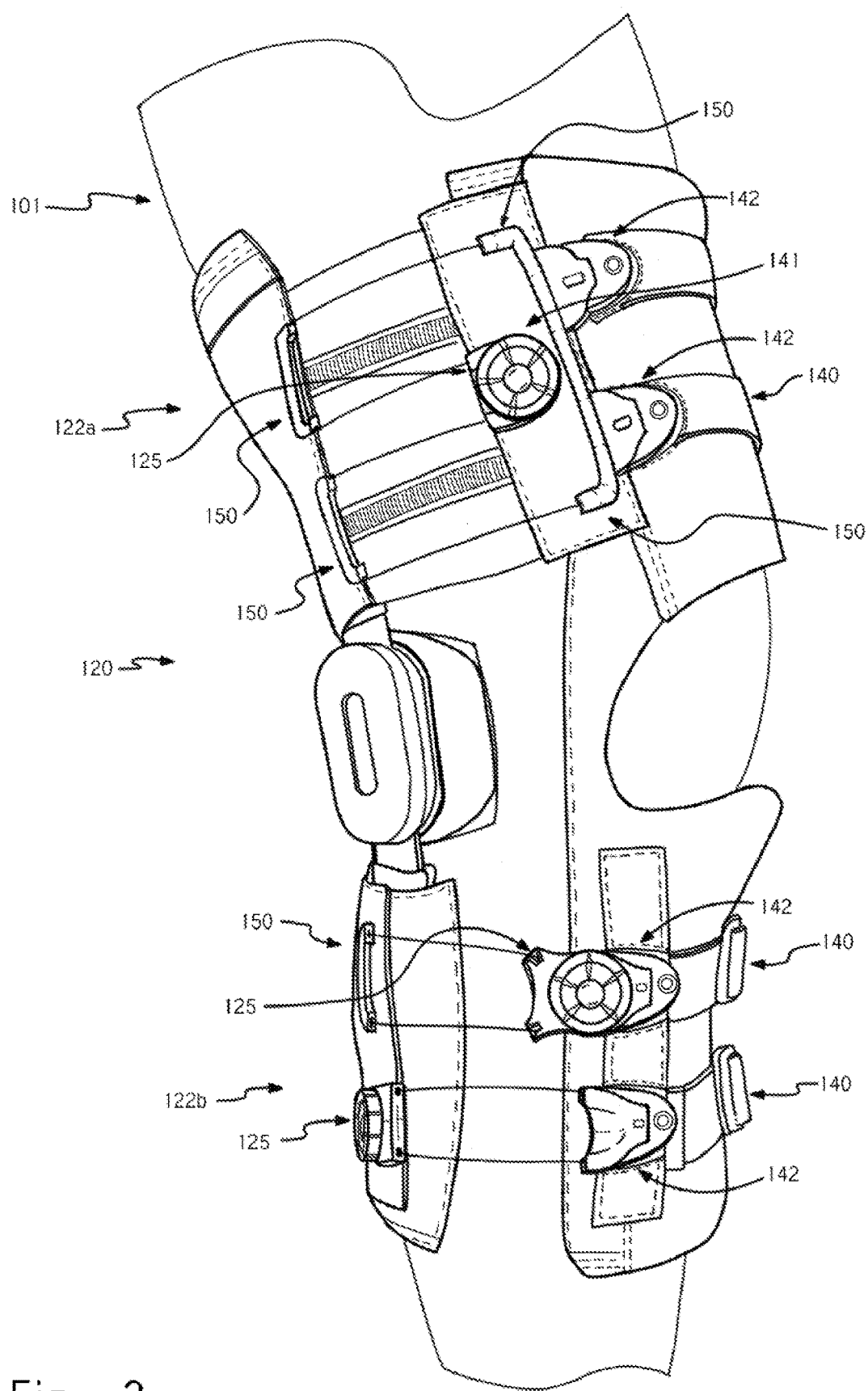
FIG. 2 illustrates another example knee brace when tightly fitted to a limb.
Figure 3:
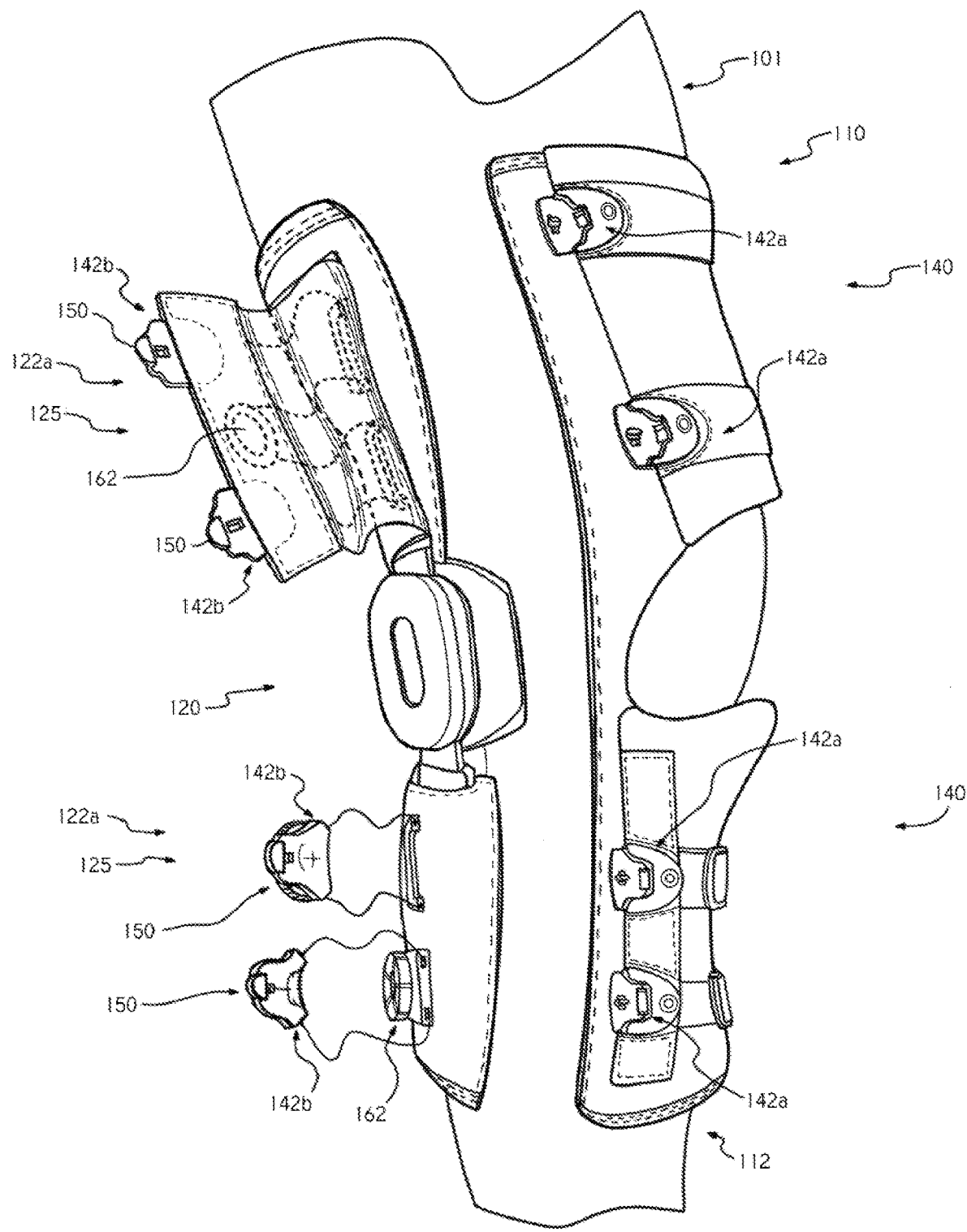
FIG. 3 illustrates the knee brace of FIG. 2 when loosely fitted to a limb.

FIGS. 2-3 illustrate another brace 120 being fit over a leg 101. In this example, the brace 120 includes a closure system 101 (e.g., elements 122a-b) that is described in more detail in U.S. Pat. No. 8,277,401, the entirety of which is hereby incorporated by reference. The brace 120 includes a rough adjustment feature that permits opening of the brace 120 to facilitate attachment of the brace 120 about the leg 101, while providing a tightening mechanism 125 for fine tune or micro tightening. In some embodiments, the rough adjustment feature may comprise variable length retaining members 140 that allow the brace 120 to fit a wider variety of wearers' legs, such as in a "one size fits all" implementation. In one embodiment, the variable length retaining members 140 include adjustable straps. In other embodiments, a panel 141, such as those described herein, may be used. In this example, the panel 141 may be coupled with the tightening mechanism 125, such as a reel mechanism and lace, to provide gross or macro-adjustment of the brace 120. In some embodiments, a quick release mechanism 142 may be employed to allow for convenient donning and doffing of the brace.

As shown in greater detail in FIG. 3, each quick release mechanism 142 may include or comprise a female component 142a and a male component 142b that may be coupled together to close the brace about the leg 101 and thereby allow the brace 120 to be conveniently donned and doffed. Various example embodiments of female and male components 142a, 142b are described herein. In some embodiments, a female component 142a may be coupled with one side of a brace or article while a male component 142b is attached to a panel member 141 as described herein, though the arrangement of components may be switched or otherwise defined as needed. In some embodiments, the female component 142a may be coupled with an end of a retaining member 140 while an opposite end of the retaining member 140 is attached to the brace 120. Tensioning the lacing or closure system 122 may cause tension on the retaining member 140 when the quick release mechanism 142 is engaged, thereby compressing cuffs 110, 112 around the leg 101.

In some embodiments, the panel 141 may include two or more male components 142b that couple with corresponding females components 142a positioned on an opposing side of the brace 120. The panel 141 may include two tension member segments (e.g., separate lace and/or straps segments) that span a gap between the opposing sides of the brace 120. In other embodiments, a male component 142b may be coupled with a lace and/or strap that spans a gap between opposing sides of the brace 120. A benefit of the panel 141 configuration is that a single tightening mechanism 125 may be used to tension a greater lateral length of the brace 120. A benefit of the singe male component 142b and lace/strap configuration is that individual segments of the brace 120 may be differentially tensioned or tightened. As shown in FIGS. 2-3, in some embodiments the brace 120 may include a combination of a panel 141 configuration and a single male component 142b and lace/strap configuration as desired. In some embodiments, the brace 120 may include two retaining members 140, although in other embodiments, the number of retaining members 140 may vary. In some embodiments, three, four, five, six or more retaining members 140 may be desirable, or the brace 120 may not include any retaining members 140. Other embodiments are possible.

FIG. 3 shows one embodiment of the brace 120 in a partially open configuration. In this example, the quick release mechanism 142 (i.e., male component 142b and female component 142a) is disconnected leaving the female component 142a attached to a side of the brace 120 and releasing the panel 141 and/or male component 142b. To remove the brace 120, cuffs 110, 112 may be opened and the brace 120 may be slid from or otherwise removed from the leg 101. Prior to release of the quick release mechanism 142, tension may be released in the closure system 122 by, for example, pulling outwards on knobs 162 to release the tightening mechanism 125 of both cuffs 110, 112.

Figure 4A:
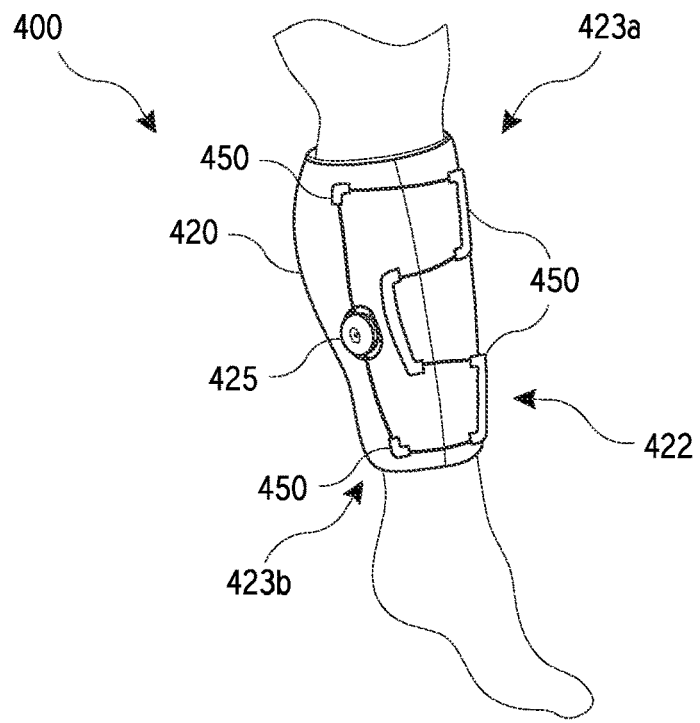
FIG. 4A-C illustrates still another example knee brace when tightly fitted to a limb.
Figure 4B:
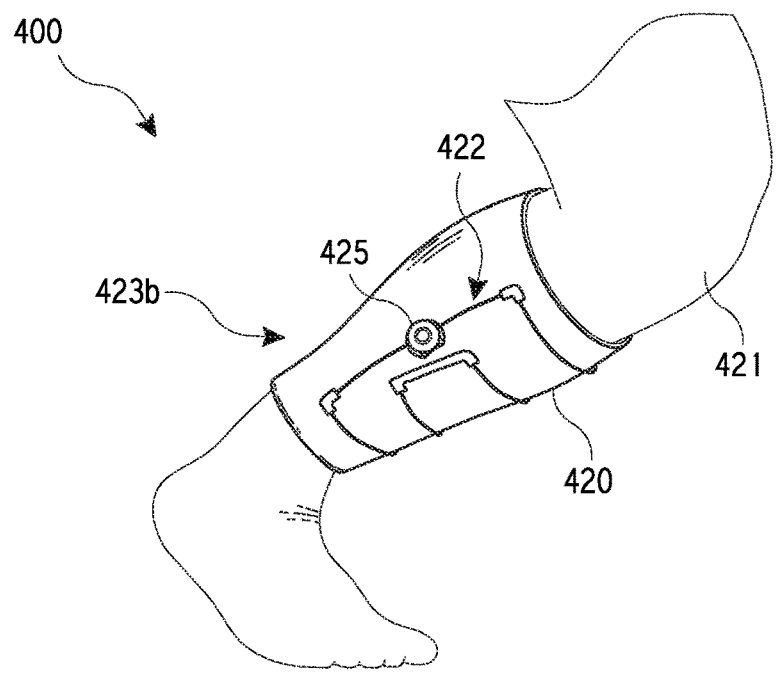
Figure 4C:
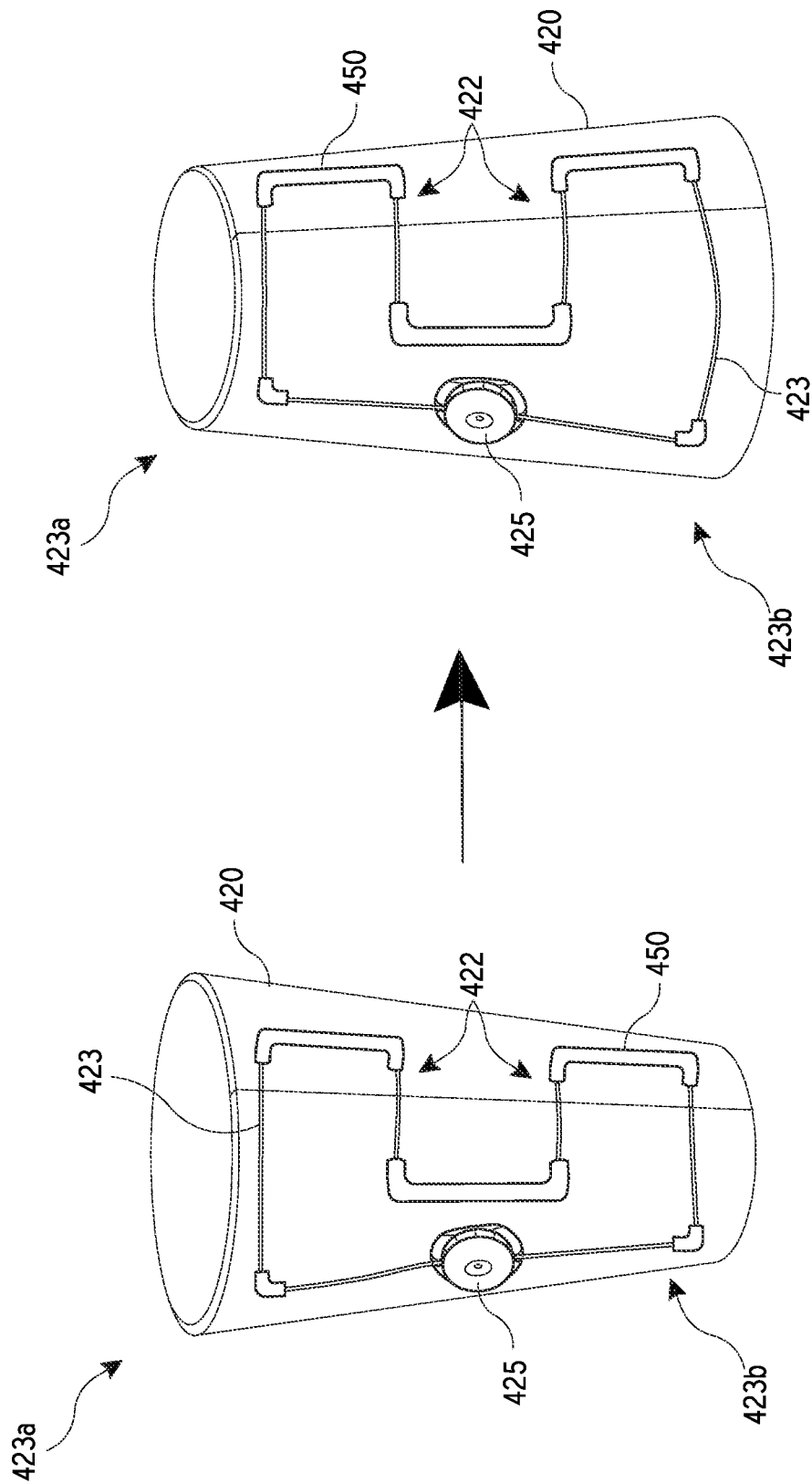

Referring now to FIGS. 4A-C, another example brace 400 is shown in accordance with the present disclosure. One advantage of using the brace 400, which is also applicable to other braces of the present disclosure, is the increased ability of the brace 400 to fit a conical shape or an adjusting shape of a limb, such as a leg 421, arm, or any other body part. The ability of the brace 400 to fit a conical shape is provided by a closure system 422. As the brace 400 is fit about the leg 421, for example, and lace 423 is tensioned or wound via reel mechanism 425, an upper portion 423a of the brace 400 contacts the leg 421 (i.e., conical-shaped object). As the lace 423 is wound, the lace 423 adjusts until a lower portion 423b of brace 400 also contacts the leg 421. Additional winding of the lace 423 will result in an approximately equal tension throughout the lace 423, which provides a relative even pressure on the leg 421. As such, the brace 400 is well-fit to accommodate the conical shape of the leg 421.

Similarly, the brace 400 is able to adjust to changes in the shape of the leg 421 (or other body part), due to flexing and/or relaxing of muscle. For example, as the leg 421 is flexed and assumes a more cylindrical shape, the lace 423 is able to slide within, or relative to, guides 450 so that the lower portion 423b of the brace 420 opens or widens as the top portion 423a contracts or shrinks Conventional braces typically do not adjust in this manner and as such, when the leg 421 (or other body part) is flexed, such braces may typically be forced to move or migrate about the body, such as downward against the knee or ankle. In the embodiments described herein, because the lace 423 is able to slide relative to the brace 400 and the guides 450, and the brace 400 is able to adjust to changes in shape, the fit or hold of the brace 400 about a particular body part is increased and migration of the brace 400 is limited or eliminated.

As mentioned previously, the use of buckles, Velcro®, or other similar mechanisms often require the user to use both hands in opening and/or closing of a typical brace. For example, to couple the male and female components of a buckle, the user is often required to grasp the female component with one hand while the male component is being inserted into the female component so as to ensure that the female component will stay relatively in place. Similarly, in closing Velcro® straps, the user often must thread a distal end of the strap through a d-ring or hook before tensioning the strap and folding it back on itself. The user often must hold the d-ring or hook while the strap is being threaded therethrough. Requiring the use of both hands is often inconvenient, frustrating, and/or annoying to the user, and potentially not an option for dexterity compromised or handicapped individuals. Likewise, donning and doffing the brace in this manner may be needlessly time consuming.

The use of buckles, Velcro®, or other similar mechanisms also allows the brace to be uncoupled while tension is still applied by the lace winding system described above. For example, the user can use buckles or Velcro® straps to roughly fit the brace about the leg and then use the closure or tightening system described herein to fine tune the fit of the brace about the leg. Without releasing tension in the lace, the user may then unbuckle or unstrap the brace to take the brace off or adjust the brace. Upon refitting the brace about the leg, the user may again use the buckles or straps to roughly fit the brace on the leg and then fine tune the fit with the closure or tightening system. If tension is not released in the lace before each removal of the brace, however, the lace will be continually wound into the tightening mechanism (e.g., the spool of the reel mechanism) resulting in increasingly shorter amounts of lace for use and possible over storage of the lace within the tightening mechanism. Further, tightening of the brace may not be possible if too much of the lace is wound into the tightening mechanism.

As briefly described above, embodiments of the present disclosure integrate components of closure devices into a single component, mechanism, or device that provides various advantages over conventional devices, such as being easier to use, reducing component count, simplifying the brace, and the like. According to one embodiment, the components of the brace may be integrated with a coupling system or device that may include a "reel panel assembly" or "reel panel" or "panel" that allows the user to close and tension the brace (i.e., tighten and loosen the brace). The term "panel" or "reel panel" as used herein includes virtually any component that other components or pieces may be attached to. The panels described herein are often generally flat so that the panel may lay flat against the brace, but the panels are not limited to such configurations and, indeed, may be contoured into other shapes as desired. The panels also typically have a top surface that the integrated components, such as the reel mechanism, attach to or couple with. The panels and/or components coupled with or integrated thereto may be made of plastic, metal, fabric, and the like, or any combination thereof. Further, in some embodiments, the panels may be variable in length and/or include one or more modular or removable components.

Figure 5A:
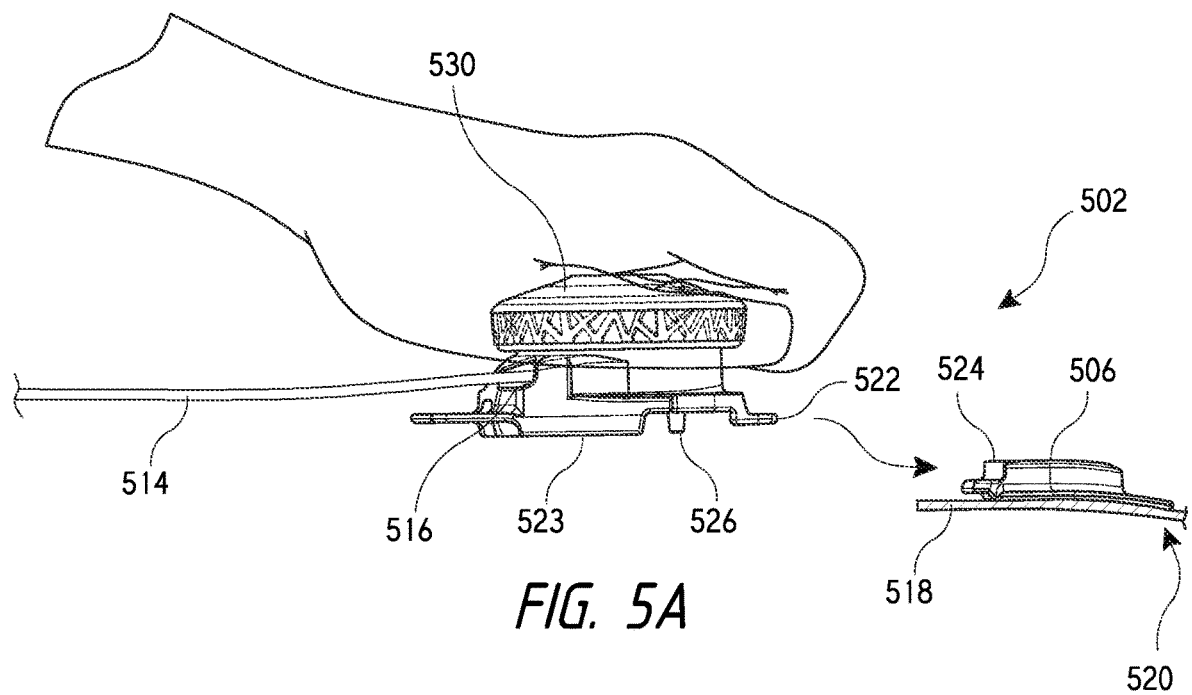
FIGS. 5A-D and FIGS. 5G-H illustrate a first closure system or device.
Figure 5B:
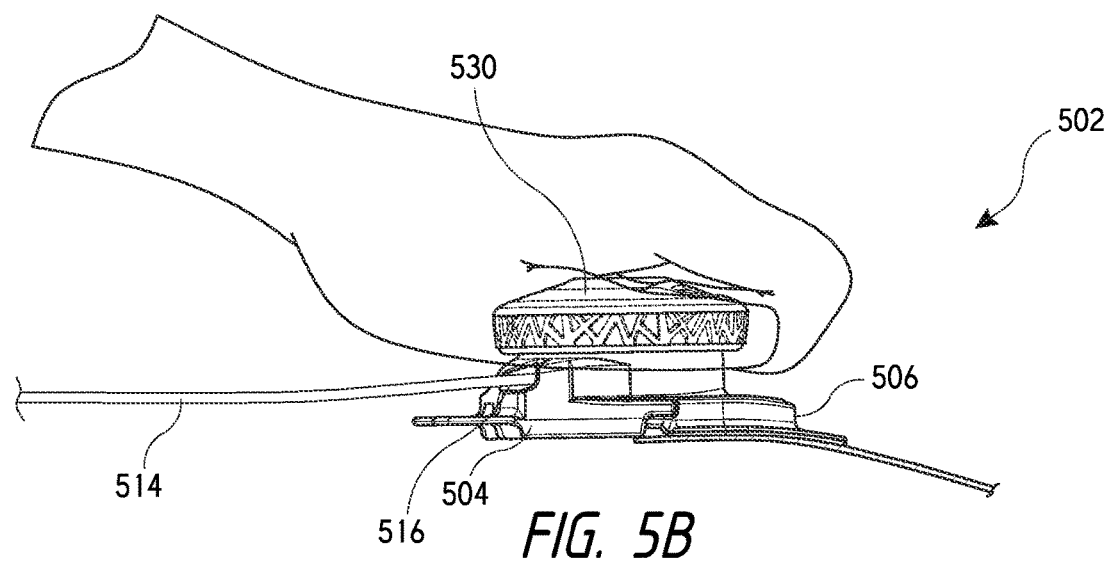
Figure 5C:
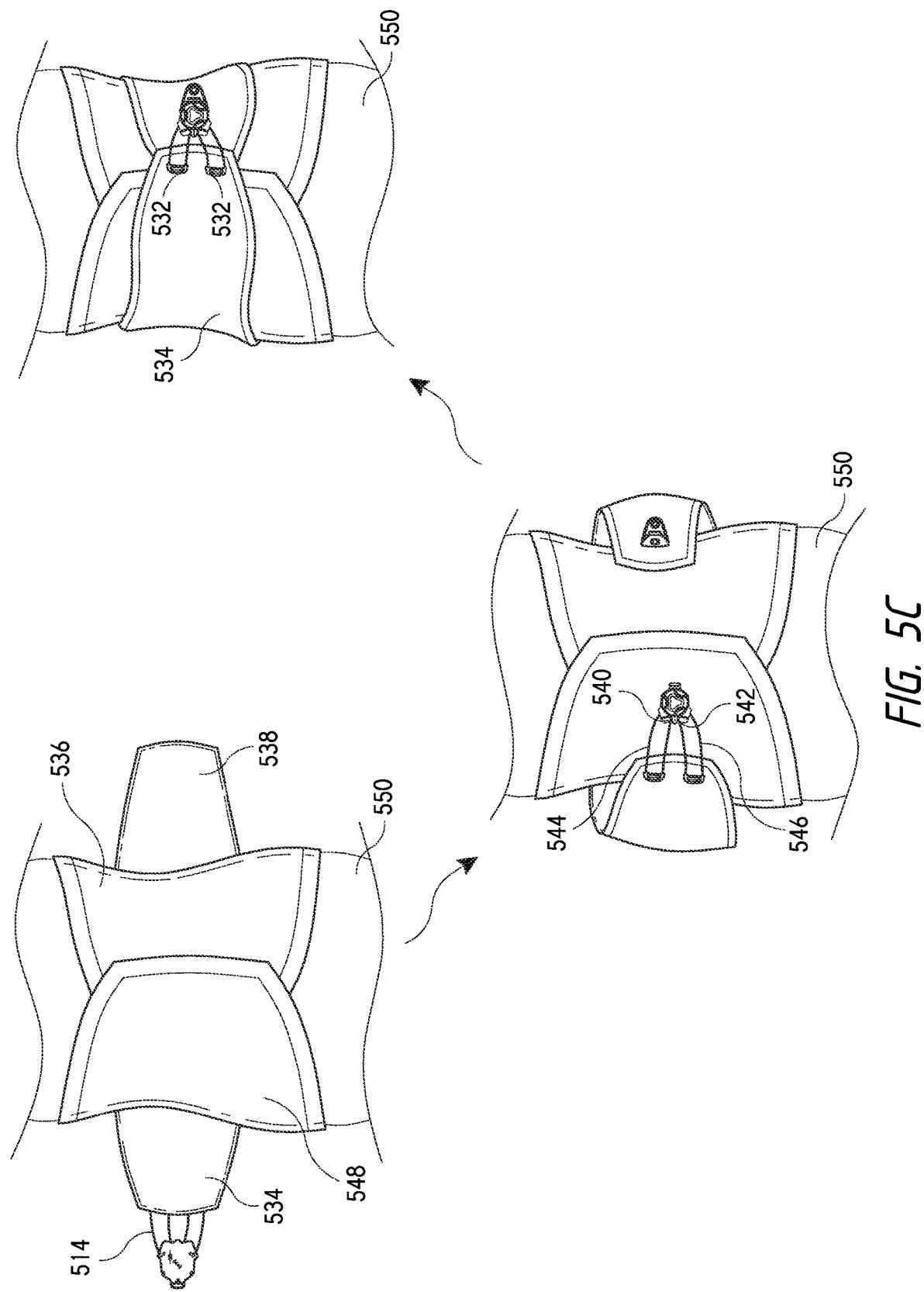
Figure 5D:
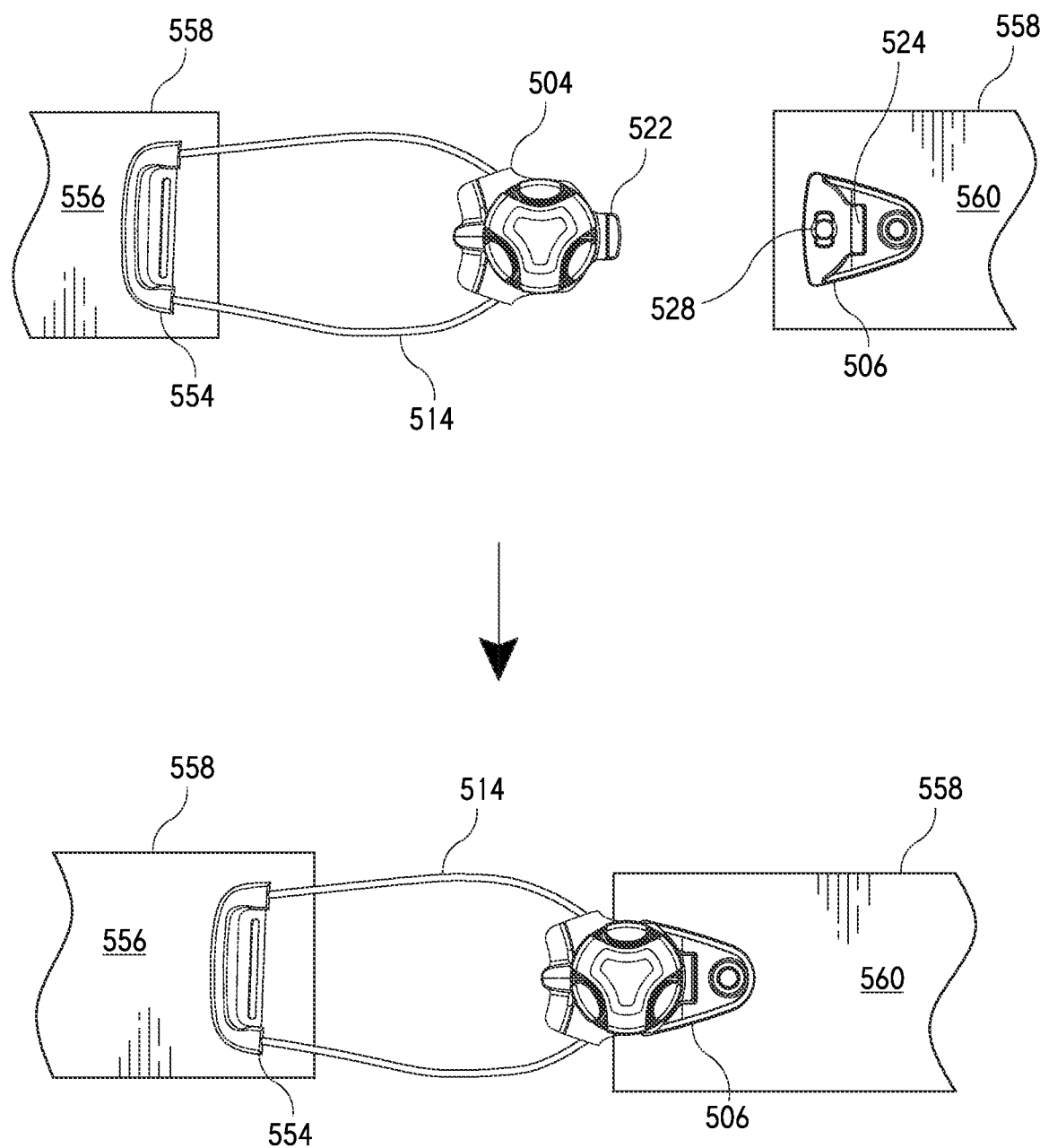

Referring now to FIGS. 5A-H, various embodiments of a closure system or device are shown arranged and configured in a manner consistent with the present disclosure. FIGS. 5A-D and FIGS. 5G-H in particular illustrate a first closure device 502 that generally comprises a male component 504 and a female component 506, and FIGS. 5C-D illustrate a second closure device 508 that too generally comprises a male component 510 and a female component 512. Details associated with the configuration and coupling of respective components of one or more of the first and second closure device 502, 508 are described further below. Additional details associated with the configuration and coupling of one or more of the first and second closure device 502, 508 are provided in U.S. Nonprovisional patent application Ser. No. 14/071,432, filed 4 Nov. 2013, the entirety of which is hereby incorporated by reference.

Referring specifically to FIGS. 5A-B, a sequence is illustrated whereby the male component 504 of the first closure device 502 is coupled to or with the female component 506 of the first closure device 502. In this example, a tension member (hereinafter lace 514) is generally threaded to a lumen or passage 516 of the male component 504, and the female component 506 is generally coupled to an end 518 of a brace 520. Although not shown, the lace 514 is further generally coupled to another end of the brace 520. In use, a step-shaped flange or tab 522 of the male component 504 is brought into engagement with a complementary step-shaped recess 524 of the female component 506 to couple the male component 504 with the female component 506. During this process, the male component 504 may be pushed downward into the female component 506 so that a pair of tabs 526 of the male component 504 engage with a grooved post 528 (see also, FIG. 5D) of the female component 506. The tabs 526 may "snap" into engagement with the grooved post 528 to produce audible feedback during coupling of the components. The tabs 526 may also provide tactile feedback so that when coupling of the components has occurred, a user may be able to tactually recognize when coupling occurs.

Following initial coupling of the male component 504 with the female component 506, a dial or reel mechanism 530 of the male component 504 may be rotated or adjusted as desired to fine tune a tension applied to the lace 514. In this example, the lace 514 is wrapped to internal spool (not shown) of the male component 504, so that when the reel 530 is rotated, the ends of the brace 520 may be pulled together to tighten the brace 520 around a limb as desired. As the lace 514 is tensioned, the lace 514 may tend to pull the male component 504 from the female component 506 in opposing directions so that various internal surfaces of the male component 504 and the female component 506 are pressed or biased together, as discussed in further detail below in connection with at least FIG. 8B and FIG. 13. This may beneficially make it difficult to release or decouple the male component 504 from the female component 506 without releasing tension on the lace 514 using the reel mechanism 530. The arrangement of the components of the closure device 502 allow the above closure and tightening process to be performed with a single hand.

It is contemplated that the male and female components of the various closure devices of the present disclosure may be coupled to a particular brace in many different types of configuration or arrangements. For example, as shown in FIG. 5C, lace 514 is threaded to the male component 504 of the first closure device 502 and also to guide members 532 that are coupled to a first panel 534 of a brace 536. In this example, the female component 506 of the first closure device 502 is generally coupled to a second panel 538 of the brace 536. In some embodiments, the lace 514 may be formed of a single segment, that is, the lace 514 may be formed of a single piece of lacing having a particular length. In this embodiment, the lace 514 may be threaded from the reel mechanism of male component 504, around guides 532, and further around a guide (not numbered) positioned on male component 504 centrally of the two ends of lace 514. In other embodiments, the lace 514 may be formed of two segments, that is, lace 514 may be formed of a first piece 544 of lacing having a particular length and second piece 546 of lacing having a particular length. In this example, an end of first piece 544 may be fixedly coupled to the male component at termination 540, while an end of second piece 546 is fixedly coupled to the male component at termination 542.

To couple the brace about a limb or bodily segment, the tab 522 of the male component 504 may be brought into engagement with the recess 524 of the female component 506 to couple the male component 504 with female component 506. The dial or reel mechanism 530 of the male component 504 may then be adjusted or rotated in a clockwise direction, for example, as desired to apply tension to the lace 514 to pull together the first panel 534 and the second panel 538 and tighten the brace 536 by fine adjustment. The reel mechanism 530 may also be adjusted or rotated in a counterclockwise direction for example as desired to release tension to the lace 514 to allow the brace 536 to loosen, or a knob of the reel mechanism 530 may be moved axially upward to release tension on the lace. In other embodiments, a button, lever, or other tension release mechanism may be used to release tension on the lace.

In the example of FIG. 5C, the lace 514 is threaded to a pair of guide members 532 that are coupled to the first panel 534 and are separated by a particular distance. This may enable the first panel 534 to be pulled evenly across its width when under tension by the lace 514. Other embodiments are however possible. For example, as shown in FIG. 5D, lace 514 is threaded to the male component 504 of the first closure device 502 and also to a single guide member 554 that is generally coupled to a first extension member or strap 556 of a brace 558. In this example, the female component 506 of the first closure device 502 is generally coupled to a second extension member or strap 560 of the brace 558 or to an edge of the brace 558. Still other embodiments are possible.

Figure 5F:
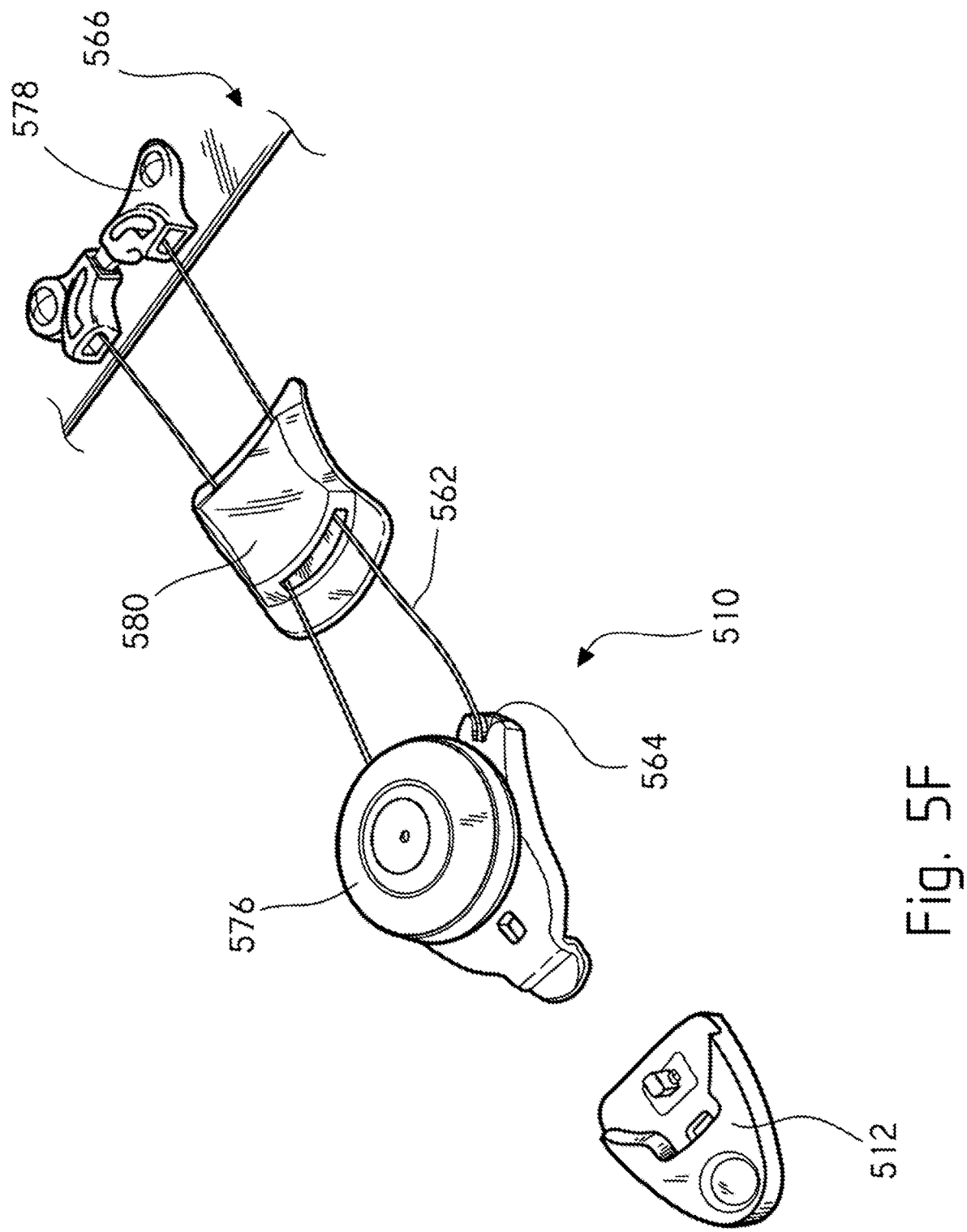

As mentioned above, FIGS. 5E-F illustrate a second closure device 508 that generally comprises a male component 510 and a female component 512. In FIG. 5E, lace 562 is generally threaded to a lumen or passage 564 of the male component 510, and the female component 512 is generally coupled to an end of a brace 566 (see also, FIG. 5F). The lace 562 is also coupled with a first strap 568 that is arranged in an over-and-back configuration between a first d-ring or hook 570, that is coupled with the male component 510, and a second d-ring or hook 572. A second strap 574 is also coupled to the second d-ring 572 and in turn is coupled with the brace 566. In general, the first strap 568 and the second strap 574 together may allow for gross tightening/loosening adjustments of the brace 566, whereas a dial or reel mechanism 576 of the male component 510 may allow for fine tightening/loosening adjustments. In FIG. 5F, in contrast, a distal end of the lace 562 may pass through and/or around a guide member 578 that is coupled with the brace 566, and a floating or mid-point guide 580 may be positioned between the male component 510 and the guide member 578. In this example, the lace 562 may be inserted through channels of the floating guide 580 for lace management purposes, to keep lace aligned about a desired lace path, and/or prevent the lace 562 from having direct contact with skin, which may be uncomfortable for an individual when the lace 562 is under tension. Still other lacing arrangements are possible.

Figure 5G:
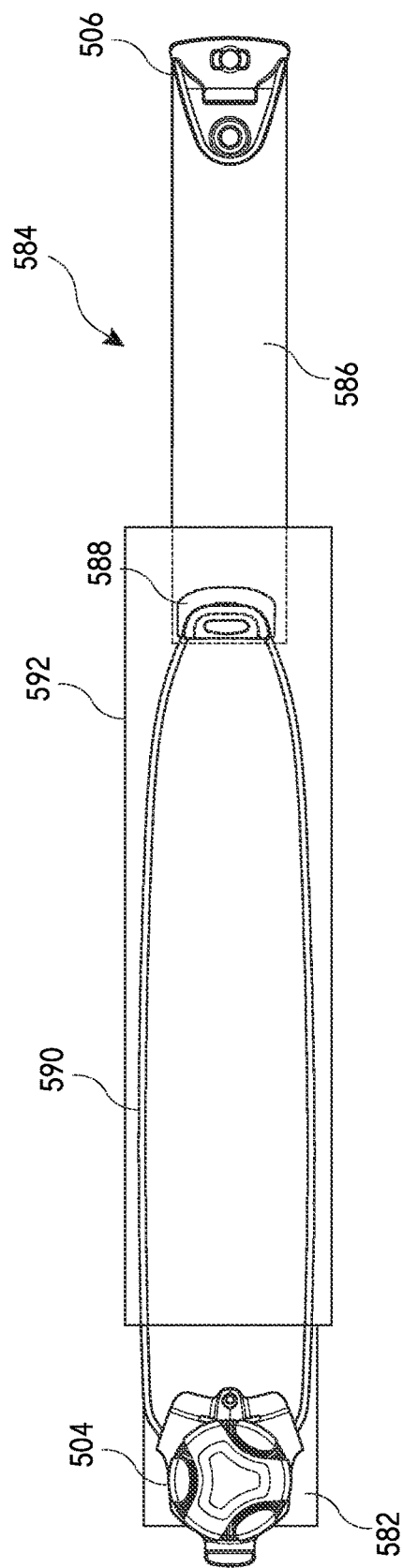
Figure 5H:
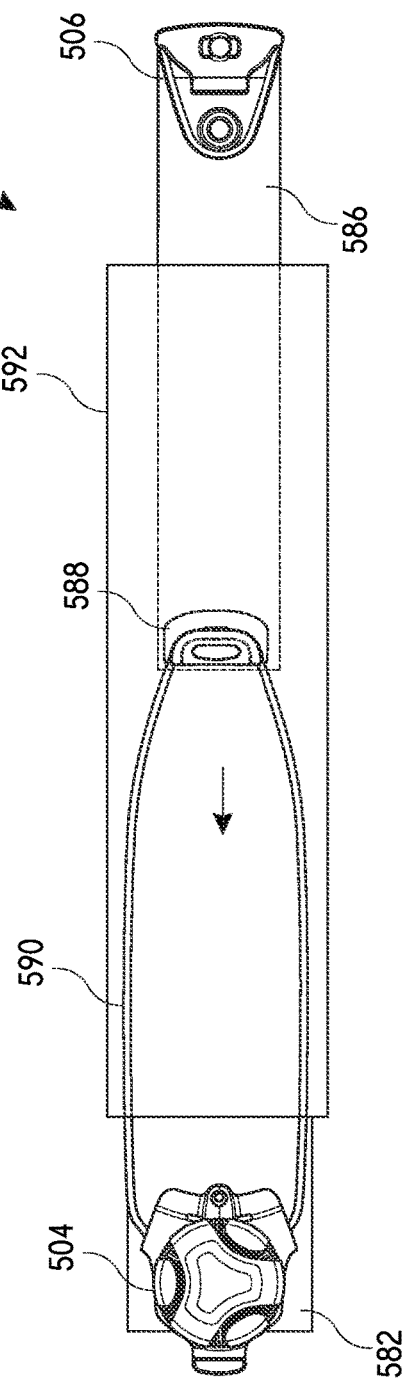

FIGS. 5G-H illustrate the first closure device 502 whereby the male component 504 is generally coupled to a first strap 582 of a brace 584, and the female component 506 is generally coupled to a second strap 586 of the brace 584. In this example, a single guide member 588 is positioned to an end of the second strap 586 opposite the female component 506, and the male component 504 is coupled with lace 590 that in turn is threaded to the guide member 588. A slip sleeve 592 covers and protects the majority of the length of the lace 590 and at least the second strap 586, and also the guide member 588. Such an implementation may beneficially prevent lace 590 and/or other elements or features as shown in FIGS. 5G-H from having direct contact with skin, which may be uncomfortable for an individual when the lace 590 is tensioned. The sleeve 592 also hides the various components of the system from view. In some embodiments, the sleeve 592 may be coupled directly with an end of the male component 504 instead of, or in addition to, the first strap 582.

It will be appreciated that in such embodiments as described in connection with FIGS. 5A-H an individual may be able to easily don/doff a brace and tighten the brace with one hand. For example, an individual may easily place a brace that includes first closure device 502 over a leg or other body part, grasp the male component 504 with a single hand, pull the male component 504 over the leg or body part with the same hand, couple the male component 504 with the female component 506 by inserting the stepped protrusion or tab 522 of the male component 504 into the recess 524 of the female component 506, and subsequently tension the lace 514 by rotating the reel 530. In this manner, the closure devices of the present disclosure may be significantly easier and quicker to use than other closure systems.

Figure 6A:
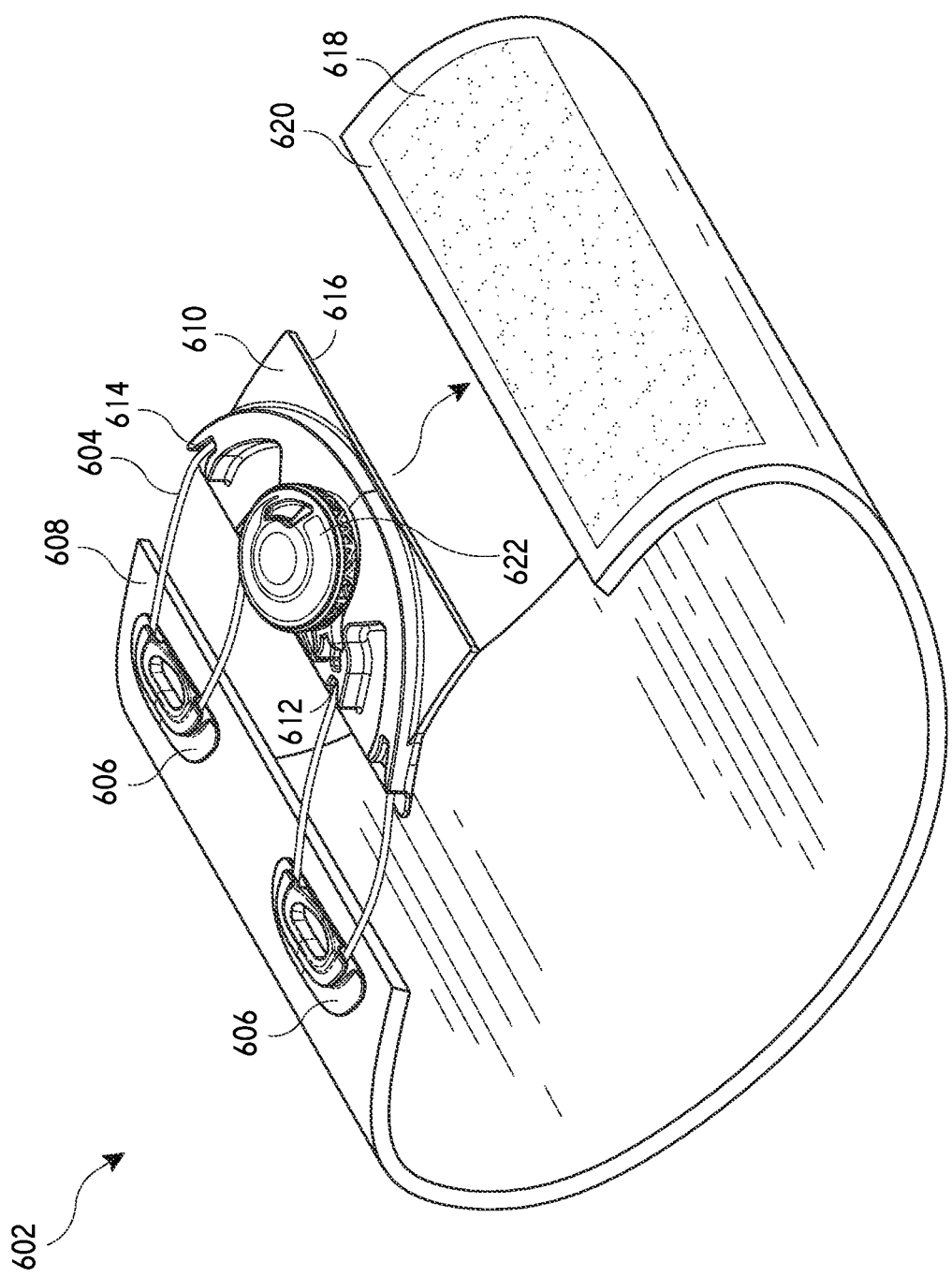
FIGS. 6A-O illustrate various closure systems or devices that may be used to close and tighten or loosen a brace.

Referring now to FIGS. 6A-D, additional closure device embodiments that may be used to close as well as tighten or loosen a brace are shown. For example, FIG. 6A illustrates a brace 602 whereby a lace 604 is threaded to guide members 606 generally coupled to a first end 608 of the brace 602, and also to a reel panel 610 at both a reel mechanism 622 via a reel channel 612 and a peripheral guide 614 positioned in front of the reel mechanism 622 and configured to guide the lace 604 between two lace segments. In use, a bottom side 616 of the reel panel 610 may be coupled to a Velcro® surface 618 generally formed to a second end 620 of the brace 602 to close the brace 602, apply tension to the lace 604, and secure the brace 602 to a limb (not shown) by gross adjustment. The reel mechanism 622 coupled to the reel panel 610 may then be rotated or adjusted to apply or release tension to the lace 604 by winding or unwinding the lace 604 to an internal spool (not shown) of the reel mechanism 622, to further tighten or loosen the brace 602 by fine adjustment. Similar to the above-described embodiments, it will be appreciated that an individual may be able to easily don/doff the brace 602 with one hand. Many other embodiments are possible.

Figure 6B:
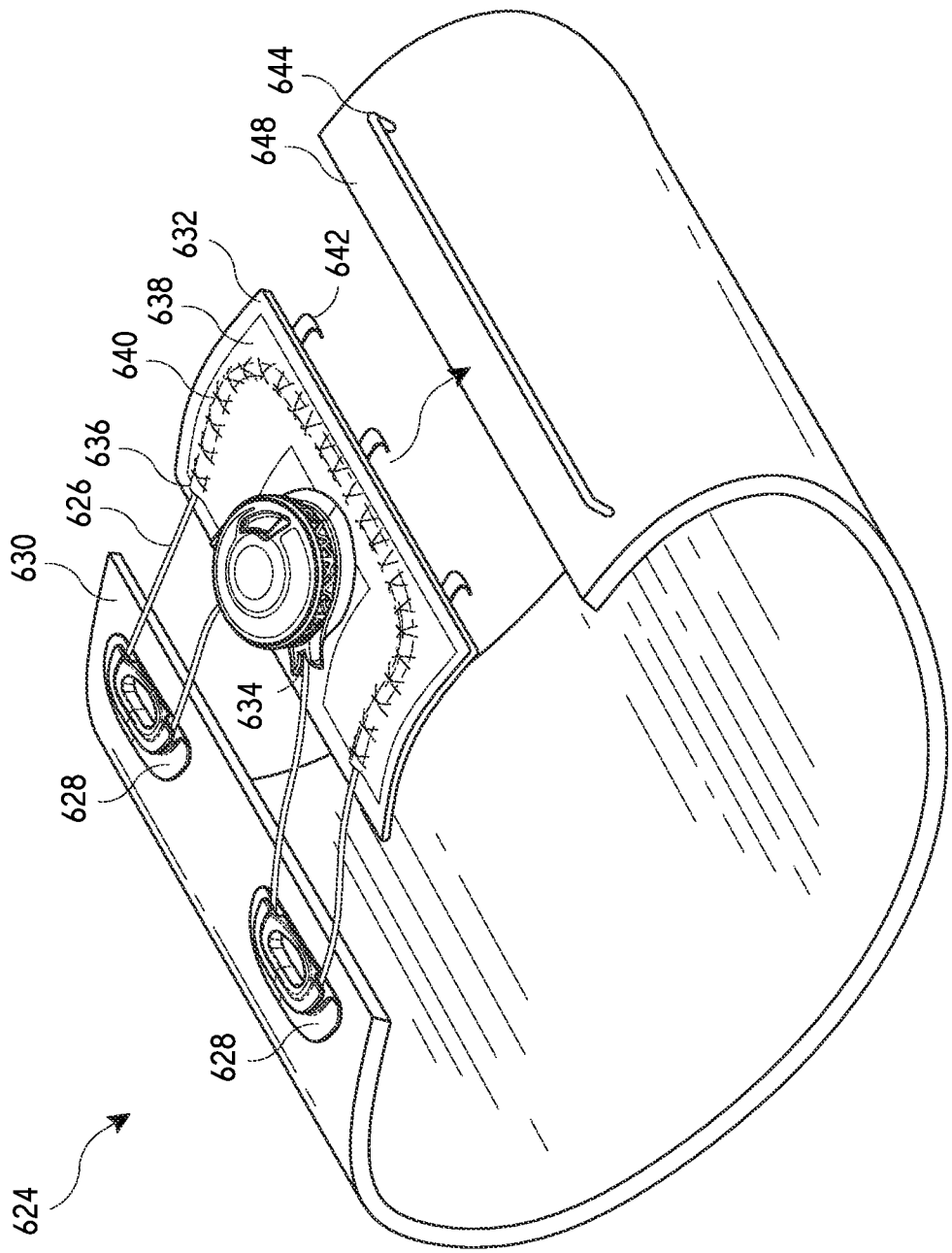

FIG. 6B illustrates a brace 624 whereby lace 626 is threaded to guide members 628 generally coupled to a first end 630 of the brace 624, and also to a reel panel 632 at both a reel mechanism 646 via a reel channel 634 and a peripheral guide 636 positioned in front of the reel mechanism 646 and configured to guide the lace 626 between two lace segments. In this example, however, the peripheral guide 636 is formed by creating a lumen or channel between two a fabric materials 638 via a particular cross-stitch pattern 640. Additionally, one or more hooks 642 of the reel panel 632 may be coupled to a rod 644 that is attached to a second end 648 of the brace 602 to close the brace 624, apply tension to the lace 626, and secure the brace 624 to a limb by gross adjustment. The reel mechanism 646 coupled to the reel panel 632 may then be rotated or adjusted to apply or release tension to the lace 626 by winding or unwinding the lace 626 about an internal spool, to further tighten or loosen the brace 624 by fine adjustment. In coupling the hooks 642 about rod 644, the panel 632 is typically pulled in a first direction to pull the hooks 642 beyond the rod 644, and then retracted in a second direction to couple the hooks and rod. The other embodiments described herein, and in particular the male and female coupling components, do not require motion in opposite directions to couple or attach components of the reel panel.

Figure 6C:
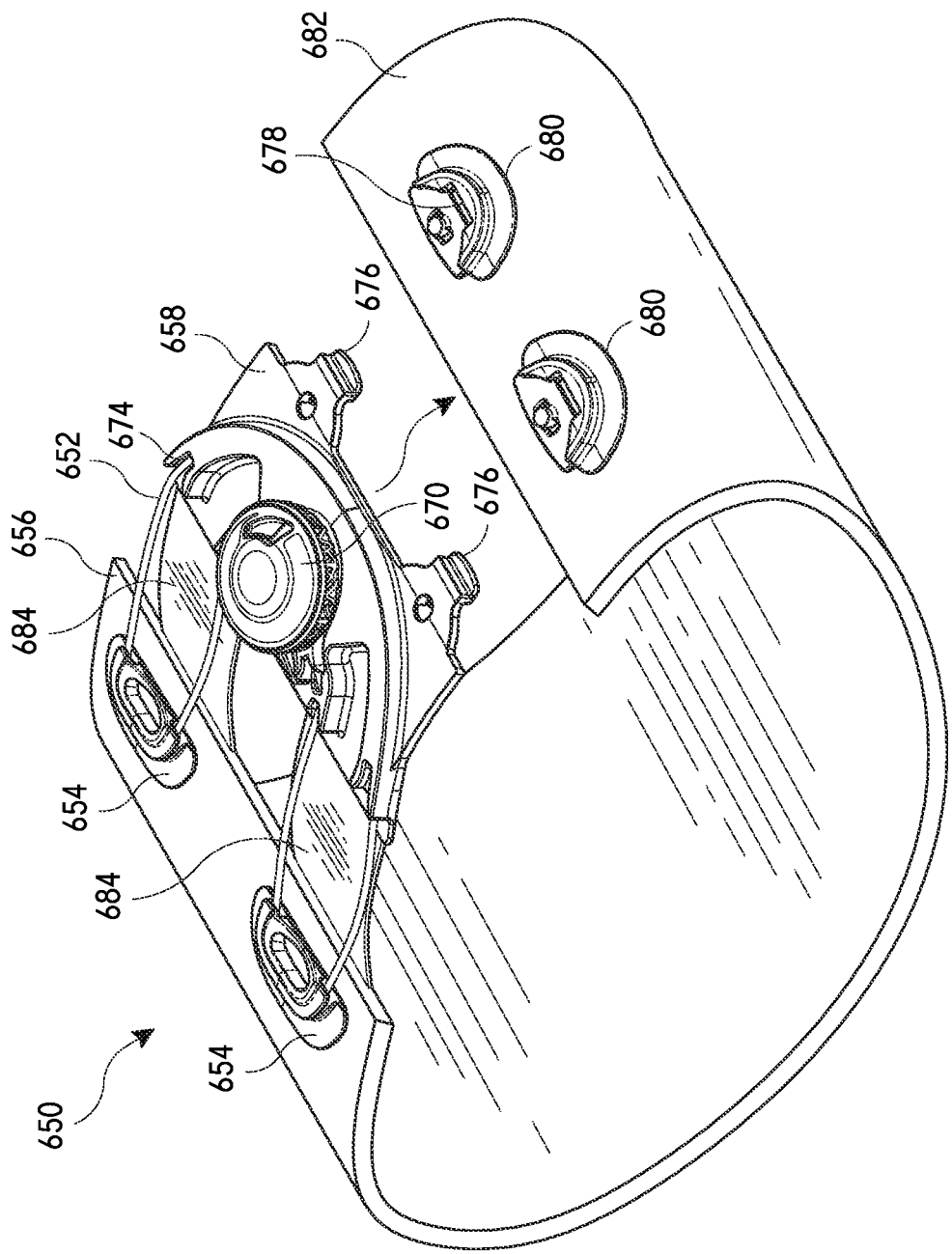

In another example, FIG. 6C illustrates a brace 650 whereby lace 652 is threaded to guide members 654 generally coupled to a first end 656 of the brace 650, and also to a reel panel 658 at both a reel mechanism 670 via a reel channel 672 and a peripheral guide 674 positioned in front of the reel mechanism 670 and configured to guide the lace 652 between two lace segments. The reel panel 658 includes two tab members 676 or male components as described herein. In use, each tab member 676 of the reel panel 658 may be inserted within a complementary recess aperture 678 of a particular female component 680 coupled to, or formed within, a second end 682 of the brace 650, to close the brace 650, apply tension to the lace 652, and secure the brace 650 to a limb by gross adjustment. The reel mechanism 670 may then be rotated or adjusted to apply or release tension to the lace 652 by winding or unwinding the lace 652 to an internal spool, to further tighten or loosen the brace 650 by fine adjustment.

In this example, each tab member 676 of the reel panel 658 and each female component 680 coupled to a second end 682 of the brace 650 are substantially similar to like components discussed above in connection with the first closure device 502. Accordingly, the reel panel 658 may be pushed downward during this process so that snap tabs 526 and an associated aperture 527 (see also, FIG. 6M-O) engage with a grooved post 528 (see also, FIG. 5D or FIG. 8A) of each female component 680 to provide audio and/or tactile feedback to a user. Additionally, as shown in FIG. 6C, strips 684 formed of a flexible and/or elastic material, mesh, or the like, may be coupled to both the reel panel 658 and to the first end 656 of the brace 650 to prevent the lace 652 from having direct contact with skin, which may be uncomfortable for an individual when the lace 652 is under tension.

Figure 6D:
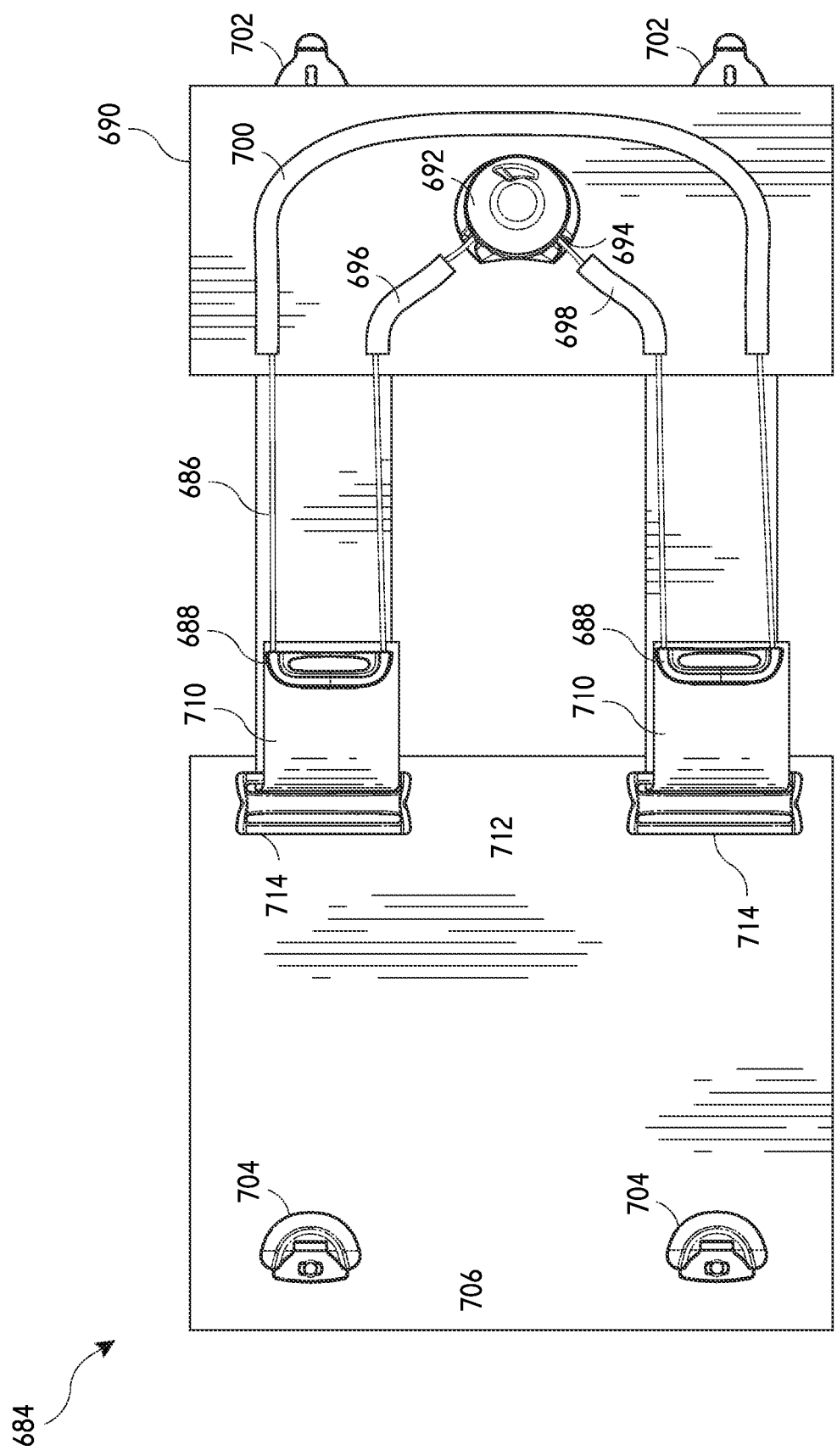

In still another example, FIG. 6D illustrates a brace 684 whereby lace 686 is threaded to guide members 688 and also to a reel panel 690 at both a reel mechanism 692 via a reel channel 694 and guide segments 696, 698, and a peripheral guide segment 700. In this example, each tab member 702 generally coupled to the reel panel 690 and each female component 704 generally coupled to a first end 706 of the brace 684 are substantially similar to like components discussed above in connection with the first closure device 502. The guide members 688 however are coupled to a particular one of elastic extension members or straps 710, which in turn are generally coupled to a second end 712 of the brace 684 at a particular ring 714. In use, length of the straps 710 protruding from each ring 714 may be adjusted as desired, and both gross and fine-closure adjustment may be performed in a manner similar to that described above by virtue of coupling each tab member 702 with a particular female component 704 and adjusting tension applied to the lace 686 using the reel 692.

As briefly mentioned above, the closure devices and/or reel panels of the present disclosure may be variable in length and/or include one or more modular or removable components. Example panels of variable length are shown in FIGS. 6E-J, and an example panel that includes one or more modular or removable components is shown in FIGS. 6K-L. FIGS. 6E-J specifically show multiple views of the reel panel 658 of FIG. 6C, excluding the reel mechanism 670 and internal spool, where FIGS. 6E-G in particular show multiple views of a first embodiment of the reel panel 658, and FIGS. 6H-J show multiple views of a second embodiment of the reel panel 658. The first embodiment of the reel panel 658 differs from the second embodiment of the reel panel 658 primarily in that the second embodiment exhibits more of an elongated shape. Among other things, the second embodiment may, due to an exaggerated shape or profile, distribute load imparted by tensioned lacing across a greater area than that achievable by the first embodiment of the reel panel 658. This may lend the second embodiment of the reel panel 658 to be more suitable for higher tension systems that might use heavier lacing, etc., whereas the first embodiment of the reel panel 658 may be more suitable for lower tension systems. Each of FIGS. 6E-J though illustrate similar features that enable tensioning and loosing of lace threaded to the reel panel 658.

Figure 6E:
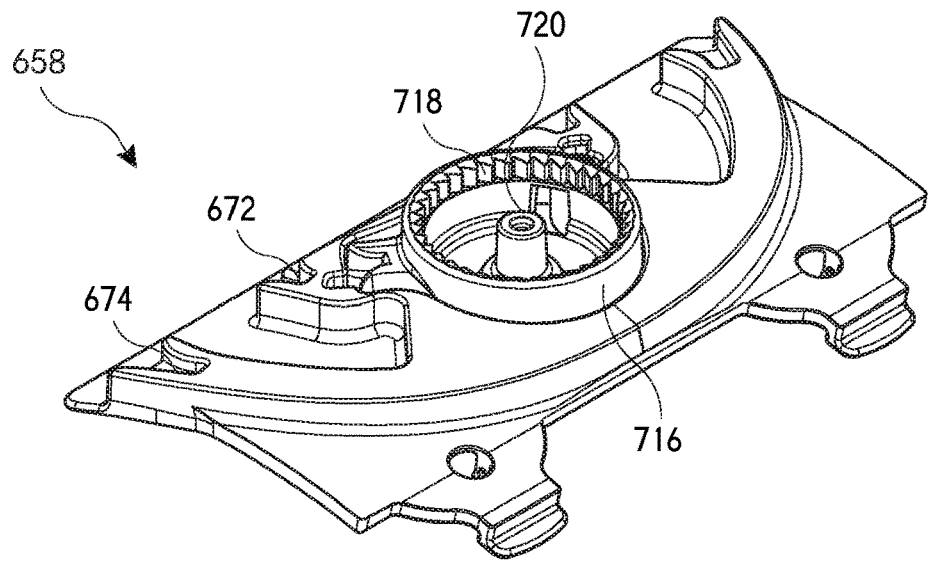
Figure 6F:
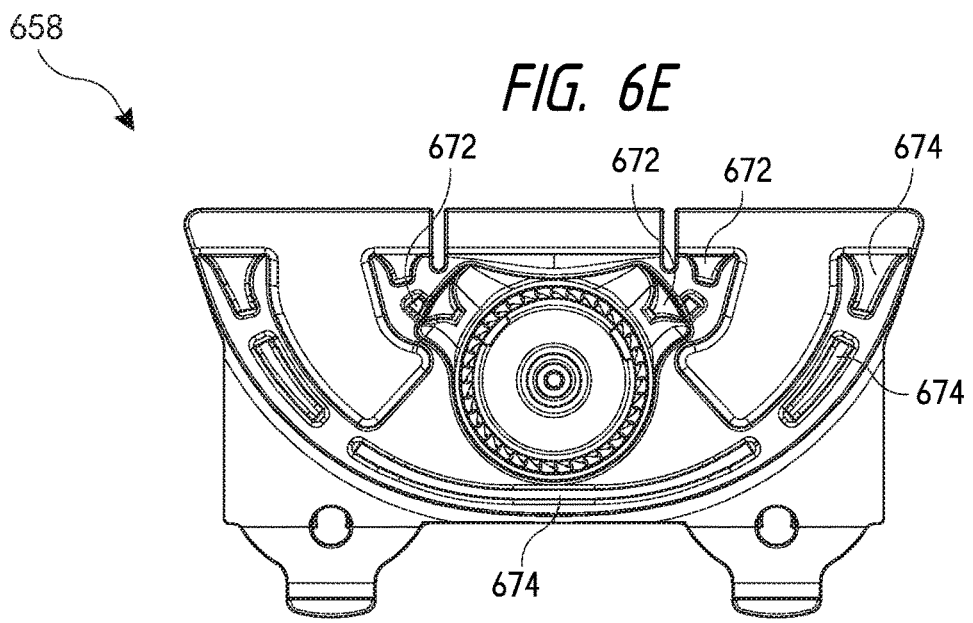
Figure 6G:
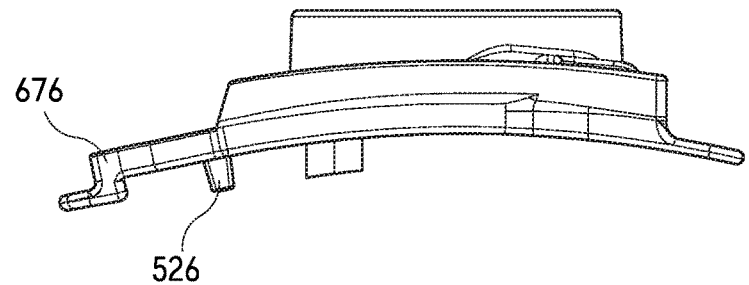
Figure 6H:
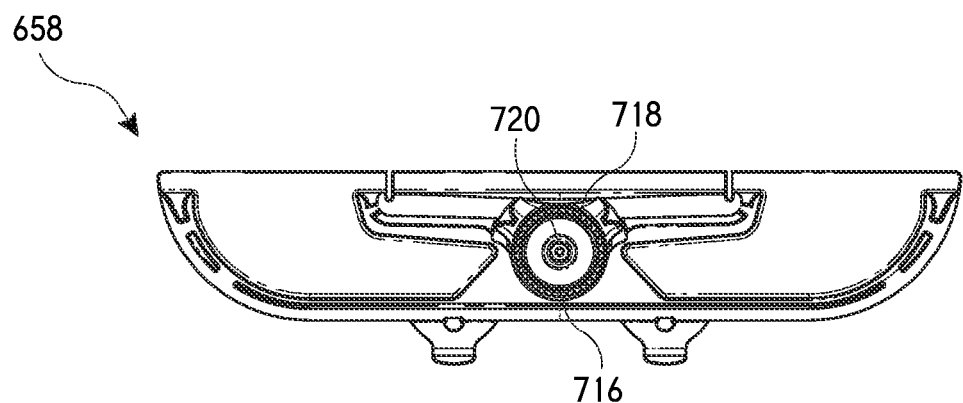
Figure 6I:
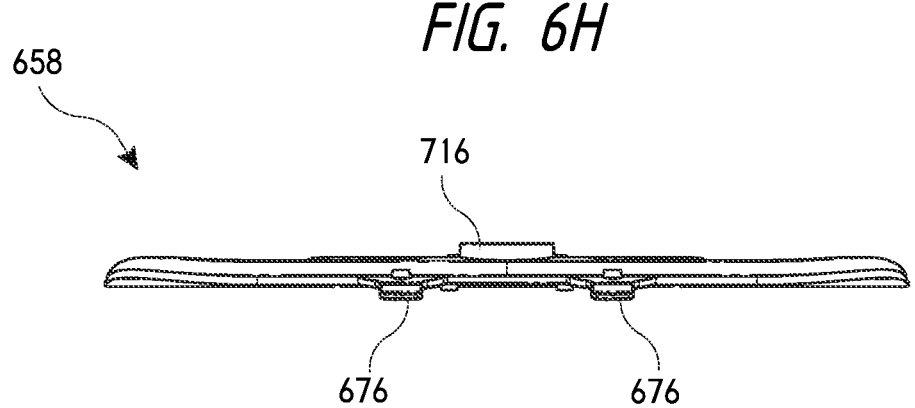
Figure 6J:
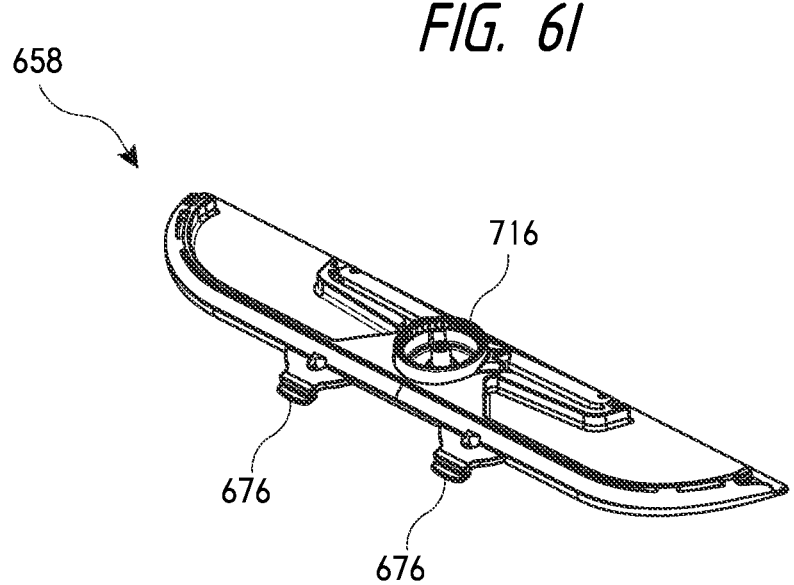
Figure 6K:
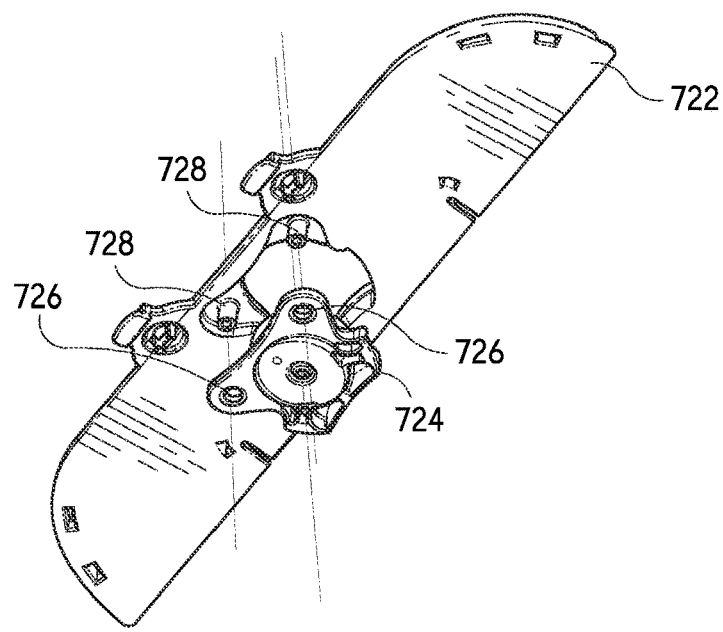
Figure 6L:
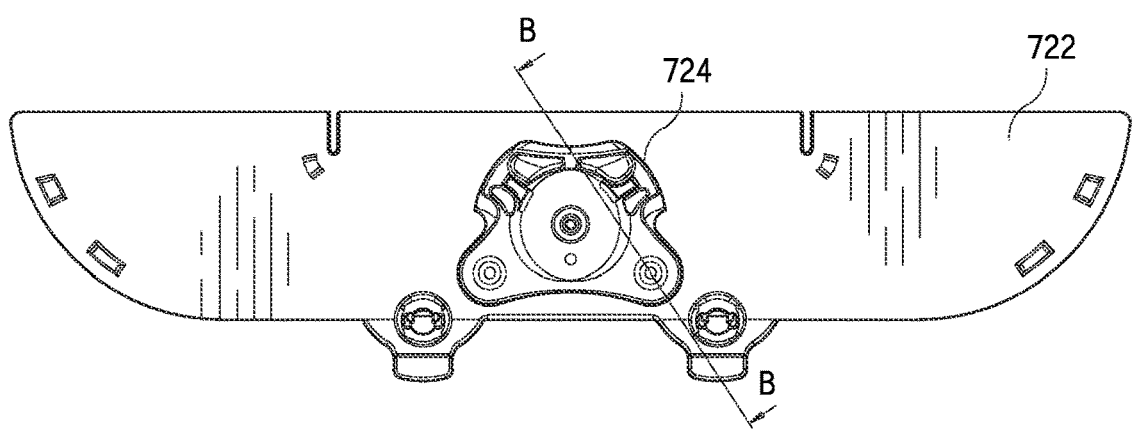
Figure 6L:
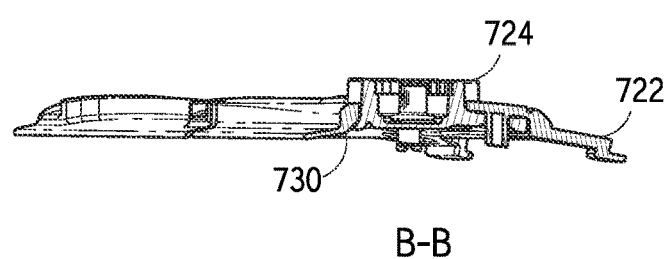

For example, each of FIG. 6E and FIG. 6H show a housing 716 that includes housing teeth 718 and a post 720. The housing teeth 718 engage with corresponding teeth of a pawl disc (not shown) that may be removably coupled with or integrated into the reel mechanism 670. A spool (not shown) may be positioned within the housing 716 axially below the reel mechanism 670 and/or pawl disc. The spool may include a central aperture through which the post or boss 720 is inserted. The spool may include a channel around which the lace is wound. The spool may rotate around the post 720 as the lace is wound around the spool's channel. Similar features are discussed in further detail below in connection with FIG. 10. Also shown in each of FIG. 6E and FIG. 6H is the reel channel 672 and peripheral guide 674 of the reel panel 658, both of which enable threading of lace to the reel panel 658 and/or to different lace segments that span a gap of the brace. FIG. 6F in contrast illustrates in partial cross-section various internal surfaces of the reel channel 672 and peripheral guide 674 of the reel panel 658. Additionally, FIG. 6G and FIG. 6I show a side view and a front view, respectively, of the reel panel 658 including at least one of the tab members 676 and at least one of the snap tabs 526 as discussed above. FIG. 6G further shows curvature of the reel panel 658 when unloaded. It is contemplated that the at-rest curvature of the reel panel 658 may be defined as desired.

Referring now to FIGS. 6K-L, multiple views of an example reel panel 722 that includes an example modular or removable component 724 is shown. In general, the reel panel 722 may correspond substantially to any particular reel panel as discussed within the context of the present disclosure, such as the reel panel 658 as discussed above in connection with at least FIGS. 6E-J. Further, the removable component 724 may correspond substantially to any particular reel or a reel assembly as discussed within the context of the present disclosure, such as the reel mechanism 670 as discussed above in connection with at least FIG. 6C. As alluded to, however, the component 724 is removable and may be rigidly coupled, and then decoupled, to the reel panel 722 as desired.

For example, when initially positioned thereto, fastener apertures 726 of the removable component 724 may be positioned to hollow fastener posts 728 of the reel panel 722 and, as shown in the cross-section of FIG. 6L, a spring-loaded tab 730 of the reel panel 722 may engage with one or more surfaces of the removable component 724 so that the component 724 is snugly fit to the reel panel 722. Fasteners, such as screws, rivets, and the like for example, may then be positioned to the hollow fastener posts 728 of the reel panel 722 and through the fastener apertures 726 of the component 724 to rigidly couple the removable component 724 to the reel panel 722.

Figure 6M:
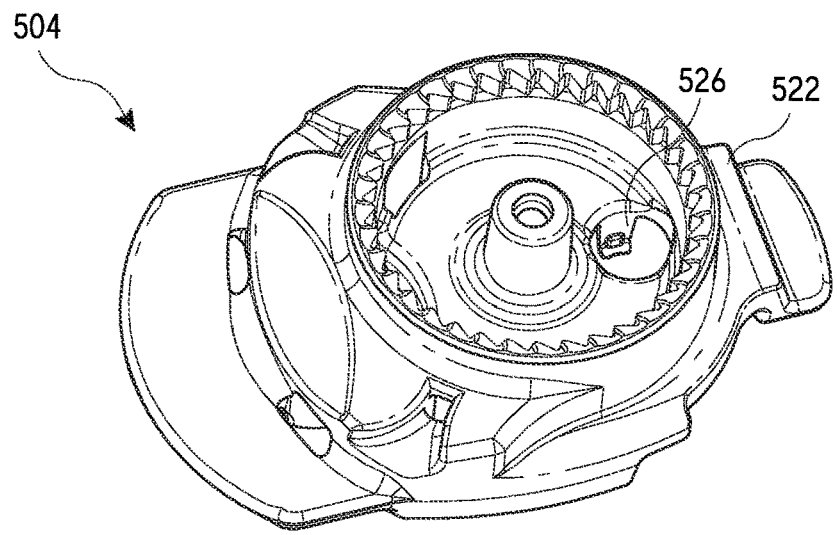
Figure 6N:
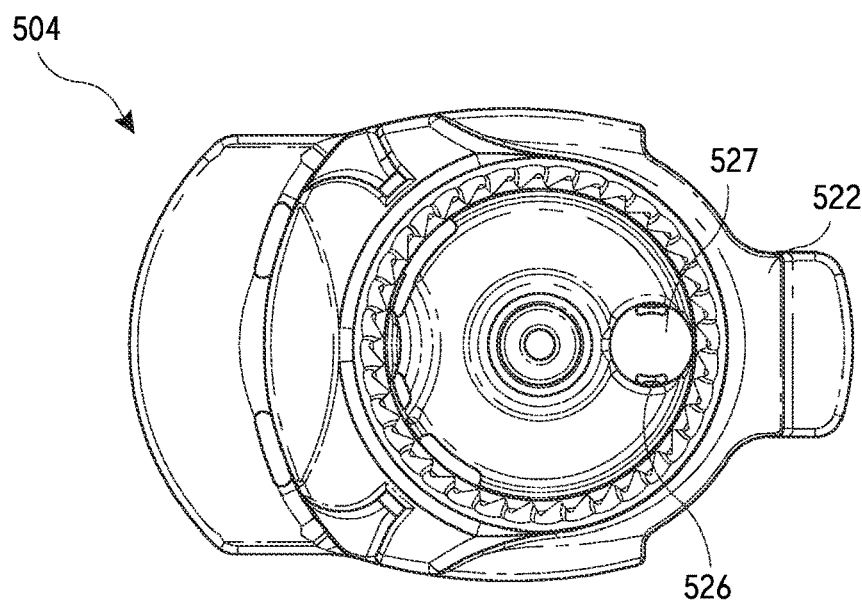
Figure 6O:
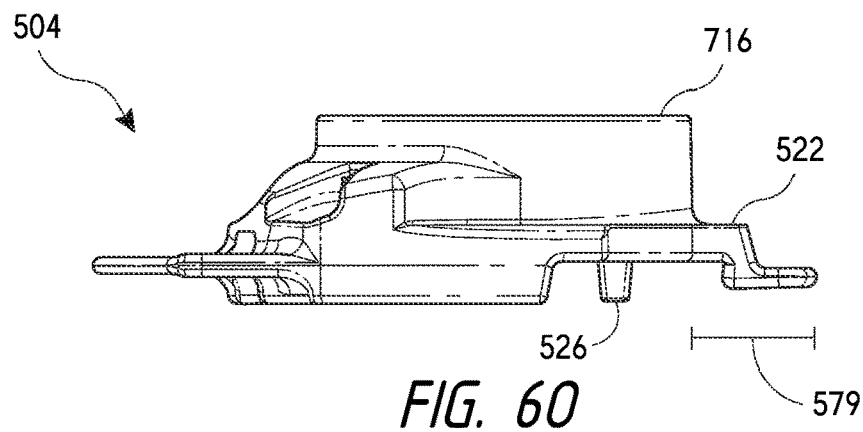

Referring now to FIGS. 6M-O, multiple views of the male component 504, excluding the reel mechanism 530 and internal spool, of the first closure device 502 as discussed above in connection with at least FIGS. 5A-B are shown. In general, the male component 504 of the first closure device 502 is substantially different than the male component 510 of the second closure device 508 as discussed above in connection with at least FIGS. 5E-F. This is because the step-shaped flange or tab 522 of the male component 504 of the first closure device 502 extends or protrudes far less from the housing 716 of the male component 504, when compared to like features of the male component 510 of the second closure device 508. This is achieved by incorporating the aperture 527 and snap tabs 526 of the male component 504 of the first closure device 502 into or within the housing 716 itself. In contrast, with reference to FIG. 5E for example, the snap tabs (not shown) and associated aperture 575 of the male component 510 of the second closure device 508 are incorporated into or on the step-shaped flange or tab 577 of the male component 510 of the second closure device 508. Such an implementation may be beneficial and/or advantageous in many respects. For example, the distance 579 as shown in FIG. 6O of which the tab 522 of the male component 504 of the first closure device 502 extends or protrudes from the housing 716 may be at least about 50% less than the distance 581 of like components of the second closure device 508 as shown in FIG. 5E.

Figure 8A:
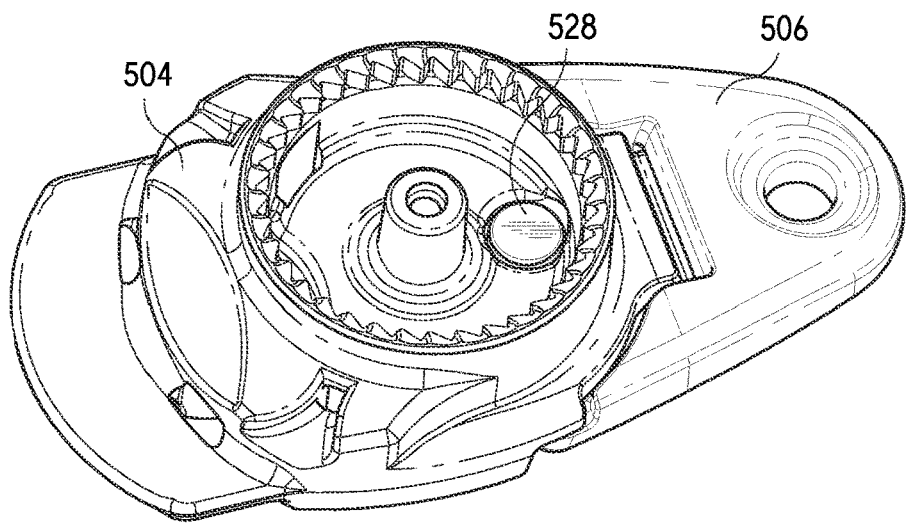
FIGS. 8A-B illustrate multiple views of a mated male component and female component of a particular closure system or device.
Figure 8B:
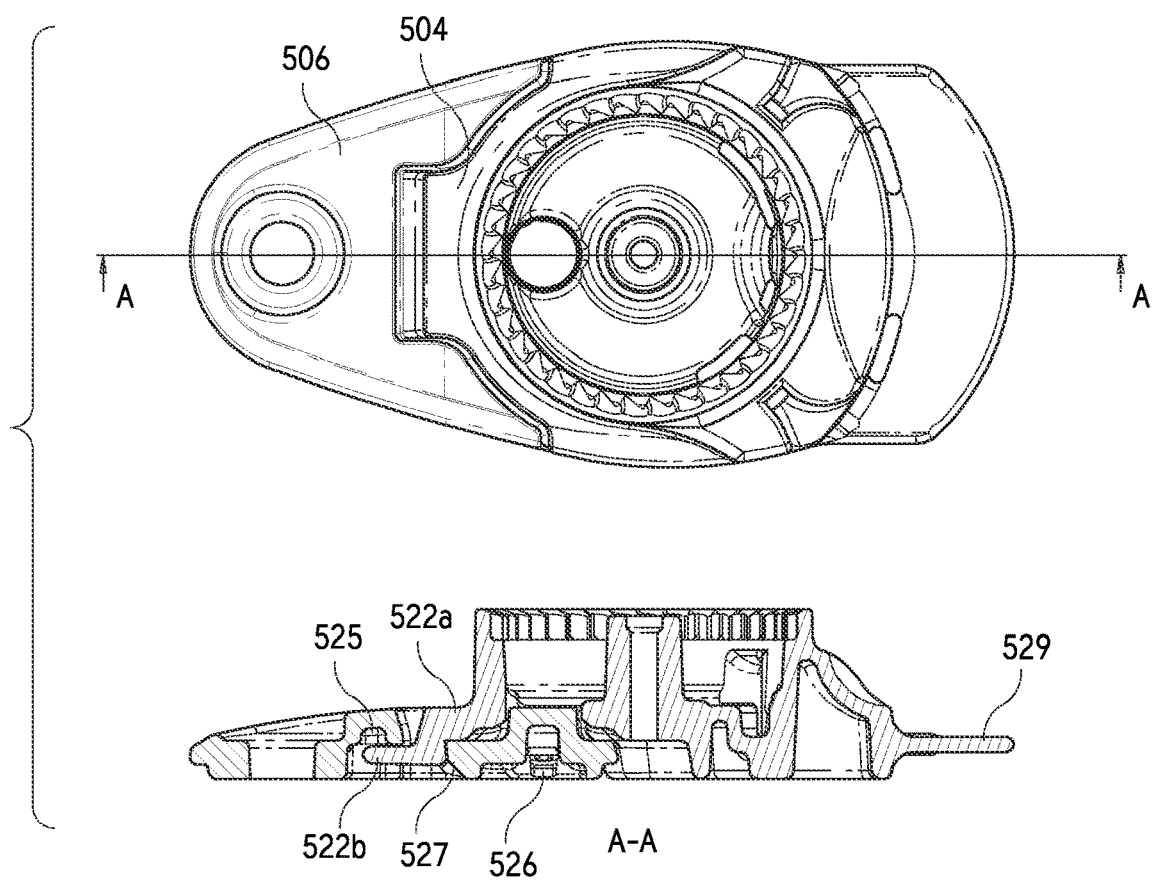

Referring now to FIGS. 8A-B, multiple views of the male component 504, excluding the reel mechanism 530 and internal spool components, of the first closure device 502 coupled to the female component 506 of the first closure device 502 are shown. In this example, the coupling member or tab 522 (see also, FIGS. 6M-O) of the male component 504 is mated with a coupling recess 524 (see also, FIG. 5D) of the female component 506 to couple or mate the two components. In some embodiments, the coupling member or tab 522 is a stepped protrusion that is positioned at a distal end of a main body of male component 504. As shown in FIG. 8B, the stepped protrusion or tab 522 includes a tab 522a that extends approximately orthogonally downward from the main body of male component 504. A flange 522b extends approximately orthogonally from a distal end of the tab 522a such that the coupling member or tab 522 has a generally L-shaped or Z-shaped profile. The flange 522b has a relatively planar top surface that is offset from a relatively bottom surface 523 (see also, FIG. 5A) of the main body of male component 504. The term "relatively planar surface" as used herein may indicate that the surface is generally flat, but may include surfaces that are slightly curved and/or include other surface irregularities. The tab 522a and the flange 522b may collectively be referred to stepped protrusion or tab 522.

As also shown in FIG. 8B, the coupling recess 524 of the female component 506 includes a recessed portion 525 that is positioned immediately adjacent the coupling recess 524. The recessed portion 525 is typically a recess within a bottom portion of the main body of female component 506. In coupling the male component 504 and the female component 506, the stepped protrusion or tab 522 is insertable within the coupling aperture 524 such that the relatively planar top surface of the flange 522b is positioned immediately adjacent and under the recessed portion 525 of the female component 506. When the components are coupled together, a proximal or rear surface of the tab 522 engages with a lip or distal surface 527 of the coupling recess 524. Engagement of the rear surface of the tab 522 and the lip 527 of the coupling recess 524 maintains a coupled engagement of the male and female components 504, 506 when tension is applied between the components, such as when a tension member (e.g., lace or strap) is tensioned via a reel mechanism and the like. FIG. 8A-B also illustrate the grooved post 528 of the female component 506 engaged with the tabs 526 of the male component 504. The coupled components have a shorter overall length and/or profile due to the incorporation of the aperture 527 and snap tabs 526 within the housing of the male component 504. The smaller profile and/or length of the coupled components is advantageous in that the components occupy a smaller space on the brace and/or do not press downward against the user's body when the lace is tensioned. The small and compact design of the device also reduces contact of the device with objects as the user wears the brace.

Figure 9:
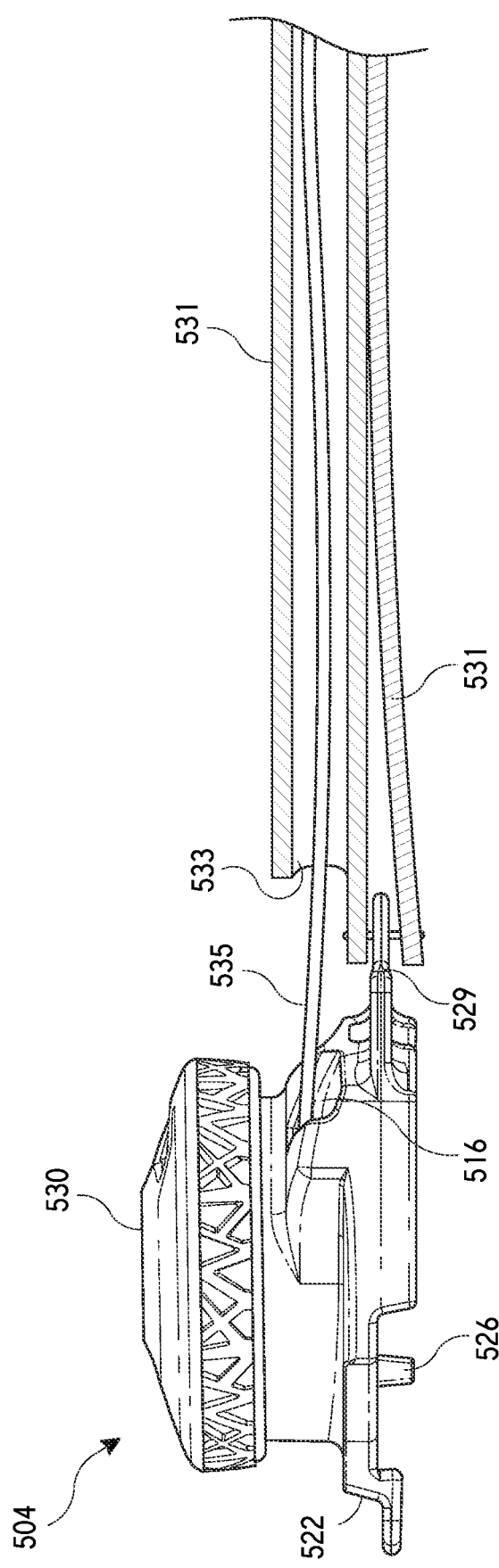
FIG. 9 illustrates a side view of a male component of a particular closure system or device coupled to a fabric material.
Figure 10A:
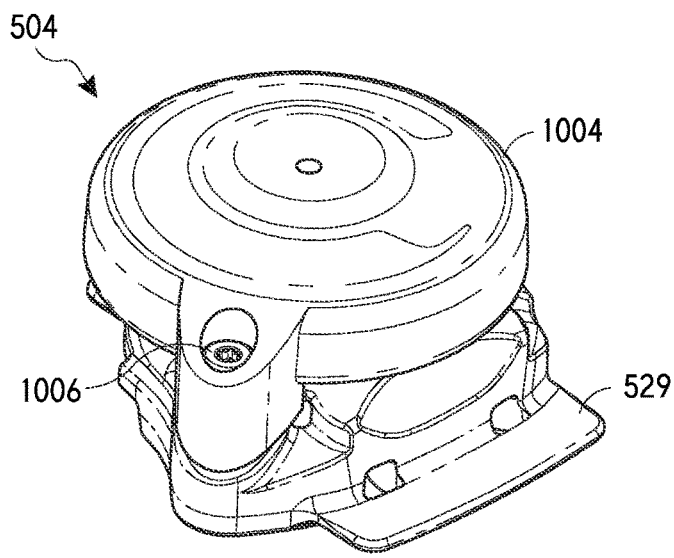
FIGS. 10A-D illustrate multiple views of a male component of a particular closure system or device.
Figure 10B:
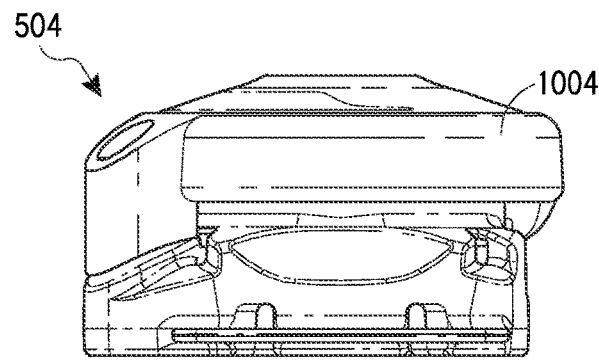
Figure 10C:
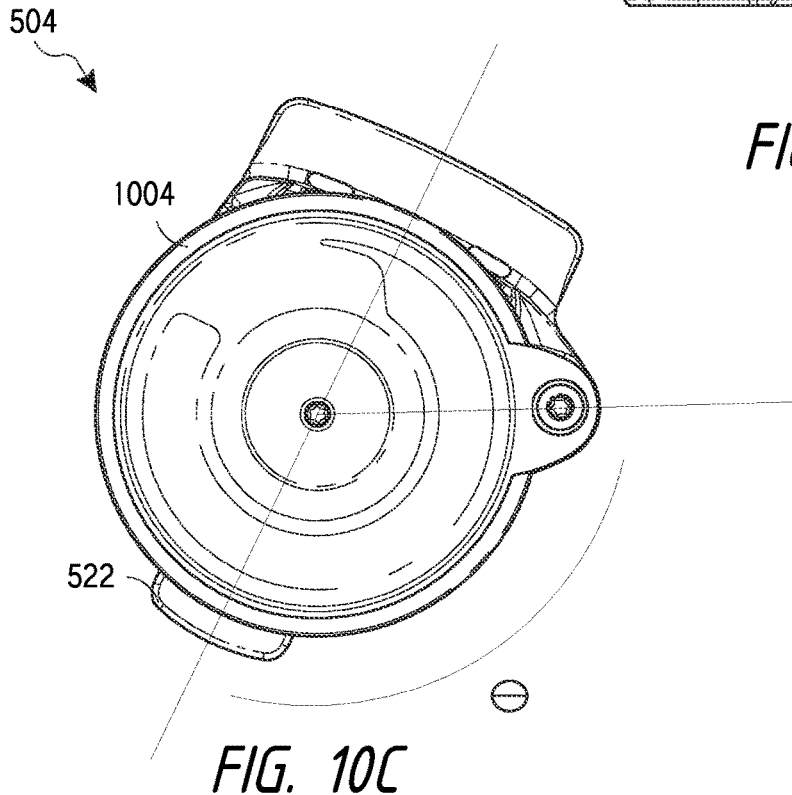
Figure 10D:
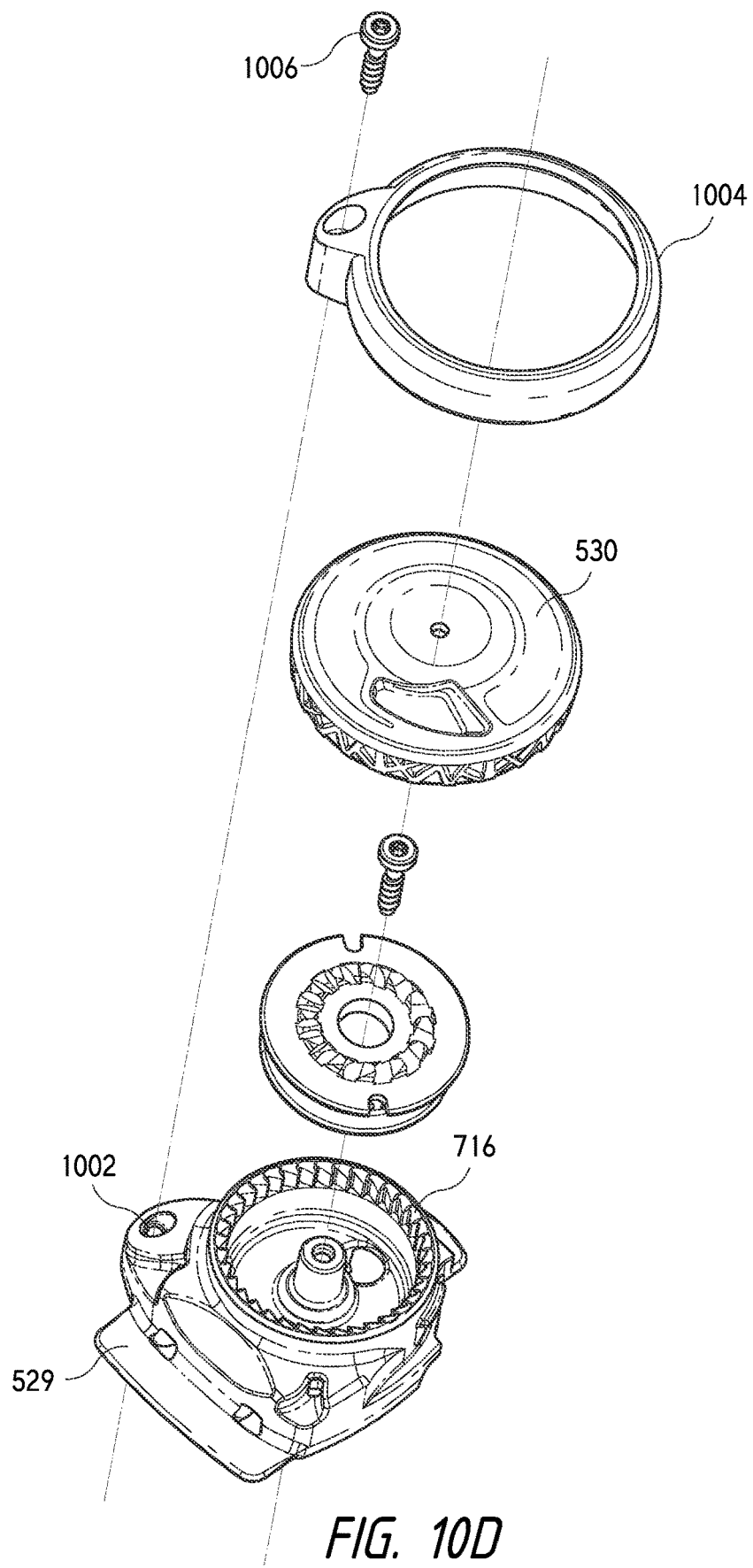

Referring now to FIG. 9, a side view of the male component 504, including the reel mechanism 530 and internal spool components, of the first closure device 502 is shown whereby a stitching flange 529 of the male component 504 is positioned relative to the lumen or passage 516 of the male component 504, so that when fabric 531 or other material is stitched to the stitching flange 529 a channel 533 containing lacing 535 is orientated approximately parallel or in-line with the lumen or passage 516. The channel 533 may be an internal channel of sleeve 592 previously described, which is designed to cover and/or hide the lace 535 and/or other components.

The stitching flange 529 is positioned so as to be axially offset from a bottom surface of the male component 504. In some embodiments, the stitching flange 529 may be offset between about 1 and 5 mm, and more commonly between about 1 and 2 mm, from the bottom surface of the male component 504 to align the channel 533 with the passage 516. In a specific embodiment, the stitching flange 529 may be offset between about 1.3 and 1.5 mm from the bottom surface of the male component 504. Such an implementation or feature may be beneficial and/or advantageous in many respects. For example, friction or other degrading interactions between the lacing 535 and the fabric 531 may be minimized to prevent premature degradation of the lacing 535. The axially offset stitching flange 529 also allows the stitching flange 529 to be inserted between two layers of the fabric 531 as well. The stitching flange 529 may be coupled with fabric 531 via stitching, adhesive bonding, RF welding, and the like.

Referring now to FIGS. 10A-D, multiple views of an alternative embodiment of the male component 504 of the first closure device 102 are shown. In particular, the male component 504 is formed to exhibit a screw boss 1002 that is angularly offset from the tab 522 by an angle θ such that the screw boss 1002 is generally positioned on a side of the component 504, typically closure to the stitching flange. Positioning the screw boss 1002 on the side of the component 504 in this manner may maintain a minimized distance that the tab 522 and stitching flange extends or protrudes from the housing 716 of the male component 504 for reasons similar to those discussed above in connection with at least FIGS. 6M-O. For example, positioning the screw boss 1002 so as to be radially in line with either the tab 522 or stitching flange would require that the tab 522 or stitching flange extend radially farther from the housing 716, which increases the overall profile and/or length of the male component 504. In some embodiments, the angle θ may be between about 90 and 130 degrees, although an angle θ of between about 110 and 125 degrees is more common. In a specific embodiment, the angle θ is between about 115 and 120 degrees, which has been found to optimally position the screw boss 1002 away from the front edge and tab 522 and toward the rear-side edge of the male component 504 adjacent the lace ports or channels. The angle θ of 115 to 120 degrees also positions the screw boss 1002 from projecting directly out of the edge of the male component 504, which positioning would greatly increase the width of the component.

A security ring 1004 may be fastened to the male component 104 using a fastener 1006 to prevent unintended or unauthorized rotation of the reel mechanism 530 of the male component 504 to loosen or tighten a lace that is coupled thereto. Such an implementation or feature may be beneficial and/or advantageous in many respects. For example, a brace comprising the male component 504 of the first closure device 102 as shown in FIGS. 10A-D may be fitted to a limb of a minor child, for example, who may have the tendency to play with the reel mechanism 530 without understanding the possible negative implications of doing so. The security ring 1004 however when coupled to the male component 504 may prevent the minor child from doing so. In other embodiments, the reel mechanism 530 may be keyed (i.e., hexagonally shaped and the like) and the security ring 1004 may be correspondingly keyed so that rotation of the reel mechanism 530 within the security ring 1004 is prevented. In yet other embodiments, the security ring 1004 may include a protrusion or other feature that prevents rotation of the reel mechanism 530.

Figure 11A:
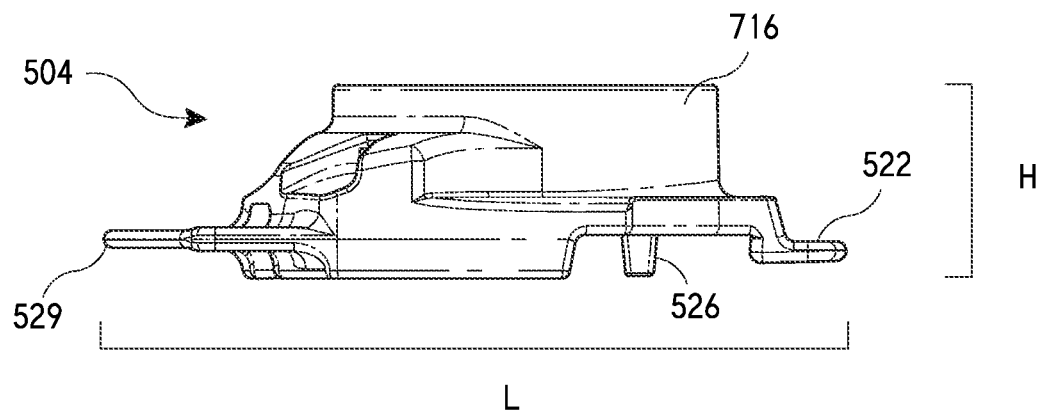
FIGS. 11A-D illustrate multiple views of various components of a male component of a particular closure system or device.
Figure 11B:
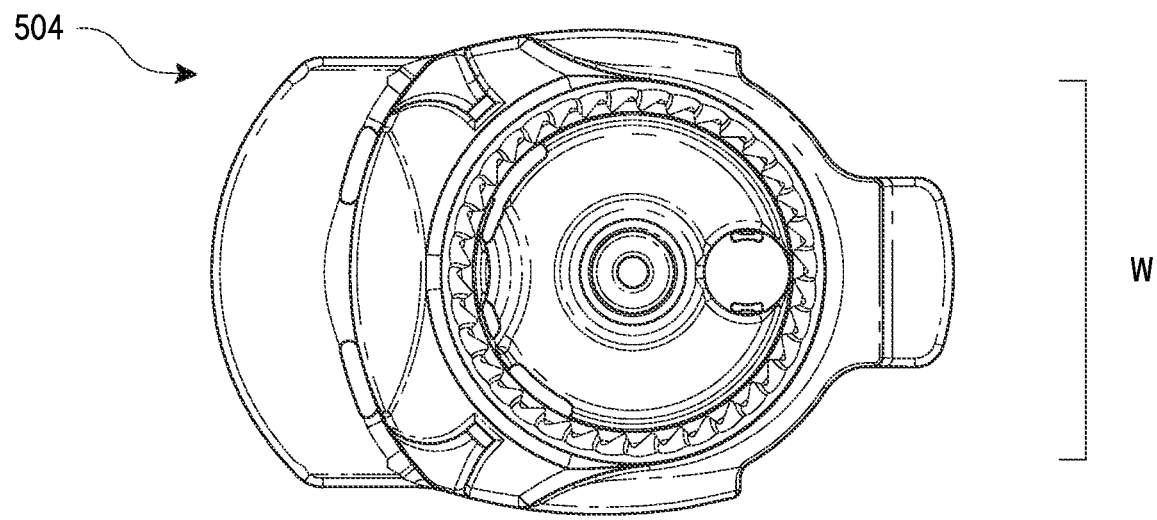
Figure 11C:
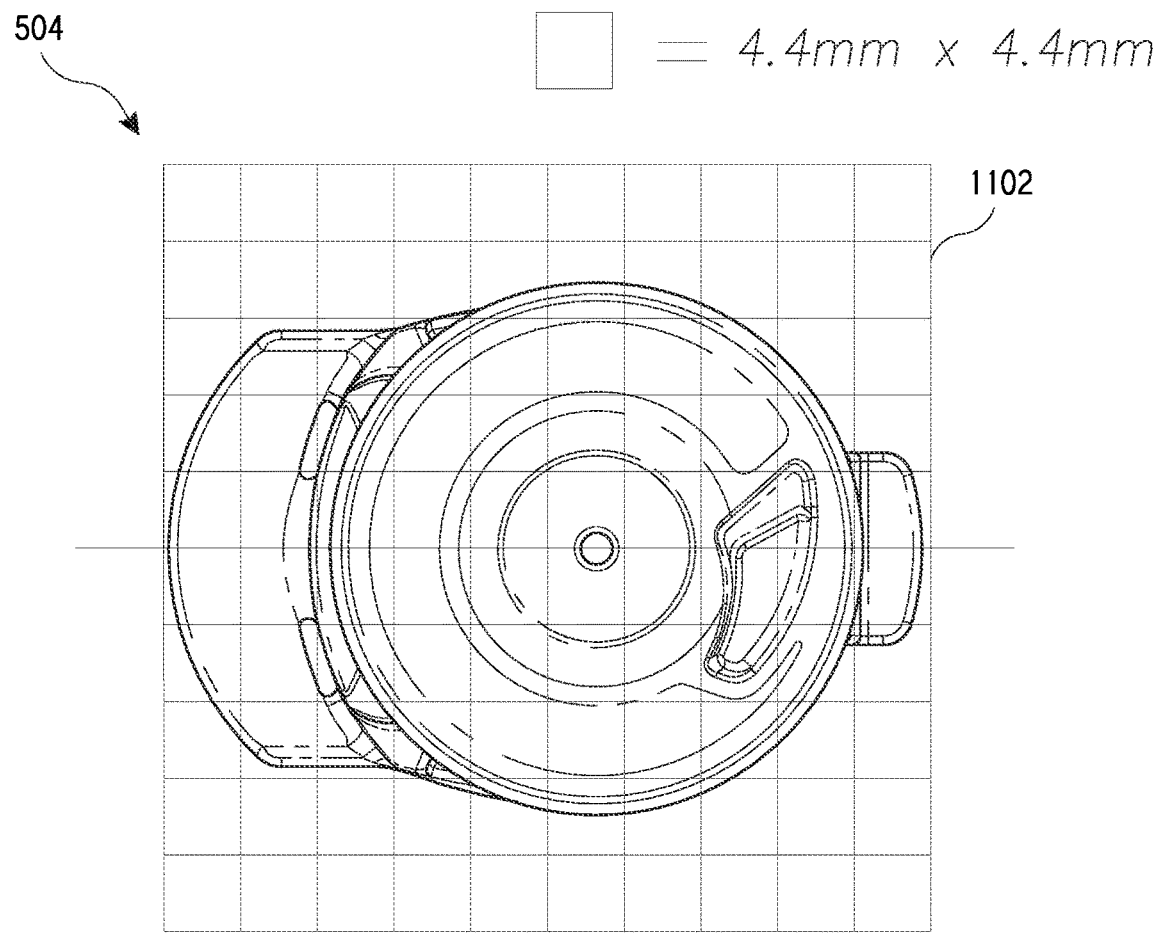
Figure 11D:
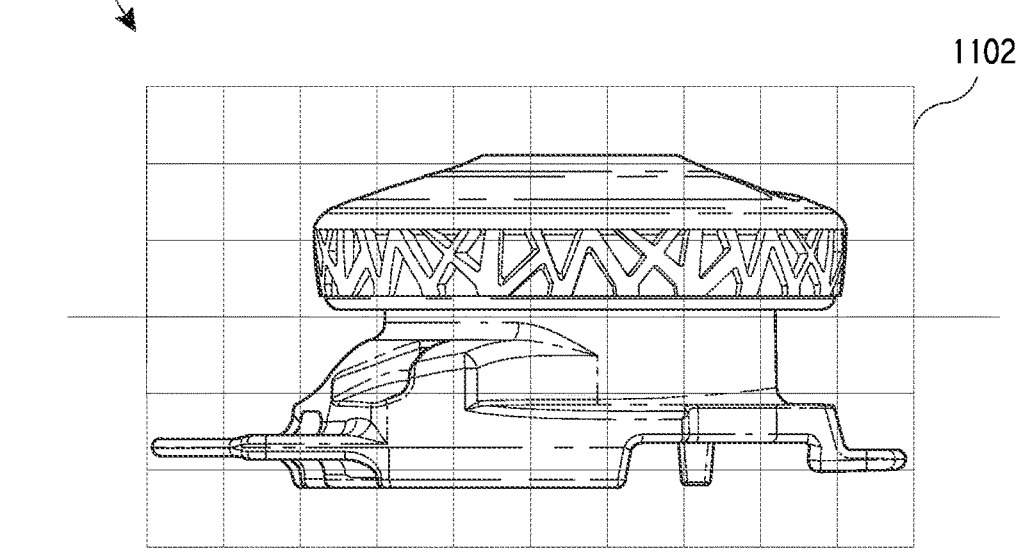

Referring now to FIGS. 11A-D, multiple views of various components of the first closure device 502 are shown. In particular, FIGS. 11A-B illustrate multiple views of the male component 504, excluding the reel mechanism 530 and internal spool components, where length, width, and height dimensions of the male component 504 are generally shown. In some embodiments, the length of the male component 504 may be between about 30 and 60 mm, although a length of between about 40 and 50 mm is more common and provides a more compact configuration. In a specific embodiment, the length of male component 504 is between about 42 and 46 mm, which has been found to provide a compact yet robust configuration. In some embodiments, the width of the male component 504 may be between about 15 and 45 mm, although a width of between about 25 and 35 mm is more common and provides a more compact configuration. In some embodiments, the height of the male component 504 may be between about 10 and 30 mm, although a height of between about 15 and 25 mm is more common and provides a more compact configuration. FIGS. 11C-D in contrast illustrate multiple views of the male component 504, including the reel mechanism 530 and internal spool components, where a grid 1102 may assist in calculating various dimensional aspects of the male component 504. In this example, each block of the grid 1102 may be about 4.4 mm by about 4.4 mm.

In some embodiments, one or more of the panels and/or components of the closure devices of the present disclosure may be formed by an injection molding process from flexible materials such as molded elastomer (e.g., silicone, rubber), molded polyurethane soft foam (e.g., Polycell®) that allows for a bacteria free surface, cushion ability & durability, molded foam resin (e.g., Croslite®), and the like. In some embodiments, the volume of material used to form the male component 504, including the reel 530 and internal spool components, as shown in FIGS. 11C-D, may be in range from about 6000 cubic millimeters to about 12000 cubic millimeters.

In some embodiments, the volume of material used to form the male component 504, including the reel 530 and internal spool components, as shown in FIGS. 11C-D, may be about 6006 cubic millimeters, about 6418 cubic millimeters, about 7584 cubic millimeters, about 7720 cubic millimeters, about 7740 cubic millimeters, about 7829 cubic millimeters, about 10358 cubic millimeters, or about 11187 cubic millimeters. Such values for the volume of material used to form the male component 504, including the reel 530 and internal spool components, as shown in FIGS. 11C-D, may each be associated with a particular style of the male component 504. Additionally, larger volumes may be preferable for higher tension applications, such as for tightening the brace or article about larger limbs/bodily segments, including leg braces, knee braces, back braces, and the like. In contrast, smaller volumes may be preferable for lower tension applications, such as for tightening the brace or article about smaller limbs/bodily segments, including arm braces, neck braces, wrist braces, and the like.

As described herein, the configuration of the male component results in compact closure and tightening device, or stated differently, in a compact device that is able to provide both gross or macro closure of a brace or article and fine or micro adjustment of the tightness of the brace or article about a limb or bodily segment. The above material volumes illustrate the compactness of such a device. Conventional devices are not able to offer both gross closure and micro adjustment of a brace or article in such a compact volume. Some aspects of the design that allow the male component to achieve such compactness include: the position of the aperture 527 within housing 716, the position and/or design of the stitching flange, and/or the angular offset of the screw boss 1002. The compact design of the male component further enables the female component and coupled components to have a small and compact configuration.

Figure 12:
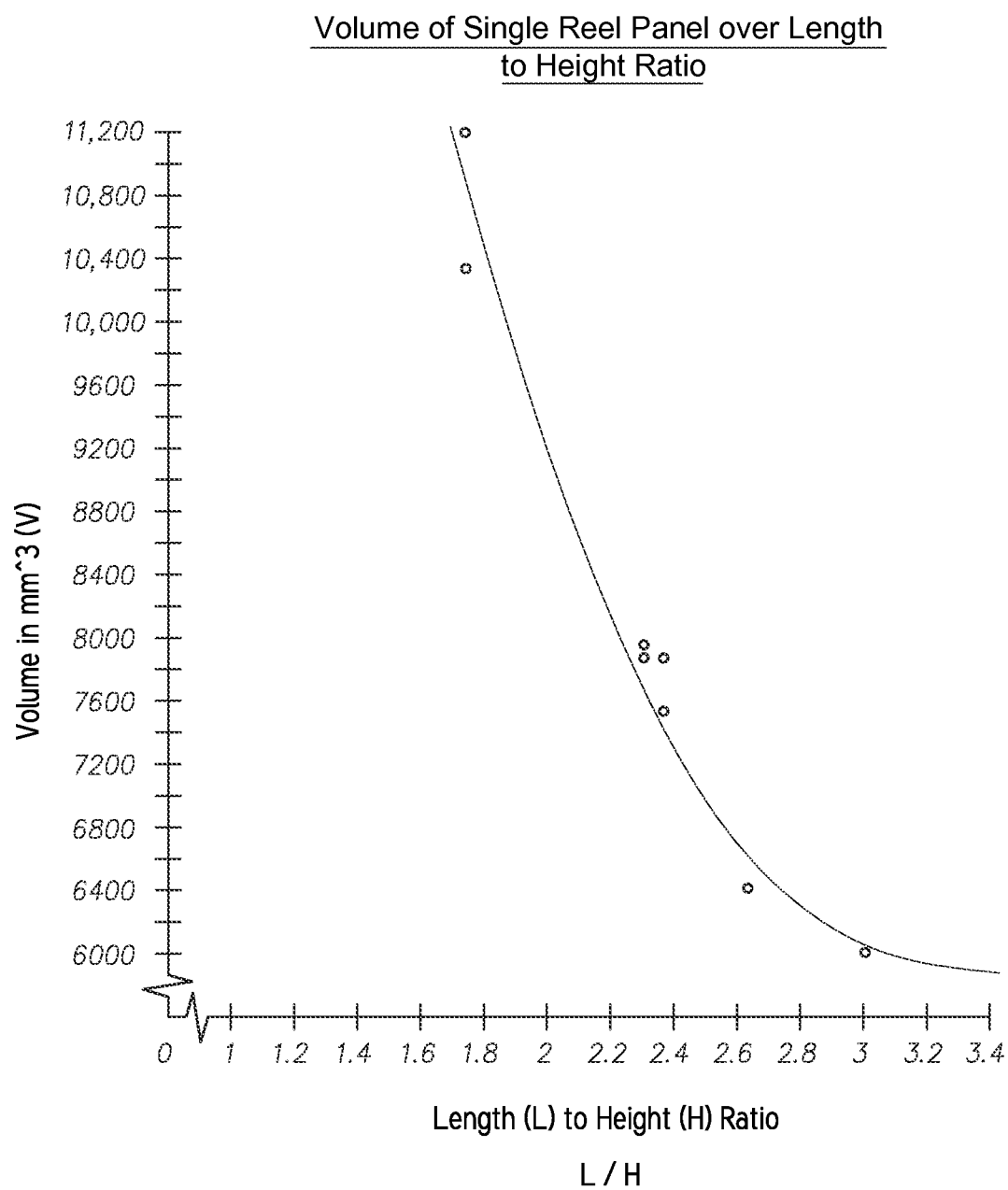
FIG. 12 illustrates a plot that shows the dependence of the volume of material used to form a male component of a particular closure system or device on one or more physical dimensions of the male component.

Referring now to FIG. 12, a plot 1200 shows the dependence of the volume of material used to form the male component 504 as shown in FIGS. 11C-D on one or more dimensions of the male component 504. Specifically, FIG. 12 plots the material volume of the male component 504 as a function of the ratio of length/height of the component. A taller male component 504 (i.e., greater height H) usually results from enhancing the reel mechanism 530 to provide greater lace tensioning and brace tightening strength. The length of the male component 504 may not be increased by a corresponding amount, resulting in a male component 504 that is slightly more square shaped (i.e., having an L/H aspect ratio closer to 1). As shown in FIG. 12, a relatively longer and shorter male component 504 results in a relatively smaller volume, which usually corresponds to a smaller reel mechanism 530 being used. As shown in FIG. 12, an L/H aspect ratio of between 2 and 2.6, and more specifically between about 2.2 and 2.4, may provide an optimal balance of reel mechanism power and compact component volume. Such a male component 504 may be well suited for most brace/article closure and tightening needs. A L/H aspect ratio greater than 2.6 may be desired when the significant design consideration is compact size, while an L/H aspect ratio of less than 2 may be desired when the significant design consideration is reel mechanism power. Other aspect ratios and volume dimensions are also possible. Table 1 below includes the data of some of the male components 504 plotted in FIG. 12.

TABLE 1

| Component | Volume (mm³) | Height (mm) | Length (mm) | Width (mm) |
| --- | --- | --- | --- | --- |
| 1 | 6,006 | 14.2 | 42.9 | 28 |
| 2 | 7,720 | 18.4 | 43.7 | 28.6 |
| 3 | 6,418 | 16.3 | 43.1 | 28.2 |
| 4 | 7,829 | 19 | 43.7 | 30.5 |
| 5 | 11,187 | 26 | 46 | 35.8 |

Figure 13:
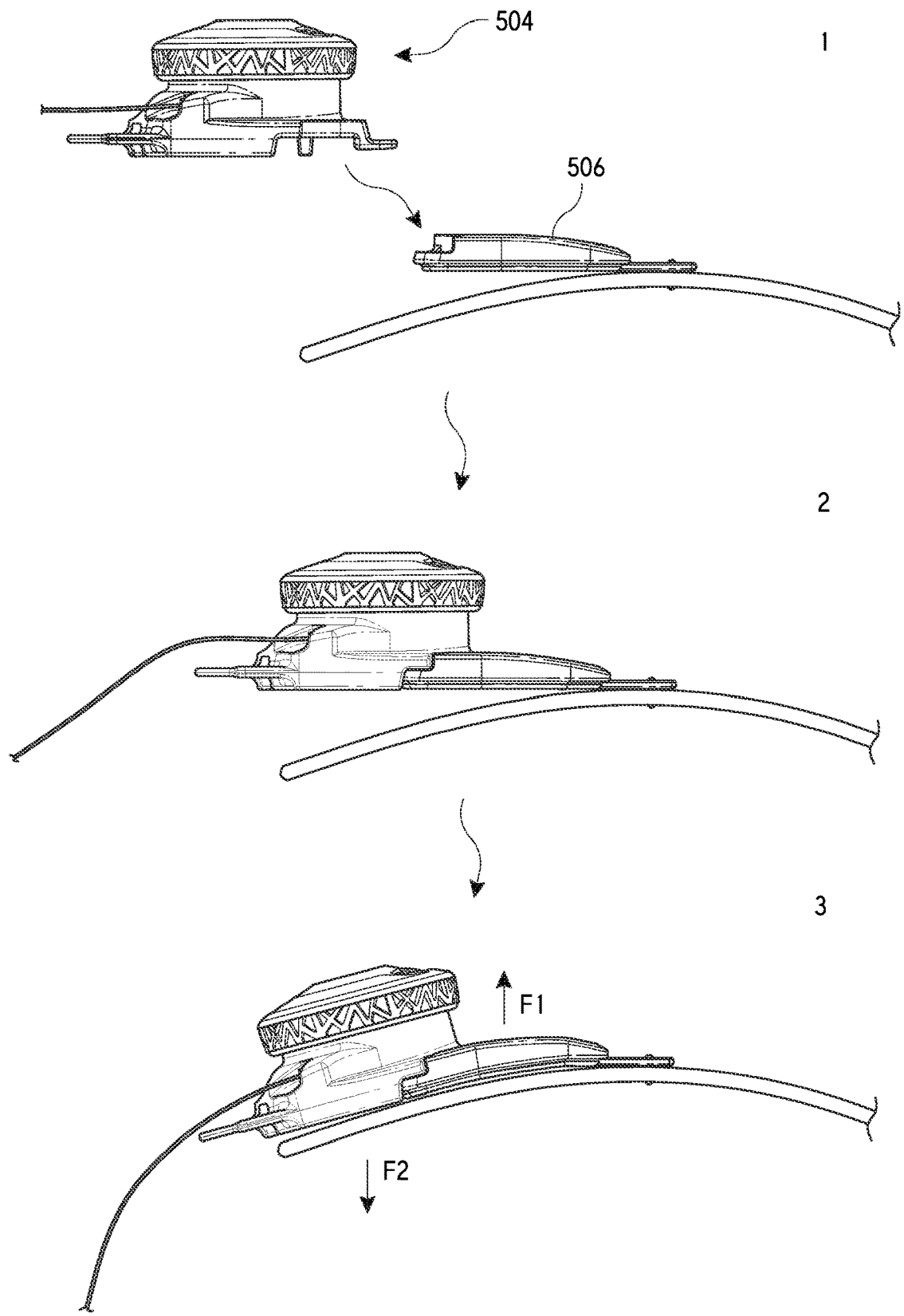
FIG. 13 illustrates a particular sequence that shows the coupling of a male component of a particular closure system or device with a female component of the first closure device.

Referring now to FIG. 13, a particular sequence 1300 is shown that illustrates the coupling of the male component 504 of the first closure device 502 with the female component 506 of the first closure device 502. In this example, the female component 506 is coupled to a material 1302 by a stitching flange 1304. The male component is then coupled to the female component 506 in a manner similar to that described above in connection with at least FIG. 5A-B. Next, the reel mechanism 530 of the male component 504 may be rotated or adjusted as desired to fine tune a tension applied to the lace 1306. As the lace 514 is tensioned, the lace 514 may tend to pull the male component 504 from the female component 506 in opposing directions so that various internal surfaces of the male component 504 and the female component 506 are pressed or biased together, as discussed above in connection with at least FIG. 8B.

Additionally, forces F1 and F2 may be imparted so that various internal surfaces of the male component 504 and the female component 506 are pressed together with a force components generally aligned with forces F1 and F2. This may beneficially make it more difficult to release or decouple the male component 504 from the female component 506 without releasing tension on the lace 1306 using the reel 530. Accordingly, an individual must typically untension the lace 1306 using the reel 530 in order to uncouple the two components 504, 506, which reduces or prevents lace shortening and over storage of the lace within the tightening mechanism. FIG. 13 further illustrates bending of the male component 504 and the female component 506 when lace 1306 is under tension. This may beneficially assist the system to maintain a relatively low-profile and/or increase the difficulty in uncoupling the components. In particular, as may be readily understood with reference to FIG. 13, the mated components lie about or approximately flat against the material 1302 and are, thus, virtually unable to snag objects in vicinity of mated components.

Figure 14:
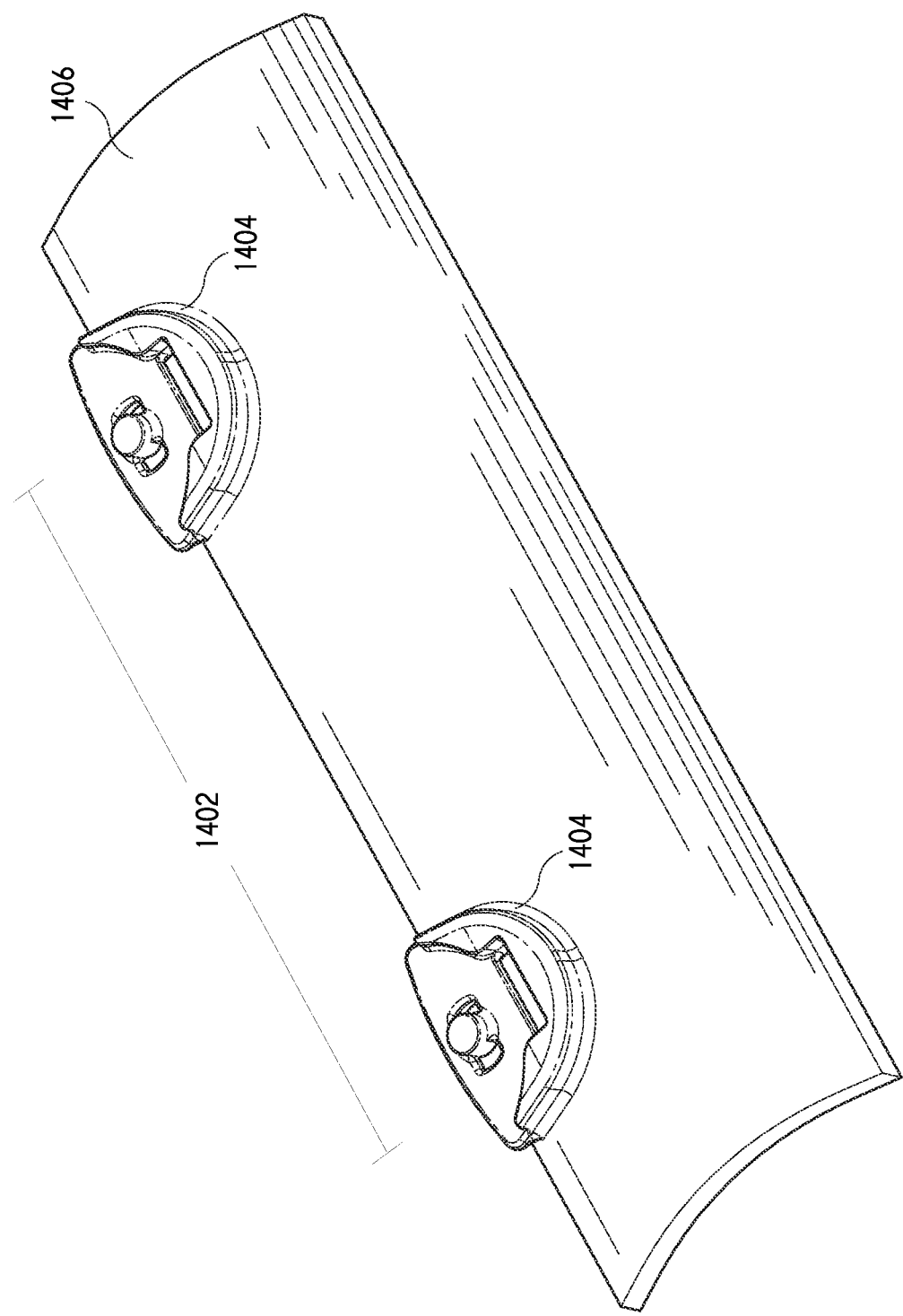
FIG. 14 illustrates a ganged pair of female components of a particular closure system or device.

Referring now to FIG. 14, illustrated is an backing material 1406 that may be used to form or otherwise define an edge of a brace. The backing material 1406 may be made of a relatively hard or soft material, including: foam, fleece, neoprene, TPU, silicone, hook & loop fabric (loop side), a pressure sensitive adhesive (e.g., BSA), and the like. In instances where a pressure sensitive adhesive (e.g., BSA) is used, various fabrics or other materials may be subsequently added by a physician or the user as desired and/or needed. The backing material 1406 may be inserted within a fabric body of a brace and may include a plurality of female components 1404 that are configured to couple with corresponding male components (not shown) as described above. In some embodiments, the female components 1404 may be formed into the backing material 1406, such as during a molding process. In other embodiments, the female components 1404 may be insert molded into the backing material 1406 or subsequently coupled therewith, such as via stitching, adhesive bonding, RF welding, heat welding, mechanically fastening, and the like. The female components 1404 may have a spacing 1402 between adjacent components as desired.

Figure 7A:
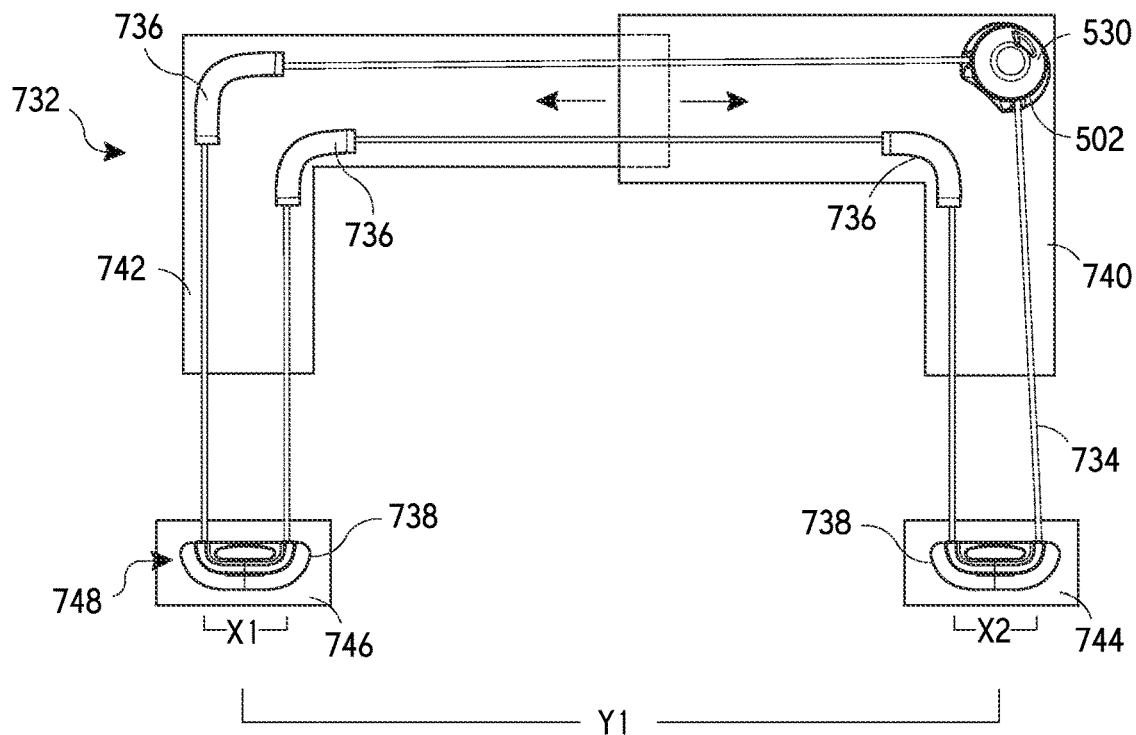
FIGS. 7A-H illustrate various telescoping closure systems or devices that may be used to close and tighten or loosen a brace.
Figure 7B:
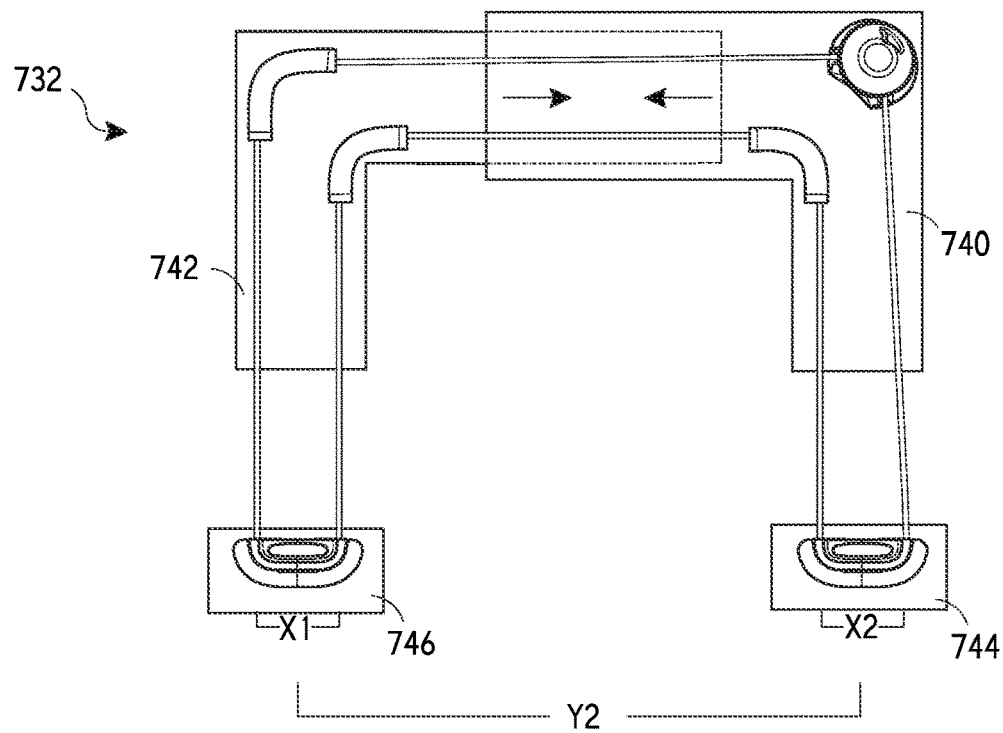

Referring now to FIGS. 7A-B illustrated is an example of a telescoping reel panel 732 whereby lace 734 is threaded to a first closure device 502 as discussed above in connection with at least FIGS. 5A-B, and also to guide segments 736 and guide members 738. In this example, the first closure device 502 and the guide segments 736 are each generally coupled to a top portion of one of a first panel 740 and a second panel 742 of the telescoping reel panel 732, and the guide members 738 are each generally coupled to a top portion of one of a first section 744 and a second section 746 of a particular brace 748.

The second panel 742 is inserted within a lumen or channel of the first panel 740 such that the second panel 742 may be slid out of the lumen of first panel 740 to increase a distance Y1 between the guide member 738 as shown in FIG. 7A. The second panel 742 may also be slid into the lumen of first panel 740 to decrease a distance a distance Y2 between the guide members 738 as shown in FIG. 7B. The configuration of telescoping reel panel 732 is such that the spacing of the individual guide members 738 remains approximately the same. In use, the distance between the guide member 738 may be set by sliding of the second panel 742 within the lumen of the first panel 740 and then the reel mechanism 530 may be rotated (e.g., counterclockwise) tension the lace 734 and tighten the brace about the user's limb or bodily segment.

Figure 7C:
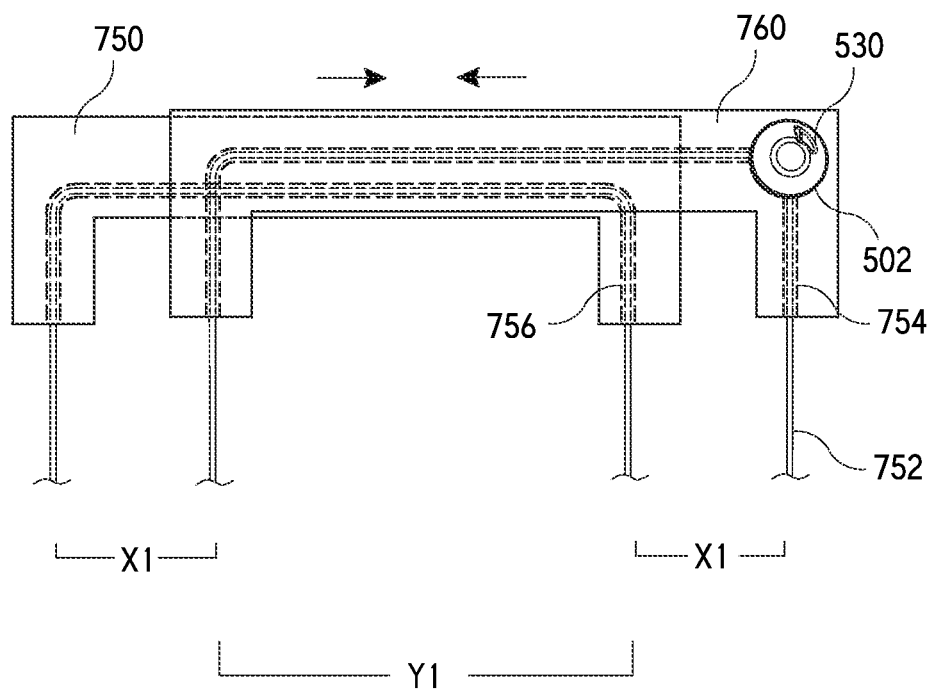
Figure 7D:
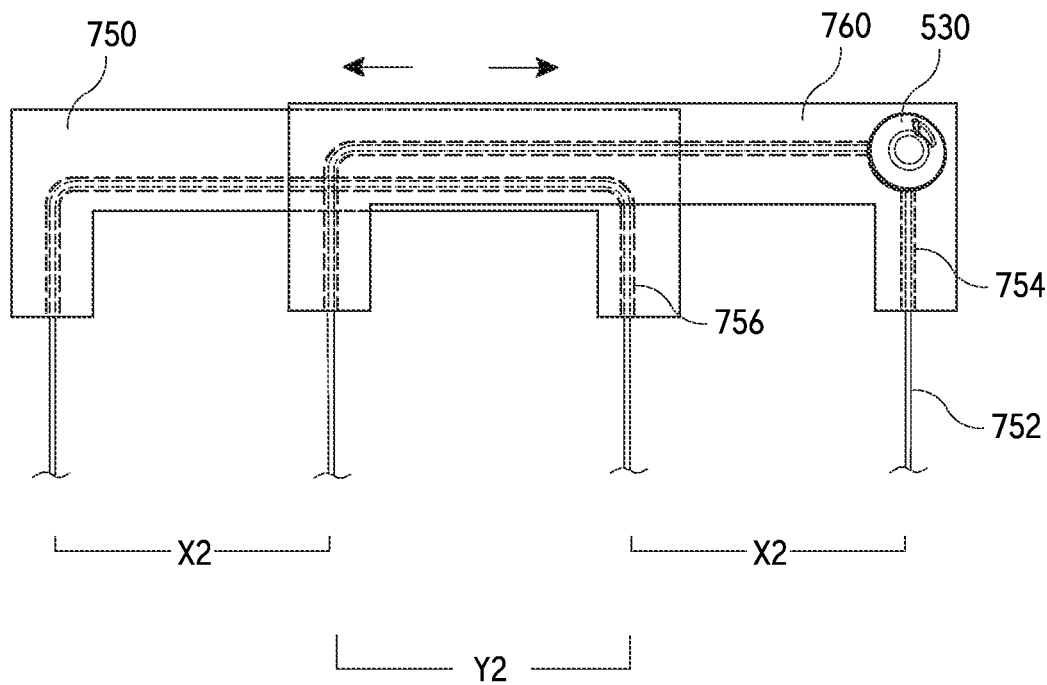

FIGS. 7C-F illustrate an example second telescoping reel panel 750 whereby lace 752 is threaded to the first closure device 502 as discussed above in connection with at least FIGS. 5A-B, and also to first tubing 754, second tubing 756, and guide members 758. In this example, the first closure device 502 is generally coupled to a top portion of a first panel 760 of the telescoping reel panel 750, and each of the first tubing 754 and second tubing 756 is generally incorporated within or in portions of one of the first panel 760 and a second panel 762 of the telescoping reel panel 750. This is illustrated in FIGS. 7C-D by phantom lines. In alternate embodiments, stitching and/or a particular cross-stitch pattern may be used to form a passage within the first panel 760 and the second panel 762 to take the place of or replace one or both of the first tubing 754 and the second tubing 756.

Figure 7E:
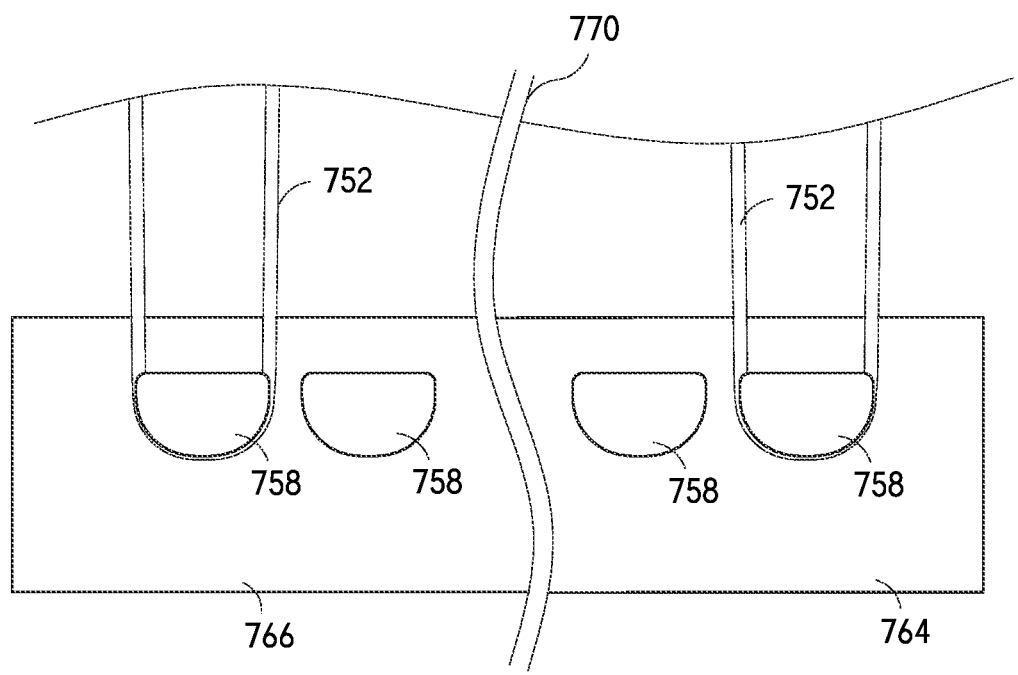
Figure 7F:
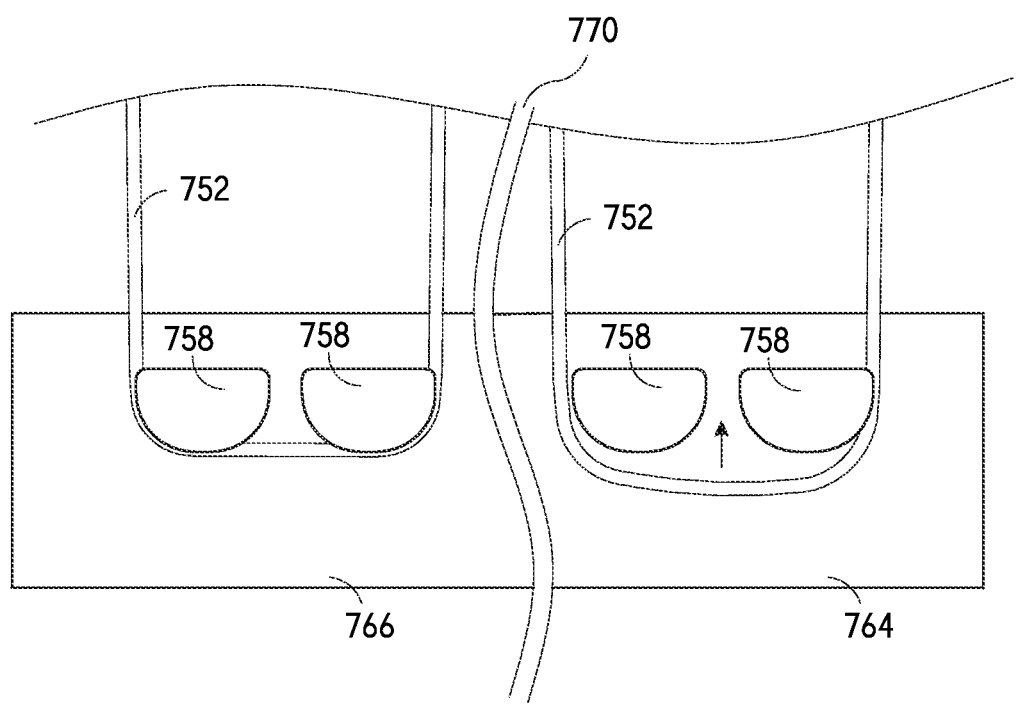

The guide members 758 in contrast are generally coupled to a top portion of one of a first section 764 and a second section 766 of a particular brace 768. This is illustrated in FIGS. 7E-F, where the lace 752 in one embodiment may be threaded to a particular one of the guide members 758 at each of the first section 764 and the second section 766, or in another embodiment may be threaded to a pair of guide members 758 at each of the first section 764 and the second section 766. It may be beneficial in some embodiments to thread the lace 752 to a pair of the guide members 758 as shown in FIG. 7F to distribute load imparted by the lace 752 when tensioned over an area greater than that would be imparted when the lace 752 is threaded only to a particular one of the guide members 758 as shown in FIG. 7E. In FIGS. 7E-F, a discontinuity marker 770 illustrates existence of an arbitrary spatial distance between the first section 764 and the second section 766 of the brace 768.

The second panel 762 is positioned behind the first panel 760 and is slidable relative thereto. In use, the second panel 762 may be slid relative to the first panel 760 to increase a spacing between the first section 764 and the second section 766 to a distance Y1, as shown in FIG. 7A. Alternatively, the second panel 762 may be slid relative to the first panel 760 to decrease a spacing between the first section 764 and the second section 766 to a distance Y2, as shown in FIG. 7B. In contrast to the telescoping reel panel of FIGS. 7A-B, when the second panel 762 is slid relative to the first panel 760, the distance between the laces of the first section 764 and the second section 766 changes as shown by distances X1 and X2 in FIGS. 7C-D. The configuration of the guide members 758 allows the user to adjust the spacing of the end portion or segment of the lace based on the lace spacing of the first section 764 and the second section 766 due to sliding of the first panel 760 and second panel 762. The reel mechanism 530 may then be used to tension the lace 752 and thereby tighten the brace about a user's limb or bodily segment.

Figure 7G:
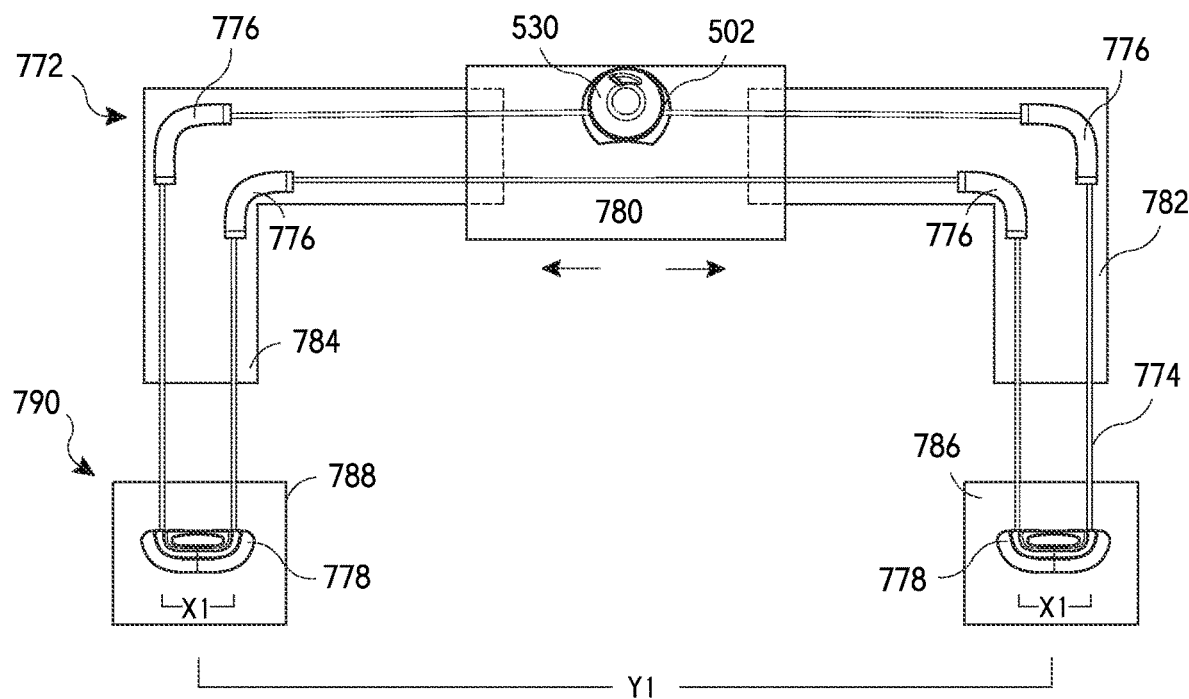
Figure 7H:
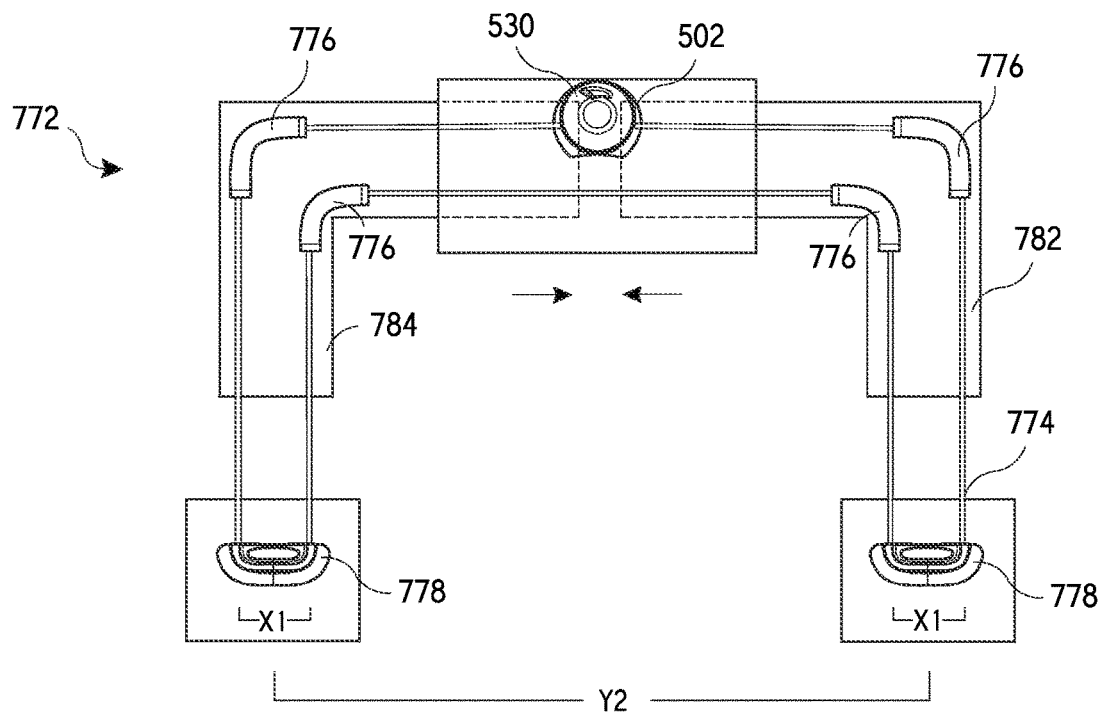

FIGS. 7G-H illustrate another example of a telescoping reel panel 772 whereby lace 774 is generally threaded to the first closure device 502 as discussed above in connection with at least FIGS. 5A-B, and to guide segments 776 and guide members 778. In this example, the first closure device 502 is generally coupled to a top portion of a first panel 780 of the telescoping reel panel 772, and the guide segments 776 are generally coupled to a top portion of one of a second panel 782 and a third panel 784 of the telescoping reel panel 772. Additionally, the guide members 778 are generally coupled to a top portion of one of a first section 786 and a second section 788 of a particular brace 790.

The second panel 782 and third panel 784 are inserted within a lumen or channel of the first panel 780 such that the second panel 782 and third panel 784 may be slid into and out of the lumen of the first panel 780 to increase a distance Y1 between the guide members 778 as shown in FIG. 7G, or decrease a distance a distance Y2 between the guide members 778 as shown in FIG. 7H as desired. Similar to the telescoping reel panel of FIGS. 7A-B, the configuration of telescoping reel panel 772 is such that the spacing of the individual guide members 778 remains approximately the same regardless of the telescoping of second or third panels, 782 and 784, relative to first panel 780. In some embodiments, the second panel 782 and third panel 784 may be independently telescoped or slid relative to first panel 780 such that the first panel 780 may be positioned closure to the second panel 782 or third panel 784 as desired. This may be useful when it is desired to position the first panel 780 and reel mechanism 530 closer to the user's hand for tensioning. In use, the distance between the guide member 778 may be set by sliding of the second panel 782 and/or third panel 784 within the lumen of the first panel 780 and then operating the reel mechanism 530 to tension the lace 774 and thereby tighten the brace about the user's limb or bodily segment.

Figure 15:
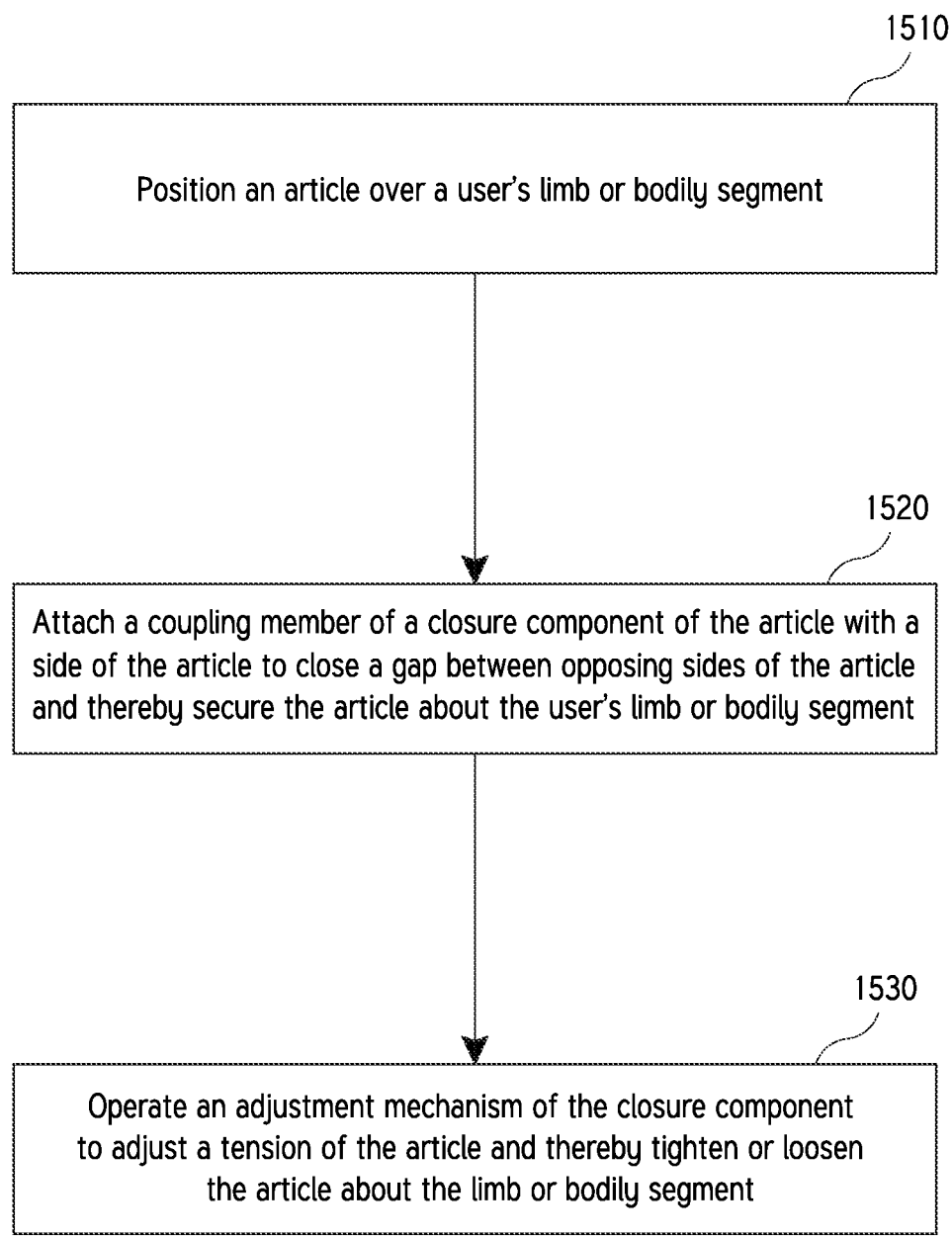
FIG. 15 illustrates an example method for tightening a brace or article.

Referring now to FIG. 15, a method of adjusting a tightness of an article about a limb or bodily segment of a user is illustrated. At block 1510, an article, such as a brace, is positioned over the limb or bodily segment of the user. As described herein, the article may include: an article body having a first side, a second side, and a gap therebetween and a closure component coupled with and offset from the first side of the article body. The closure component may include: a coupling member positioned toward a distal end of the closure component and an adjustment mechanism that is operable to tension the article body after the article body is secured to the user's limb or bodily segment. At block 1520, the coupling member is attached with the second side of the article body to close the gap and secure the article about the user's limb or bodily segment. At block 1530, the adjustment mechanism is operated to adjust a tension of the article body and thereby tighten the article about the limb or bodily segment.

In some embodiments, the steps of attaching the coupling member and operating the adjustment mechanism are performed with a single hand. In some embodiments, the step of attaching the coupling member includes inserting a flanged tab within a coupling aperture positioned on the second side of the article body. The flanged tab and coupling aperture may be non-releasable from a coupled engagement while the article remains under tension.

In some embodiments, a tension member is operably coupled with the adjustment mechanism and with the first side of the article body. The tension member is typically tensionable via operation of the adjustment mechanism to tension the article body. In some embodiments, the step of operating the adjustment mechanism includes rotating a knob of a reel mechanism in a first direction to wind the tension member around a channel of a spool that is positioned within a housing of the reel mechanism. In such embodiments, winding of the tension member around the spool's channel tensions the tension member. In some embodiments, the tension member is slidably coupled with a guide member and the tension member and guide member are disposed within a sleeve that spans a gap between the first side of the article body and a proximal end of the closure component. In such embodiments, tensioning of the tension member may cause the guide member to slide within the sleeve.

In some embodiments, the method further includes locking or securing the adjustment mechanism after the article body is tensioned to impede further operation of the adjustment mechanism. In some embodiments, the method additionally includes releasing a tension of the tension member via the adjustment mechanism and detaching the coupling member from the second side of the article body to allow the article to be removed from the user's limb or bodily segment.

Having described several embodiments, it will be recognized by those of skill in the art that various modifications, alternative constructions, and equivalents may be used without departing from the spirit of the invention. Additionally, a number of well-known processes and elements have not been described in order to avoid unnecessarily obscuring the present invention. Accordingly, the above description should not be taken as limiting the scope of the invention.

As used herein and in the appended claims, the singular forms "a", "an", and "the" include plural referents unless the context clearly dictates otherwise. Thus, for example, reference to "a process" includes a plurality of such processes and reference to "the device" includes reference to one or more devices and equivalents thereof known to those skilled in the art, and so forth. Also, the words "comprise," "comprising," "include," "including," and "includes" when used in this specification and in the following claims are intended to specify the presence of stated features, integers, components, or steps, but they do not preclude the presence or addition of one or more other features, integers, components, steps, acts, or groups.

What is claimed is:

1. A closure component for an article comprising: a body portion having:
    a proximal end that is coupleable with a first side of the article via a tension member and a flexible or elastic material strip, the tension member extending from the proximal end of the body portion toward the first side of the article, and the flexible or elastic material strip being coupled with the proximal end of the body portion and with the first side of the article, the flexible or elastic material strip being positioned under the tension member such that the tension member is moveably positioned on a top surface of the flexible or elastic material strip between the body portion and the first side of the article and such that when the article is positioned about a limb or bodily segment, the flexible or elastic material strip is configured to be positioned between the tension member and the limb or bodily segment about which the article is positioned;
    a distal end having a coupling component that is coupleable with a second side of the article so as to close a gap between the first side and the second side of the article and thereby secure the article about the limb or bodily segment;
    an adjustment mechanism attached to the body portion, the adjustment mechanism being operable to adjust a tension of the article after the article is secured about the limb or bodily segment so as to tighten or loosen the article about the limb or bodily segment; and
    a channel for the tension member formed on the body portion, the channel having an opening through which the tension member is positioned and the channel being configured to route or direct the tension member between opposing sides of the body portion, wherein the channel extends from the proximal end to the distal end of the body portion;
    wherein the coupling component consists of a single tab consisting of a single flange, wherein the single tab is insertable within a coupling aperture positioned on the second side of the article, and wherein the single tab is positioned on the distal end of the body portion adjacent the adjustment mechanism such that the adjustment mechanism and the single tab are fixed in position relative to each other on the body portion and are moveable together relative to the first side and the second side of the article.

2. The closure component of claim 1, wherein the coupling component and coupling aperture are not capable of being released from a coupled engagement without releasing the tension of the article.

3. The closure component of claim 2, wherein the closure component comprises an additional coupling component that includes a single tab consisting of a single flange, wherein the single tab is insertable within an additional coupling aperture positioned on the second side of the article.

4. The closure component of claim 1, wherein the tension member is slidably coupled with at least one guide member positioned on the article's first side or attached to an extension member extending therefrom, the tension member being tensionable via the adjustment mechanism to tension the article about the limb or bodily segment.

5. The closure component of claim 4, wherein the adjustment mechanism comprises a reel-based assembly comprising:
   a housing;
   a spool positioned within the housing, the spool having a channel around which the tension member is wound; and
   a knob that is rotatable in a first direction to wind the tension member around the channel of the spool and thereby tension the tension member.

6. The closure component of claim 1, wherein the single flange of the single tab comprises a top surface along an extension of the single flange, the single tab further comprises a rear surface, the rear surface being orthogonal to the top surface, the top surface and the rear surface being at least partially insertable within the coupling aperture, wherein when the coupling component and the coupling aperture form a coupled engagement and when the adjustment mechanism operates to adjust the tension of the article to tighten the article about the limb or bodily segment, the adjustment of the tension of the article causes the top surface to engage with a downward protrusion disposed inside the coupling aperture, and the adjustment of the tension of the article further causes the rear surface to engage with a lip disposed inside the coupling aperture such that the coupling component and coupling aperture are not capable of being released from the coupled engagement without releasing the tension of the article.

7. A closure component for a brace, the brace having a main body that is configured to fit circumferentially around a limb or bodily segment, the brace having a first side and a second side that are separated by a gap, the closure component comprising:
   a panel member that is attachable to the brace so as to span the gap that separates the first side and the second side of the brace, the panel member having:
      a proximal end that is coupleable with the first side of the brace via at least two tension member segments and via at least two flexible or elastic material strips, wherein the at least two tension member segments are spaced longitudinally apart and extend laterally from the proximal end of the panel member toward the first side of the brace across the gap, and wherein the at least two flexible or elastic material strips are coupled with the proximal end of the panel member and with the first side of the brace so that each flexible or elastic material strip is positioned under a respective tension member segment such that the respective tension member is moveably positioned on a top surface of the respective flexible or elastic material strip between the panel member and the first side of the brace and such that when the brace is configured to fit circumferentially around the limb or bodily segment, the respective flexible or elastic material strip is configured to be positioned between the respective tension member and the limb or bodily segment;
      a distal end having a coupling member that is positionable across the gap and removably coupleable with the second side of the brace so as to close the gap between the first side and the second side of the brace and thereby secure the brace about the limb or bodily segment, the distal end being detachable from the second side of the brace; and
   an adjustment mechanism attached to the distal end of the panel member, the adjustment mechanism being detachable from the second side of the brace via detachment of the distal end of the panel member from the second side of the brace and the adjustment mechanism being operable to tension the at least two tension member segments after the brace is secured about the limb or bodily segment so as to tighten or loosen the brace about the user's limb or bodily segment;
   wherein the coupling member comprises a single tab consisting of a single flange, wherein the single tab is attached to the panel member adjacent the adjustment mechanism so that the adjustment mechanism and the single tab are fixed in position relative to each other about the panel member and are moveable together with the panel member relative to the first side and the second side of the brace; and
   wherein the panel member includes a channel for routing or directing the tension member segments between opposing sides of the panel member, wherein the channel extends from the proximal end to the distal end of the panel member.

8. The closure component of claim 7, wherein the panel member includes at least two coupling members spaced longitudinally apart that are coupleable with the second side of the brace to close the gap and secure the brace about the user's limb or bodily segment, wherein each coupling member is a single tab consisting of a single flange, wherein the single tab is attached to the panel member adjacent the adjustment mechanism so that the adjustment mechanism and each single tab are fixed in position relative to each other and are moveable together with the panel member relative to the first side and the second side of the brace.

9. The closure component of claim 8, wherein each single tab is insertable within a coupling aperture positioned on the second side of the brace.

10. The closure component of claim 8, wherein the at least two tension member segments comprise lace, and wherein the lace is slidably disposed within the channel, wherein the channel allows the lace to dynamically shift or adjust between the laterally separated tension member segments such that the brace is dynamically adjustable about the limb or bodily segment as the limb or bodily segment flexes or otherwise changes shape.

11. The closure component of claim 7, wherein the at least two tension member segments are formed from a single lace or are formed from one or more laces.

\* \* \* \* \*